US007932374B2

(12) United States Patent
Perera et al.

(10) Patent No.: US 7,932,374 B2
(45) Date of Patent: *Apr. 26, 2011

(54) COMPOSITIONS AND METHODS FOR THE MODIFICATION OF GENE EXPRESSION

(75) Inventors: Ranjan Perera, Carlsbad, CA (US); Stephen James Rice, Auckland (NZ); Clare Katherine Eagleton, Auckland (NZ)

(73) Assignee: Arborgen, Inc., Summerville, SC (US)

( * ) Notice: Subject to any disclaimer, the term of this patent is extended or adjusted under 35 U.S.C. 154(b) by 831 days.

This patent is subject to a terminal disclaimer.

(21) Appl. No.: 10/702,319

(22) Filed: Nov. 6, 2003

(65) Prior Publication Data
US 2005/0026162 A1 Feb. 3, 2005

Related U.S. Application Data

(63) Continuation-in-part of application No. 10/291,447, filed on Nov. 8, 2002, now abandoned, which is a continuation-in-part of application No. 10/137,036, filed on Apr. 30, 2002, now Pat. No. 7,211,711, which is a continuation-in-part of application No. 09/276,599, filed on Mar. 25, 1999, now Pat. No. 6,380,459, and a continuation-in-part of application No. 09/724,624, filed on Nov. 28, 2000, now abandoned, and a continuation-in-part of application No. 09/598,401, filed on Jun. 20, 2000, now Pat. No. 6,596,925, which is a continuation-in-part of application No. PCT/NZ00/00018, filed on Feb. 24, 2000.

(60) Provisional application No. 60/345,397, filed on Nov. 9, 2001, provisional application No. 60/425,087, filed on Nov. 8, 2002, provisional application No. 60/146,591, filed on Jul. 30, 1999.

(51) Int. Cl.
*C07H 21/04* (2006.01)
*C12N 5/14* (2006.01)

(52) U.S. Cl. .................. 536/24.1; 435/320.1; 435/419; 435/468

(58) Field of Classification Search ........................ None
See application file for complete search history.

(56) References Cited

U.S. PATENT DOCUMENTS

| 5,510,474 | A | 4/1996 | Quail et al. |
| 5,639,952 | A | 6/1997 | Quail et al. |
| 5,656,496 | A | 8/1997 | Quail et al. |
| 5,750,385 | A | 5/1998 | Shewmaker et al. |
| 5,910,415 | A | 6/1999 | Hodges et al. |
| 6,054,574 | A | 4/2000 | Quail et al. |
| 6,225,529 | B1 | 5/2001 | Lappegard et al. |
| 6,380,459 | B1 | 4/2002 | Perera et al. |
| 6,596,925 | B1 | 7/2003 | Perera et al. |
| 2003/0101478 | A1 | 5/2003 | Perera et al. |
| 2005/0244968 | A1 | 11/2005 | Perera et al. |

FOREIGN PATENT DOCUMENTS

| WO | WO 97/47756 | 12/1997 |
| WO | WO 00/58474 | 10/2000 |
| WO | WO 01/98485 | 12/2001 |

OTHER PUBLICATIONS

De Melis et al. AF 168777. Ducalyptus globulus caffeic acid O-methyltransferase gene, Aug. 19, 1999.*
AF168777.*
AAC62810, WO200058474A1, Perera R et al. Feb. 2, 2001, first entry.*
Asamizu, Erika et al., "Structural Analysis of *Arabidopsis thaliana* Chromosome 5.VIII. Sequence Features of the Regions of 1,081,958 by Covered by Seventeen Physically assigned P1 and TAC Clones", DNA Research, vol. 5, pp. 379-391 (1998).
Belknap, William R. and Garbarino, Joan E. "The Role of ubiquitin in plant senescence and stress responses," Trends in Plant Science vol. 1, No. 10:331-335, Oct. 1996.
Benfey et al., "The Cauliflower Mosaic Virus 35S Promoter: Combinatorial Regulation of Transcription in Plants," Science 250:959-966 (1990).
Callis, Judy et al., "Structure and Evolution of Genes Encoding Polyubiquitin and Ubiquitin-Like Proteins in *Arabidosis thaliana* Ecotype Columbia", Genetics, vol. 139, pp. 921-939 (1995).
Callis, Judy et al., "Ubiquitin Extension Proteins of *Arabidopsis thaliana*", JBC, vol. 265, pp. 12486-12493 (1990).
Christensen, Allen H. et al., "Maize polyubiquitin genes: structure, thermal perturbation of expression and transcript splicing, and promoter activity following transfer to protoplasts by electroporation", Plant Molecular Biology, vol. 18, pp. 675-689 (1992).
Curie, Catherine et al., "The activation process of *Arabidopsis thaliana* A1 gene encoding the translation elongation factor EF-1.alpha. is conserved among angiosperms", Plant Molecular Biology, vol. 18, pp. 1083-1089 (1992).
Ellis et al., "Maize Adh-1 promoter sequences control anaerobic regulation: addition of upstream promoter elements from constitutive genes is necessary for expression in tobacco," EMBO J. 6(1):11-16 (1987).
EMBL Accession No. D10851 (ATHCDC2BG), submitted Apr. 14, 2000.
EMBL Accession No. D63396 (NTBY2A, TOBBY2A), submitted Feb. 13, 1999.
EMBL Accession No. U12012 (PTU12012), submitted Mar. 23, 1996.
GenBank Accession No. AB016885, submitted. Dec. 27, 2000.
GenBank Accession No. AF075270, submitted Sep. 24, 1998.
GenBank Accession No. AF139445, submitted Jun. 1, 1999.
GenBank Accession No. AJ012552 (VFA012552), submitted Nov. 13, 1998.
GenBank Accession No. L41658 (SCFPOLY), submitted Nov. 28, 1995.
GenBank Accession No. U53418 (GMU53418), submitted May 28, 1997.
GenBank Accession No. U90350 (PRU90350), submitted Oct. 10, 1997.
GenBank Accession No. X53043 (LEEF1A), submitted May 9, 1995.
GenBank Accession No. X74814 (EGOMTRN), submitted Sep. 22, 1994.

(Continued)

*Primary Examiner* — Celine X Qian
(74) *Attorney, Agent, or Firm* — Cooley LLP

(57) ABSTRACT

Novel isolated vascular tissue-specific plant polynucleotide promoter sequences are provided, together with genetic constructs comprising such polynucleotides. Methods for using such constructs in modulating the transcription of DNA sequences of interest are also disclosed, together with transgenic plants comprising such constructs.

19 Claims, 10 Drawing Sheets

OTHER PUBLICATIONS

GenBank Accession No. Z14990 (ATUBC9), submitted May 18, 1993.
GenBank Accession No. AAC49014; submitted 1995 by Liu et al.
GenBank Accession No. AF041463; submitted Jan. 6, 1998 by Suhandono, et al.
GenBank Accession No. AF077743; submitted Jul. 13, 1998 by Rehli, M., et al.
GenBank Accession No. M55147 X51434; Liaud, M. and Cerff, R., Proc. Nat'l Acad. Sci., vol. 87, No. 22, pp. 8918-8922 (1990).
GenBank Assession No. U73588; submitted Oct. 7, 1996 by Pere-Grau, L., et al.
GenBank Accession No. U90350; submitted Feb. 24, 1997 by Walden, A.R., et al.
GenBank Accession No. X74814; submitted Aug. 27, 1993 by Poeyudomenge, O., et al.
GenBank GI:1838898, (Feb. 10, 1997).
GenPept Accession No. AAA68878, submitted Jun. 23, 1995.
GenPept Accession No. AAB21993, submitted May 7, 1993.
GenPept Accession No. AAD56019 (AF181491_1), submitted Sep. 22, 1999.
GenPept Accession No. CAA10056; submitted Nov. 12, 1998 by Fruehling, M.
GenPept Accession No. CAA63531; submitted Nov. 9, 1995 by Ruiter, R.K.
Girod, Pierre-Alain et al., "Homologs of the essential ubiquitin conjugating enzymes UBC1, 4 and 5 in yeast are encoded by a multigene family in *Arabidopsis thaliana*", Plant Journal, vol. 3, No. 4, pp. 545-552 (1993).
Imajuku, Yoshiro et al., "Exon-intron organization of the *Arabidopsis thaliana* protein kinase genes CDC2a and CDC2b", FEBS Letters, vol. 304, No. 1, pp. 73-77 (1992).
Kim et al, "A 20 nucleotide upstream element is essential for the nopaline synthase (nos) prometer activity", 1994, Plant Molecular Biology vol. 24 pp. 105-117.

Kojima et al, "Structure of the pine (*Pinus thunbergii*) chloropyll a/b-binding protein gene expressed in the absence of light", 1992, Plant Molecular Biology, vol. 19 pp. 405-410.
Kojima et al, Genbank Accession No. X61915 S39573, 1991.
Kumagai, F. et al., "The Involvement of Protein Synthesis Elongation Factor 1.alpha. in the Organization of Microtubules on the Perinuclear Region during the Cell Cycle Transition from M Phase to $G_1$ Phase in Tobacco BY-2 Cells", Bot. Acta., vol. 108, pp. 467-473 (1995).
Poeydomenge, Odile et al., "A cDNA Encoding S-Adenosyl-L-Methionine:Caffeic Acid 3-O-Methyltransferase from Eucalyptus", Plant Physiology, vol. 105, pp. 749-750 (1994).
Scharf, Klaus-Dieter, Materna, Tilo, Trueter, Eckardt, and Nover, Lutz. "Heat Stress Promoters and Transcription Factors," Results Probl Cell Differ 20:125-62, 1994.
SWISS-PROT Accession No. O24493 (MC1_PINRA), submitted Jul. 15, 1999.
Szczglowski et al., "Site-Specific Mutagenesis of the Nodule-Infected Cell Expression (NICE) Element and the AT-Rich Element ATRE-BS2* of the Sesbania rostrata Leghemoglobin glb3 Promoter," Plant Cell 6:317-322 (1994).
Tenhaken, Raimund et al., "Cloning of an Enzyme That Synthesizes a Key Nucleotide-Sugar Precursor of Hemicellulose Biosynthesis from Soybean: UDP-Glucose Dehydrogenase", Plant Physiology, vol. 112, pp, 1127-1134 (1996).
Voo, Kui Shin et al., "4-Coumarate:Coenzyme A Ligase from Loblolly Pine Xylem. Isolation, Characterization, and Complementary DNA Cloning", Plant Physiology, vol. 108, pp. 85-97 (1995).
Walden, Adrian R. et al., "Genes Expressed in Pinus radiata Male Cones Include Homologs to Anther-Specific and Pathogenesis Response Genes", Plant Physiology, vol. 121, pp. 1103-1116 (1999).

* cited by examiner

```
CTGAGCCATTTAATTCGAGAGCACATCGCCCAAAATTATTCTTCTTGCTGCCATAACTGTCGAATTTTCTC
TTTTAGGTAAGTAACCAATGATGCATCATGTTGACAAAAAGGCTGATTAGTATGATCTTGGAGTTGTTGGT
GCAAATTTGCAAGCTGACGATGGCCCCTCAGGGAAATTAAGGCGCCAACCCAGATTGCAAAGAGCACAAAG
AGCACGATCCAACCTTTCCTTAACAAGATCATCACCAGATCGGCCAGTAAGGGTAATATTAATTTAACAAA
TAGCTCTTGTACCGGGAACTCCGTATTTCTCTCACTTCCATAAACCCTGATTAATTTGGTGGGAAAGCGA
CAGCCAACCCACAAAAGGTCAGATGTCATCCCACGAGAGAGAGAGAGAGAGAGAGAGAGAGAGAGAGAGTT
TTCTCTCTATATTCTGGTTCACCGGTTGGAGTCAATGGCATGCGTGACGAATGTACATATTGGTGTAGGGT
CCAATATTTTGCGGGAGGGTTGGTGAACCGCAAAGTTCCTATATATCGAACCTCCACCACCATACCTCACT
TCAATCCCCACCATTTATCCGTTTTATTTCCTCTGCTTTCCTTTGCTCGAGTCTCGCGGAAGAGAGAGAAG
AGAGGAGAGGAGAGAATGGGTT
```

Figure 1

```
AGCACCATCA GCAAAAAATA GATGGGATAG AGTGGGACAC CACCTGTTCA GTTTGATTCC      60
CTTGAGATGA CCTACAGTGA TAGCTTGATG AATAAGATGG GATAATAGAT TCACCAGAGG     120
GATAAAAAGG TAGGGAGATA GGGGATCTCC CCGTCTGATG CCTCGGGTAG GTTGAAAATA     180
AGGCAAAAGT TCGCCGTTGA ATTTGACAGC AAAAGACACC GTCGTTATGC ATTGCATGAT     240
CCATTGTACC CATGTAGGGT GAAATCCTAG AGTGAGGAGA TAGTCCTTTA GAAAGTCCCA     300
TTCCACCCTA TCATAGGCTT TCTGCATATC CATTTTAAGA ACAGCCCGGA ATTGACGTCT     360
ACATTTTCTG ACTTTAAATT GATGTAGAAC CTCTTAGACT ATTAAAATAT TGTCCTGAAT     420
TTGACGTCCA CTGACAAAAG CGCTTTGCTC CTGGAAAATA AGTACAGGCA GGTAGGGCTT     480
AAGGCGATTG GCAATCACCT TAGAAATGAT CTTATATGCG TAATTACAAA GACTGATGGG     540
GCGGTATTGG TCTAATTGTT CAGGATGTGG TACCTTGGGT ATTAGGGCTA TGATGGTTCG     600
ATTGAGATTC GGTGGTATGA TGCCAGAATT AAAAAAGTGC TGCACTGATG AGAATAGTTC     660
ATCCTGGAGT ATATCCCAAT GATGCTGGTA GAAGAGTCCA TTCAAGCCAT CTGGACCGGG     720
GGCCTTGGTA AGTCCCAGTT GGAAAGTAGC CTCTCTAACT TCCTTCTTGG TAACAGGAGC     780
TATTAGGGAC ATATTCATCT CATTAGTAAC AACCTAAGGA CACTGGTTCA GAATAGGCAA     840
GTAGTCTCGA TGTCCCACTG TCTGAAATAG ATGTGAAAAG TAACCTATCG TCATCATCTT     900
CAAAATTTCA GGATCGCGCA CCCAAGCTTG ATTGTCATCC TGCAACATAC TAATCTTGTT     960
TCGTTGTTGT CTTTGTATAG TTGTTGCATG AAAAAATTTA GTATTTTGT  CCCCCCAGCT    1020
GAGCCATTTA ATTCGAGAGC ACATCGCCCA AAATTATTCT TCTTGCTGCC ATAACTGTCG    1080
AATTTTCTCT TTTAGGTAAG TAACCAATGA TGCGCCATGT TGACAAAAAG GCTGATTAGT    1140
ATGATCTTGG AGTTGTTGGT GCAAATTTGC AAGCTGACGA TGGCCCCTCA GGGAAATTAA    1200
GGCGCCAACC CAGATTGCAA AGAGCACAAA GAGCACGACC CAACCTTTCC TTAACAAGAT    1260
CATCACCAGA TCGGCCAGTA AGGGTAATAT TAATTTAACA AATAGCTCTT GTACCGGGAA    1320
CTCCGTATTT CTCTCACTTC CATAAACCCC TGATTAATTT GGTGGGAAAG CGACAGCCAA    1380
CCCACAAAAG GTCAGATGTC ATCCCACGAG AGAGAGAGAG AGAGAGAGAG AGAGAGAGTT    1440
TTCTCTCTAT ATTCTGGTTC ACCGGTTGGA GTCAATGGCA TGCGTGACGA ATGTACATAT    1500
TGGTGTAGGG TCCAATATTT TGCGGGAGGG TTGGTGAACC GCAAAGTTCC TATATATCGA    1560
ACCTCCACCA CCATACCTCA CTTCAATCCC CACCATTTAT CCGTTTTATT CCTCTGCTT     1620
TCCTTTGCTC GAGTCTCGCG GAAGAGAGAG AAGAGAGGAG AGGAGAGAAT GGGTTCGACC    1680
GGCTCCGAGA CCCAGATGAC CCCGACCCAA GTCTCGGACG ACGAGGCGAA CCTCTTCGCC    1740
ATGCAGCTGG CGAGCGCCTC CGTGCTCCCC ATGGTCCTAA AGGCCGCCAT CGAGATCGAC    1800
CTCCTCGAGA TCATGGCCAA GGACGGGCCG GGCGCGTTCC TCTCCACGGG GGAAATCGCG    1860
GCACAGCTCC CGACCCAGAA CCCCGAGGCA CCCGTCATGC TCGACCGGAT CTTCCGGCTG    1920
CTGGCCAGCT ACTCCGTGCT CACGTGCACC CTCCGCGACC TCCCCGATGG CAAGGTCGAG    1980
CGGCTCTACG GCTTAGCGCC GGTGTGCAAG TTCTTGGTCA AGAACGAGGA CGGGGTCTCC    2040
ATCGCCGCAC TCAACTTGAT GAACCAGGAC AAAATCCTCA TGGAAAGCTG GTATTACCTG    2100
AAAGATGCGG TCCTTGAAGG CGGAATCCCA TTCAACAAGG CGTACGGGAT GACCGCGTTC    2160
GAGTATCATG GCACCGACCC GCGATTCAAC AAGATCTTTA ACGGGGAAT  GTCTGATCAC    2220
TCCACCATTA CTATGAAGAA GATACTGGAA ACATACAAGG CTTCGAGGG  CCTCGAGACC    2280
GTGGTCGATG TCGGAGGCGG CACTGGGGCC GTGCTCAGCA TGATCGTTGC CAAATACCCA    2340
TCAATGAAAG GGATCAACTT CGACCGCCCC AACGGATTGA AGACGCCCCA CCCCTTCCTG    2400
GTGTCAAGCA CGTCGGAGGC GACATGTTCG TCAGCGTTCC AAAGGGAGAT GCCATTTTCA    2460
TGAAGTGGAT ATGCCATGAC TGGAGTGACG ACCATTGCGC GAAGTTCCTC AAGAACTGCT    2520
ACGATGCGCT TCCCAACAAT GGAAAGGTGA TCGTTGCAGA GTGCGTACTC CCTGTGTACC    2580
CAGACACGAG CCTAGCGACC AAGAATGTGA TCCACATCGA CTGCATCATG TTGGCCCACA    2640
ACCCAGGCGG GAAAGAGAGG ACACAGAAGG AGTTCGAGGC ATTGGCCAAA GGGGCCGGAT    2700
TTCAGGGCTT CCAAGTCATG TGCTGCGCTT TCGGCACTCA CGTCATGGAG TTCCTGAAGA    2760
CCGCTTGATC TGCTCCTCTG TGGTGATGTT CATGGTTCTT GGATTTGAAA GGTCGTGAAG    2820
GAGCCCTTTT CTCACAGTTG GCTTCGGCAT ACCAAGTTCT TCTCATAAAA GGAAACAATA    2880
AGAAGCGACT GTATGATGGC GCAAGTGGAA GTTACAAGAT TTGTTGTTTT ATGTCTATAA    2940
AGTTTTGAGT CTTCTGCATA CTGATTTCAC AGAATGTGTA ACGAAACGGC GTATATGGAT    3000
GTGCCTGAAT GATGGAAATT GTGATATTCT GTCTTCTTTT TCAGTAAATC ACTTCGAACA    3060
AAAAAAAAAA                                                          3070
```

Figure 2

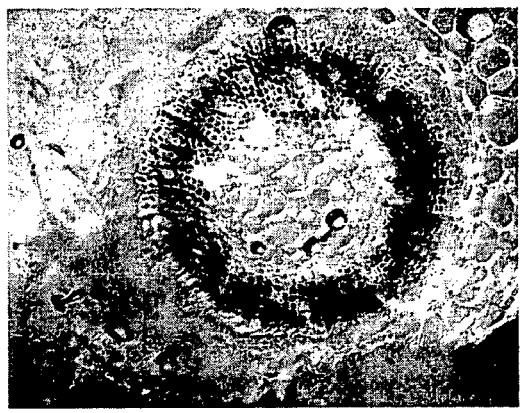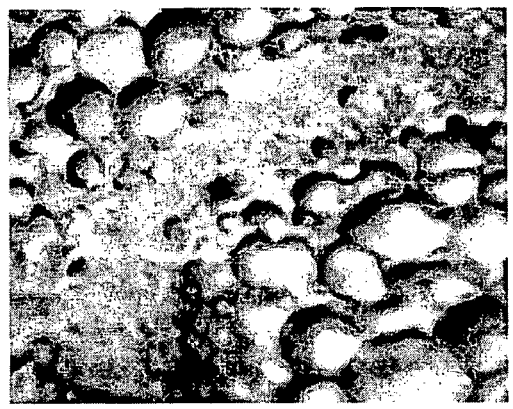
Figure 5

Figure 6

```
  -559  ATGCGCCATGTTGACAAAAAGGCTGATTAGTATGATCTTGGAGTTGTTGGTGCAAATTTG     60
  -499  CAAGCTGACGATGGCCCCTCAGGGAAATTAAGGCGCCAACCCAGATTGCAAAGAGCACAA    120
  -439  AGAGCACGACCCAACCTTTCCTTAACAAGATCATCACCAGATCGGCCAGTAAGGGTAATA    180
  -379  TTAATTTAACAAATAGCTCTTGTACCGGGAACTCCGTATTTCTCTCACTTCCATAAACCC    240
  -319  CTGATTAATTTGGTGGGAAAGCGACAGCCAACCCACAAAAGGTCAGATGTCATCCCACGA    300
  -259  GAGAGAGAGAGAGAGAGAGAGAGAGAGTTTTCTCTCTATATTCTGGTTCACCGGTTGG     360
  -199  AGTCAATGGCATGCGTGACGAATGTACATATTGGTGTAGGGTCCAATATTTTGCGGAGG    420
  -139  GTTGGTGAACCGCAAAGTTCCTATATATCGAACCTCCACCACCATACCTCACTTCAATCC    480
   -79  CCACCATTTATCCGTTTTATTTCCTCTGCTTTCCTTTGCTCGAGTCTCGCGGAAGAGAGA    540
   -19  GAAGAGAGGAGAGGAGAGAATGGGTTCGACCGGCTCCGAGACCCAGATGACCCCGACCCA    600
              +1
    42  AGTCTCGGACGACGAGGCGAACCTCTTCGCCATGCAGCTGGCGAGCGCCTCCGTGCTCCC    660
   102  CATGGTCCTAAAGGCCGCCATCGAGATCGACCTCCTCGAGATCATGGCCAAGGACGGGCC    720
   162  GGGCGCGTTCCTCTCCACGGGGGAAATCGCGGCACAGCTCCCGACCCAGAACCCCGAGGC    780
   222  ACCCGTCATGCTCGACCGGATCTTCCGGCTGCTGGCCAGCTACTCCGTGCTCACGTGCAC    840
   282  CCTCCGCGACCTCCCCGATGGCAAGGTCGAGCGGCTCTACGGCTTAGCGCGGTGTGCAA    900
   342  GTTCTTGGTCAAGAACGAGGACGGGGTCTCCATCGCCGCACTCAACTTGATGAACCAGGA    960
   402  CAAAATCCTCATGGAAAGCTGGTATTACCTGAAAGATGCGGTCCTTGAAGGCGGAATCCC   1020
   462  ATTCAACAAGGCGTACGGGATGACCGCGTTCGAGTATCATGGCACCGACCCGCGATTCAA   1080
   522  CAAGATCTTTAACCGGGGAATGTCTGATCACTCCACCATTACTATGAAGAAGATACTGGA   1140
   582  AACATACAAGGGCTTCGAGGGCCTCGAGACCGTGGTCGATGTCGGAGGCGGCACTGGGGC   1200
   642  CGTGCTCAGCATGATCGTTGCCAAATACCCATCAATGAAAGGGATCAACTTCGACCTTGCC   1260
   702  CCAACGGATTGAAGACGCCCCACCCCTTCCTGGTGTCAAGCACGTCGGAGGCGACATGTT   1320
   762  CGTCAGCGTTCCAAAGGGAGATGCCATTTTCATGAAGTGGATATGCCATGACTGGAGTGA   1380
   822  CGACCATTGCGCGAAGTTCCTCAAGAACTGCTACGATGCGCTTCCCAACAATGGAAAGGT   1440
   882  GATCGTTGCAGAGTGCGTACTCCCTGTGTACCCAGACACGAGCCTAGCGACCAAGAATGT   1500
   942  GATCCACATCGACTGCATCATGTTGGCCCACAACCCAGGCGGGAAAGAGAGGACACAGAA   1560
  1002  GGAGTTCGAGGCATTGGCCAAAGGGGCCGGATTTCAGGGCTTCCAAGTCATGTGCTGCGC   1620
  1062  TTTCGGCACTCACGTCATGGAGTTCCTGAAGACCGCTTGATCTGCTCCTCTGTGGTGATG   1680
  1122  TTCATGGTTCTTGGATTTGAAAGGTCGTGAAGGAGCCCTTTTCTCACAGTTGGCTTCGGC   1740
  1182  ATACCAAGTTCTTCTCATAAAAGGAAACAATAAGAAGCGACTGTATGATGGCGCAAGTGG   1800
  1242  AAGTTACAAGATTTGTTGTTTTATGTCTATAAAGTTTTGAGTCTTCTGCATACTGATTTC   1860
  1302  ACAGAATGTGTAACGAAACGGCGTATATGGATGTGCCTGAATGATGGAAATTGTGATATT   1920
  1362  CTGTCTTCTTTTTTCAGTAAATCACTTCGAACAAAAAAAAAAA                    1962
```

Figure 7

```
ATGCGCCATGTTGACAAAAAGGCTGATTAGTATGATCTTGGAGTTGTTG GTGCAAATTTG    60
CAAGCTGACG ATGGCCCC TCAG GGAAATTAAGGCGCCAACCCAGATTGCAAAGAGCACAA   120
AGAGCACGACCCAACCTTTCCTTAACAAGATCATCACCAGATCGGCCAGTAAGGGTAATA    180
TTAATTTAACAAATAGCTCTTGTACCGGGAACTCCGTATTTCTCTCAC TTCCATAAACCC   240
CTGATTAA TTTGGTGGG AAAG CGACAGCCA ACCCA CAAAAGGTCAGATGTCATCCCACGA 300
GAGAGAGAGAGAGAGAGAGAGAGAGAGAGAGTTTTCTCTCTATATTCTGGTTCACCGGTTGG  360
AGTCAATGGCATGCGTGACGAATGTACATATTGGTGTAGGGTCCAATATTTTGCG GGAGG   420
GTTGGTGAACCGCAAA GTTC CTAT ATATCGAACCTCCACCACCATACCTCACTTCAATCC  480
CCACCATTTATCCGTTTTATTTCCTCTGCTTTCCTTTGCTCGAGTCTCGCGGAA          534
```

Figure 8

```
GTGCAAATTTGCAAGCTGACG ATGGCCCC TCAG GGAAATTAAGGCGCCAACCCAGATTGC   60
AAAGAGCACAAAGAGCACGACCCAACCTTTCCTTAACAAGATCATCACCAGATCGGCCAG   120
TAAGGGTAATATTAATTTAACAAATAGCTCTTGTACCGGGAACTCCGTATTTCTCTCAC T  180
TCCATAAACCCCTGATTAA TTTGGTGGG AAAG CGACAGCCA ACCCA CAAAAGGTCAGATG 240
TCATCCCACGAGAGAGAGAGAGAGAGAGAGAGAGAGAGAGTTTTCTCTCTATATTCTGGT   300
TCACCGGTTGGAGTCAATGGCATGCGTGACGAATGTACATATTGGTGTAGGGTCCAATAT   360
TTTGCG GGAGGGTTGGTGAACCGCAAA GTTC CTAT ATATCGAACCTCCACCACCATACCT  420
CACTTCAATCCCCACCATTTATCCGTTTTATTTCCTCTGCTTTCCTTTGCTCGAGTCTCG   480
CGGAA                                                          485
```

Figure 9

```
TTCCATAAACCCCTGATTAA TTTGGTGGG AAAG CGACAGCCA ACCCA CAAAAGGTCAGAT  60
GTCATCCCACGAGAGAGAGAGAGAGAGAGAGAGAGAGAGAGTTTTCTCTCTATATTCTGG  120
TTCACCGGTTGGAGTCAATGGCATGCGTGACGAATGTACATATTGGTGTAGGGTCCAATA  180
TTTTGCG GGAGGGTTGGTGAACCGCAAA GTTC CTAT ATATCGAACCTCCACCACCATACC 240
TCACTTCAATCCCCACCATTTATCCGTTTTATTTCCTCTGCTTTCCTTTGCTCGAGTCTC  300
GCGGAA                                                        306
```

Figure 10

TGATTAATTTGGTGGG`AAAG`CGACAGCCA`ACCCA`CAAAAGGTCAGATGTCATCCCACGAG     60

AGAGAGAGAGAGAGAGAGAGAGAGAGAGAGTTTTCTCTCTATATTCTGGTTCACCGGTTGGA     120

GTCAATGGCATGCGTGACGAATGTACATATTGGTGTAGGGTCCAATATTTTGCG`GGAGGG`    180

`TTGGTGAACCGCAAAG`TTC`CTAT`ATATCGAACCTCCACCACCATACCTCACTTCAATCCC   240

CACCATTTATCCGTTTTATTTCCTCTGCTTTCCTTTGCTCGAGTCTCGCGGAA              293

Figure 11

`GGAGGGTTGGTGAACCGCAAAG`TTC`CTAT`ATATCGAACCTCCACCACCATACCTCACTTC   60

AATCCCCACCATTTATCCGTTTTATTTCCTCTGCTTTCCTTTGCTCGAGTCTCGCGGAA       119

Figure 12

AGTTC`CTAT`ATATCGAACCTCCACCACCATACCTCACTTCAATCCCCACCATTTATCCGT

TTTATTTCCTCTGCTTTCCTTTGCTCGAGTCTCGCGGAA

Figure 13

TCACTTCAATCCCCACCATTTATCCGTTTTATTTCCTCTGCTTTCCTTTGCTCGAGTCTC      60

GCGGAA                                                             66

GUS reporter gene expression driven by:
534bp OMT promoter
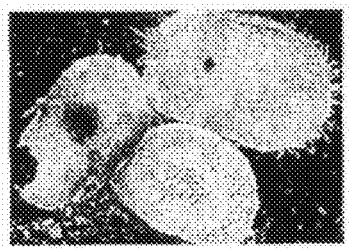
485bp OMT promoter fragment
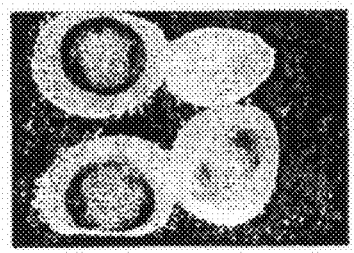
306bp OMT promoter fragment
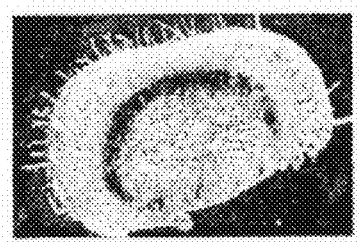
119bp OMT promoter fragment
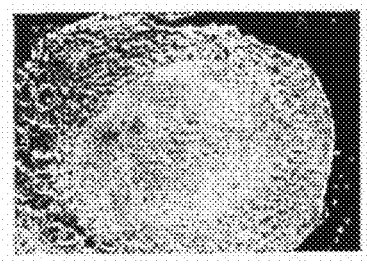
Figure 15

SEQUENCE LISTING

```
<160> NUMBER OF SEQ ID NOS: 137

<210> SEQ ID NO 1
<211> LENGTH: 3083
<212> TYPE: DNA
<213> ORGANISM: Pinus radiata
<220> FEATURE:
<221> NAME/KEY: 5'UTR
<222> LOCATION: (1)...(2064)
<220> FEATURE:
<221> NAME/KEY: intron
<222> LOCATION: (1196)...(2033)
<220> FEATURE:
<221> NAME/KEY: CDS
<222> LOCATION: (2065)...(2751)
<220> FEATURE:
<221> NAME/KEY: 3'UTR
<222> LOCATION: (2755)...(3083)

<400> SEQUENCE: 1 aaaaccctc  acaaatacat  aaaaaaaatt  ctttatttaa  ttatcaaact  ctccactacc       60
tttcccacca  accgttacaa  tcctgaatgt  tggaaaaaac  taactacatt  gatataaaaa     120
aactacatta  cttcctaaat  catatcaaaa  ttgtataaat  atatccactc  aaaggagtct     180
agaagatcca  cttggacaaa  ttgcccatag  ttggaaagat  gttcaccaag  tcaacaagat     240
```

-continued

| | |
|---|---|
| ttatcaatgg aaaaatccat ctaccaaact tactttcaag aaaatccaag gattatagag | 300 |
| taaaaaatct atgtattatt aagtcaaaaa gaaaaccaaa gtgaacaaat attgatgtac | 360 |
| aagtttgaga ggataagaca ttggaatcgt ctaaccagga ggcggaggaa ttccctagac | 420 |
| agttaaaagt ggccggaatc ccggtaaaaa agattaaaat ttttttgtag agggagtgct | 480 |
| tgaatcatgt tttttatgat ggaaatagat tcagcaccat caaaaacatt caggacacct | 540 |
| aaaattttga agtttaacaa aaataacttg gatctacaaa aatccgtatc ggattttctc | 600 |
| taaatataac tagaattttc ataactttca aagcaactcc tccctaacc gtaaaacttt | 660 |
| tcctacttca ccgttaatta cattccttaa gagtagataa agaaataaag taaataaaag | 720 |
| tattcacaaa ccaacaattt atttctttta tttacttaaa aaaacaaaaa gtttatttat | 780 |
| tttacttaaa tggcataatg acatatcgga gatccctcga acgagaatct tttatctccc | 840 |
| tggttttgta ttaaaaagta atttattgtg gggtccacgc ggagttggaa tcctacagac | 900 |
| gcgctttaca tacgtctcga gaagcgtgac ggatgtgcga ccggatgacc ctgtataacc | 960 |
| caccgacaca gccagcgcac agtatacacg tgtcatttct ctattggaaa atgtcgttgt | 1020 |
| tatccccgct ggtacgcaac caccgatggt gacaggtcgt ctgttgtcgt gtcgcgtagc | 1080 |
| gggagaaggg tctcatccaa cgctattaaa tactcgcctt caccgcgtta cttctcatct | 1140 |
| tttctcttgc gttgtataat cagtgcgata ttctcagaga ctttttcatt caaaggtatg | 1200 |
| gagttttgaa gggctttact cttaacattt gttttctttt gtaaattgtt aatggtggtt | 1260 |
| tctgtggggg aagaatcttt tgccaggtcc tttgggttt cgcatgttta tttgggttat | 1320 |
| ttttctcgac tatggctgac attactaggg ctttcgtgct ttcatctgtg ttttcttccc | 1380 |
| ttaataggtc tgtctctctg gaatatttaa ttttcgtatg taagttatga gtagtcgctg | 1440 |
| tttgtaatag gctcttgtct gtaaaggttt cagcaggtgt ttgcgtttta ttgcgtcatg | 1500 |
| tgtttcagaa ggccttttgca gattattgcg ttgtacttta atattttgtc tccaaccttg | 1560 |
| ttatagtttc cctcctttga tctcacagga acccttttctt ctttgagcat tttcttgtgg | 1620 |
| cgttctgtag taatatttta attttgggcc cgggttctga gggtaggtga ttattccagt | 1680 |
| gatgtgcttt ccctataagg tcctctatgt gtaagctgtt agggtttgtg cgttactatt | 1740 |
| gacatgtcac atgtcacata ttttcttcct cttatccttc gaactgatgg ttcttttttct | 1800 |
| aattcgtgga ttgctggtgc catattttat ttctattgca actgtatttt agggtgtctc | 1860 |
| tttcttttg atttcttgtt aatatttgtg ttcaggttgt aactatgggt tgctagggtg | 1920 |
| tctgccctct tcttttgtgc ttctttcgca gaatctgtcc gttggtctgt atttgggtga | 1980 |
| tgaattattt attccttgaa gtatctgtct aattagcttg tgatgatgtg caggtatatt | 2040 |
| cgttagtcat atttcaattt caagatgcag atctttgtca agactctcac cggtaagacc | 2100 |
| atcactctcg aggtcgagag ctctgacacc attgacaatg ttaaagctaa gatccaggac | 2160 |
| aaggaaggga ttccccccga ccagcagcgt ctgatcttcg caggaaagca gcttgaggac | 2220 |
| ggccgaaccc ttgccgatta caacatccag aaagaatcta ccctccacct tgttctccgt | 2280 |
| ttgaggggtg gcatgcaaat cttttgtaaaa acactaactg gaaagacaat tacattggaa | 2340 |
| gttgagagct cggacaccat tgacaacgtc aaggccaaga tccaggacaa ggaaggaatt | 2400 |
| cccccctgacc agcagaggct tatcttcgct ggtaagcagc tggaggatgg caggaccttg | 2460 |
| gctgattaca atattcaaaa ggaatcgacc ctgcatttgg tgcttcgtct aagaggaggc | 2520 |
| atgcaaatct ttgtgaaaac ccttacaggt aaaaccatta ctctggaagt ggaaagctcg | 2580 |
| gacaccattg acaatgtgaa ggctaagatc caggacaagg agggaattcc acctgaccag | 2640 |

```
cagaggttga tctttgccgg taagcagctg gaagatggtc gtactctcgc cgattacaat      2700
attcagaagg aatcgaccct tcacctggtg ctccgtctcc gcggtggctt ttaggtttgg      2760
gtgttatttg tggataataa attcgggtga tgttcagtgt ttgtcgtatt tctcacgaat      2820
aaattgtgtt tatgtatgtg ttagtgttgt ttgtctgttt cagaccctct tatgttatat      2880
ttttcttttc gtcggtcagt tgaagccaat actggtgtcc tggccggcac tgcaatacca      2940
tttcgtttaa tataaagact ctgttatccg ttatgtaatt ccatgttatg tggtgaaatg      3000
tggatgaaat tcttagaaat tattattgta atttgaaact tccttcgtca ataatctgca      3060
caacacattt accaaaaaaa aaa                                              3083

<210> SEQ ID NO 2
<211> LENGTH: 2064
<212> TYPE: DNA
<213> ORGANISM: Pinus radiata
<220> FEATURE:
<221> NAME/KEY: 5'UTR
<222> LOCATION: (1)...(2064)
<220> FEATURE:
<221> NAME/KEY: intron
<222> LOCATION: (1196)...(2033)

<400> SEQUENCE: 2 aaacccctc acaaatacat aaaaaaaatt ctttatttaa ttatcaaact ctccactacc       60
tttcccacca accgttacaa tcctgaatgt tggaaaaaac taactacatt gatataaaaa     120
aactacatta cttcctaaat catatcaaaa ttgtataaat atatccactc aaaggagtct     180
agaagatcca cttggacaaa ttgcccatag ttggaaagat gttcaccaag tcaacaagat     240
ttatcaatgg aaaaatccat ctaccaaact tactttcaag aaaatccaag gattatagag     300
taaaaaatct atgtattatt aagtcaaaaa gaaaaccaaa gtgaacaaat attgatgtac     360
aagtttgaga ggataagaca ttggaatcgt ctaaccagga ggcggaggaa ttccctagac     420
agttaaaagt ggccggaatc ccggtaaaaa agattaaaat ttttttgtag agggagtgct     480
tgaatcatgt ttttatgat ggaaatagat tcagcaccat caaaaacatt caggacacct     540
aaaattttga agtttaacaa aaataacttg gatctacaaa aatccgtatc ggattttctc     600
taaatataac tagaattttc ataactttca aagcaactcc tcccctaacc gtaaaacttt     660
tcctacttca ccgttaatta cattccttaa gagtagataa agaaataaag taaataaaag     720
tattcacaaa ccaacaattt atttctttta tttacttaaa aaaacaaaaa gtttatttat     780
tttacttaaa tggcataatg acatatcgga gatccctcga acgagaatct tttatctccc     840
tggttttgta ttaaaaagta atttattgtg gggtccacgc ggagttggaa tcctacagac     900
gcgctttaca tacgtctcga gaagcgtgac ggatgtgcga ccggatgacc ctgtataacc     960
caccgacaca gccagcgcac agtatacacg tgtcatttct ctattggaaa atgtcgttgt    1020
tatccccgct ggtacgcaac caccgatggt gacaggtcgt ctgttgtcgt gtcgcgtagc    1080
gggagaaggg tctcatccaa cgctattaaa tactcgcctt caccgcgtta cttctcatct    1140
tttctcttgc gttgtataat cagtgcgata ttctcagaga cttttcatt caaaggtatg    1200 gagttttgaa gggctttact cttaacattt gttttctttt gtaaattgtt aatggtggtt    1260
tctgtggggg aagaatcttt tgccaggtcc ttttgggttt cgcatgttta tttgggttat    1320
ttttctcgac tatggctgac attactaggg ctttcgtgct ttcatctgtg ttttcttccc    1380
ttaataggtc tgtctctctg gaatatttaa ttttcgtatg taagttatga gtagtcgctg    1440
tttgtaatag gctcttgtct gtaaaggttt cagcaggtgt ttgcgtttta ttgcgtcatg    1500
```

```
tgtttcagaa ggcctttgca gattattgcg ttgtacttta atattttgtc tccaaccttg   1560
ttatagtttc cctcctttga tctcacagga acccttctt ctttgagcat tttcttgtgg    1620
cgttctgtag taatatttta attttgggcc cgggttctga gggtaggtga ttattccagt   1680
gatgtgcttt ccctataagg tcctctatgt gtaagctgtt agggtttgtg cgttactatt   1740
gacatgtcac atgtcacata ttttcttcct cttatccttc gaactgatgg ttcttttttct  1800 aattcgtgga ttgctggtgc catattttat ttcattgca actgtatttt agggtgtctc    1860 tttcttttttg atttcttgtt aatatttgtg ttcaggttgt aactatgggt tgctagggtg  1920
tctgccctct tcttttgtgc ttcttcgca gaatctgtcc gttggtctgt atttgggtga    1980
tgaattattt attccttgaa gtatctgtct aattagcttg tgatgatgtg caggtatatt   2040
cgttagtcat atttcaattt caag                                          2064

<210> SEQ ID NO 3
<211> LENGTH: 1226
<212> TYPE: DNA
<213> ORGANISM: Pinus radiata
<220> FEATURE:
<221> NAME/KEY: 5'UTR
<222> LOCATION: (1)...(1226)

<400> SEQUENCE: 3
aaaccccctc acaaatacat aaaaaaaatt ctttatttaa ttatcaaact ctccactacc     60
tttcccacca accgttacaa tcctgaatgt tggaaaaaac taactacatt gatataaaaa   120
aactacatta cttcctaaat catatcaaaa ttgtataaat atatccactc aaaggagtct   180
agaagatcca cttggacaaa ttgcccatag ttggaaagat gttcaccaag tcaacaagat   240
ttatcaatgg aaaaatccat ctaccaaact tactttcaag aaaatccaag gattatagag   300
taaaaaatct atgtattatt aagtcaaaaa gaaaaccaaa gtgaacaaat attgatgtac   360
aagtttgaga ggataagaca ttggaatcgt ctaaccagga ggcggaggaa ttccctagac   420
agttaaaagt ggccggaatc ccggtaaaaa agattaaaat tttttttgtag agggagtgct   480 tgaatcatgt tttttatgat ggaaatagat tcagcaccat caaaaacatt caggacacct   540
aaaattttga agtttaacaa aaataacttg gatctacaaa aatccgtatc ggattttctc   600
taaatataac tagaattttc ataactttca aagcaactcc tcccctaacc gtaaaacttt   660
tcctacttca ccgttaatta cattccttaa gagtagataa agaaataaag taaataaaag   720
tattcacaaa ccaacaattt atttctttta tttacttaaa aaaacaaaaa gtttatttat   780
tttacttaaa tggcataatg acatatcgga gatccctcga acgagaatct tttatctccc   840
tggttttgta ttaaaaagta atttattgtg gggtccacgc ggagttggaa tcctacagac   900
gcgctttaca tacgtctcga gaagcgtgac ggatgtgcga ccggatgacc ctgtataacc   960
caccgacaca gccagcgcac agtatacacg tgtcatttct ctattggaaa atgtcgttgt  1020
tatccccgct ggtacgcaac caccgatggt gacaggtcgt ctgttgtcgt gtcgcgtagc  1080
gggagaaggg tctcatccaa cgctattaaa tactcgcctt caccgcgtta cttctcatct  1140
tttctcttgc gttgtataat cagtgcgata ttctcagaga gcttttcatt caaaggtata  1200
ttcgttagtc atatttcaat ttcaag                                       1226

<210> SEQ ID NO 4
<211> LENGTH: 485
<212> TYPE: DNA
<213> ORGANISM: Pinus radiata
<220> FEATURE:
```

<221> NAME/KEY: 5'UTR
<222> LOCATION: (1)...(431)
<220> FEATURE:
<221> NAME/KEY: TATA_signal
<222> LOCATION: (350)...(356)
<220> FEATURE:
<221> NAME/KEY: CAAT_signal
<222> LOCATION: (326)...(333)

<400> SEQUENCE: 4

```
agtaaaattg gcccatgtag gactaagtca aaatcaaaat tccatctcta aaagcggaac    60
tttgtcccct gaaaattttg actaatttcc aaccaaaaaa aagtgggga aaatataaaa    120
ctctaactaa taaaacaata atcaccaaaa atctatcacc aaaaatgaaa aaagattttg    180
aatactaggc catatgagct acacaaattt caaaagtatc ttacacttat tacgcacccg    240
gatgtcccca ctttcgaaaa acccgtttca agcctttcac gaaagtccaa cggtcagaaa    300
attcaaaatg actgtttgag gcagagccaa tctaggacca cgctccattt atatatggcc    360
tctgcttctc tcgaccctta gagtcctctg ctctgcgaat cttgttgtta gttactgtgt    420
acgctgtaac aatggatgcc tatgagaagt tggagaaggt gggagaagga acctatggga    480
aggtg                                                               485
```

<210> SEQ ID NO 5
<211> LENGTH: 246
<212> TYPE: DNA
<213> ORGANISM: Pinus radiata
<220> FEATURE:
<221> NAME/KEY: 5'UTR
<222> LOCATION: (1)...(167)
<220> FEATURE:
<221> NAME/KEY: TATA_signal
<222> LOCATION: (185)...(191)

<400> SEQUENCE: 5

```
tgagaacatg ataagctgtg taaattcatg ctagtcacca taactttct cattgcttt    60
catccacact gttgattcat tcattatata agatcagatt cgtatgatat acaggcaacc   120
atagaaacaa ccagcaaagt tactagcagg aaatccaact aggtatcatg aagactacca   180
acgcaggctc gataatgttg gtgctcatta ttttgggtg ctgtttcatt ggggtcatag    240
ctacat                                                              246
```

<210> SEQ ID NO 6
<211> LENGTH: 600
<212> TYPE: DNA
<213> ORGANISM: Pinus radiata
<220> FEATURE:
<221> NAME/KEY: 5'UTR
<222> LOCATION: (1)...(167)
<220> FEATURE:
<221> NAME/KEY: TATA_signal
<222> LOCATION: (471)...(477)
<220> FEATURE:
<221> NAME/KEY: CAAT_signal
<222> LOCATION: (444)...(451)

<400> SEQUENCE: 6

```
caccaattta atgggatttc agatttgtat cccatgctat tggctaagcc atttttctta    60
ttgtaatcta accaattcca atttccaccc tggtgtgaac tgactgacaa atgcggcccg   120
aaaacagcga atgaaatgtc tgggtgatcg gtcaaacaag cggtgggcga gagaacgcgg   180
gtgttggcct agccgggatg ggggtaggta gacggcgtat taccggcgag ttgtccgaat   240
ggagttttcg gggtaggtag taacgtagac gtcaatggaa aaagtcataa tctccgtcaa   300
```

| | |
|---|---:|
| aaatccaacc gctccttcac accgcagagt tggtggccac gggaccctcc acccactcac | 360 |
| tcaatcgatc gcctgccgtg gttgcccatt attcaaccat acgccacttg actcttcacc | 420 |
| aacaattcca ggccggcttt cgagacaatg tactgcacag gaaaatccaa tataaaaggc | 480 |
| cggcctccgc ttccttctca gtagccccca gctcattcaa ttcttcccac tgcaggctac | 540 |
| atttgtcaga cacgttttcc gccattttc gcctgtttct gcggagaatt tgatcaggtt | 600 |

<210> SEQ ID NO 7
<211> LENGTH: 591
<212> TYPE: DNA
<213> ORGANISM: Eucalyptus grandis
<220> FEATURE:
<221> NAME/KEY: 5'UTR
<222> LOCATION: (1)...(591)
<220> FEATURE:
<221> NAME/KEY: TATA_signal
<222> LOCATION: (432)...(437)

<400> SEQUENCE: 7

| | |
|---|---:|
| agtttggaat gtgttgtgtg tgatgtgatg gagagtatca gcattccaaa catgacatgg | 60 |
| ttttaactta tctgcaatgg tttctttttt attcagcgaa ctcgatggct gatgctgaga | 120 |
| gaaatgaatt gggaagtcga tcgacaatgg cagctcaact caatgatcct caggtataag | 180 |
| catttttttg gcagctctgg tcattgtgtc ttcaactttt agatgagagc aaatcaaatt | 240 |
| gactctaata ccggttatgt gatgagtgaa tcatttgctt ttagtagctt taatttatgc | 300 |
| ccccatctta gttgggtata aaggttcaga gtgcgaagat tacatctatt ttggttcttg | 360 |
| caggacacag ggattcatgc tagacacatc agcagtgttt ctacgttgga tagtggtatg | 420 |
| tacttagcta ctataaagga aattttgata gatatgtttg atatggtgct tgtacagatc | 480 |
| tatttaatgt caatgtattt gaaactatct tgtctcataa ctttcttgaa gaatacaatg | 540 |
| atgagactgg gaaccctatc tggaagaata gagtggagag ctggaaggac a | 591 |

<210> SEQ ID NO 8
<211> LENGTH: 480
<212> TYPE: DNA
<213> ORGANISM: Eucalyptus grandis
<220> FEATURE:
<221> NAME/KEY: 5'UTR
<222> LOCATION: (1)...(480)

<400> SEQUENCE: 8

| | |
|---|---:|
| atgctgagag aaatgaattg ggaagtcgat cgacaatggc agctcaactc aatgatcctc | 60 |
| aggtataagc attttttgg cagctctggt cattgtgtct tcaacttta gatgagagca | 120 |
| aatcaaattg actctaatac cagttatgtg atgagtgaat catttgcttt tagtagcttt | 180 |
| aatttatgcc cccatcttag ttgggtataa aggttcagag tgcgaagatt acatctattt | 240 |
| tggttcttgc aggacacagg gattcatgct agacacatca gcagtgtttc tacgttggat | 300 |
| agtggtatgt acttagctac tataaaggaa attttgatag atatgtttga tatggtgctt | 360 |
| gtacagatct atttaatgcc aatgtatttg aaactatctt gtctcataac tttcttgaag | 420 |
| aatacaatga tgagactggg aaccctatct ggaagaatag agtggagagc tggaaggaca | 480 |

<210> SEQ ID NO 9
<211> LENGTH: 308
<212> TYPE: DNA
<213> ORGANISM: Eucalyptus grandis
<220> FEATURE:
<221> NAME/KEY: 5'UTR
<222> LOCATION: (1)...(259)

-continued

```
<400> SEQUENCE: 9
gcccatctca ggtgcaacgg tttaactgat gtttactaca cgcaaggggg aggtatccgg     60
aaagcttgca aatcgggtaa aaacgaaaat gggcgacgtg gactcagcct gcccatgttt    120
tcggtctctc tcctggactt ccatgcccga taagggccgc caactctctc tctctctctc    180
tttttctctc acatctctct gcctgttcat gtcgcctgca agtgaagatt cgtcggagca    240
agaaggacga accgggcaca tggcggggtc ggcggtcgcg acggttctaa agggtctctt    300
cctggtgt                                                             308

<210> SEQ ID NO 10
<211> LENGTH: 300
<212> TYPE: DNA
<213> ORGANISM: Eucalyptus grandis
<220> FEATURE:
<221> NAME/KEY: 5'UTR
<222> LOCATION: (1)...(251)

<400> SEQUENCE: 10
gcccatctca ggtgcaacgg tttaactgat gtttactaca cgcaaggggg aggtatccgg     60
aaagcttgca aatcgggtaa aaacgaaaat gggcgacgtg gactcagcct gcccatgttt    120
tcggtccctc tcctggactt ccatgcccga taaaggccgc caactctctc tcttttctc    180 tcacatctct ctgcctgttc atgtcgcctg caagtgaaga ttcgtcggag caagaaggac    240
gaactgggca tggcggggtc ggcggtcgcg acggttctaa agggtctctt cctggtgt    300

<210> SEQ ID NO 11
<211> LENGTH: 297
<212> TYPE: DNA
<213> ORGANISM: Eucalyptus grandis

<400> SEQUENCE: 11
gtgcaacggt ttaactgatg tttactacac gcaaggggga ggtatccgga aagcttgcaa     60
atcgggtaaa aacgaaaatg ggcgacgtgg actcagcctg cccatgtttt cggtctctct    120
cctggacttc catgcccgat aagggccgcc aactctctct ctctctctct tttctctca    180 catctctctg cctgttcatg tcgcctgcaa gtgaagattc gtcggagcaa gaaggacgaa    240
ctgggcatat ggcggggtcg gcggtcgcga cggttctaaa gggtctcttc ctggtgt      297

<210> SEQ ID NO 12
<211> LENGTH: 661
<212> TYPE: DNA
<213> ORGANISM: Eucalyptus grandis

<400> SEQUENCE: 12
ctgagccatt taattcgaga gcacatcgcc caaaattatt cttcttgctg ccataactgt     60
cgaattttct cttttaggta agtaaccaat gatgcatcat gttgacaaaa aggctgatta    120
gtatgatctt ggagttgttg gtgcaaattt gcaagctgac gatggcccct cagggaaatt    180
aaggcgccaa cccagattgc aaagagcaca aagagcacga tccaacccttt ccttaacaag    240 atcatcacca gatcggccag taagggtaat attaatttaa caaatagctc ttgtaccggg    300
aactccgtat ttctctcact tccataaacc cctgattaat ttggtgggaa agcgacagcc    360
aacccacaaa aggtcagatg tcatcccacg agagagagag agagagagag agagagagag    420
agagttttct ctctatattc tggttcaccg gttggagtca atggcatgcg tgacgaatgt    480
acatattggt gtagggtcca atattttgcg ggagggttgg tgaaccgcaa agttcctata    540
tatcgaacct ccaccaccat acctcacttc aatccccacc atttatccgt tttatttcct    600
```

```
ctgctttcct tgctcgagt ctcgcggaag agagagaaga gaggagagga gagaatgggt    660
t                                                                  661

<210> SEQ ID NO 13
<211> LENGTH: 336
<212> TYPE: DNA
<213> ORGANISM: Pinus radiata

<400> SEQUENCE: 13
actagtgatt tgttgagaat gagtaggcat tgctacaccc atcatcacaa gcatcatcat     60
gaggagaaga agatccattt ctcactctat tactcgaact tccttcagat taggctgtgt    120
atttctcact ctaccactcc aacttccttc aaatgctgtg agttttttgtt gtaattgccc   180 cgtctattta taatcgcagc agcactcgtc atataaagac ccgtgtgtgt gaacaacaac   240
caagtgattt gaattggaaa tgaagagcga gaatggcggt gtcatgaccg ggagcaacca   300
gcccgggccg tcgaccacgc gtgccctata gtaatc                             336

<210> SEQ ID NO 14
<211> LENGTH: 763
<212> TYPE: DNA
<213> ORGANISM: Pinus radiata

<400> SEQUENCE: 14
actagtgatt tgttgagaat gagtaggcat tgctacaccc atcatcacaa gcatcaacat     60
gaagagaaga agacgatcca tttctcactc tatcactcca acttccttca gattaggctg    120
tgtatttctc actctaccac tccaactacc actccaactt attgccgcaa agagagagg    180 ttcccaaact ctgtcggaat ctcccactc aaagcattaa aggaaagatc taattgctgc    240
aaaaaagaga gattcccaat atatttctca actcccttca aatgatttct cactctacca   300
ctccaactcc cttcaaatga tttctcactc taccactcca acttccttca aatgctgtga   360 gttttttgttg taattgcccc gtctatttat aatcgcagca gcactcgtca tataaagacc   420
cgtgcgtgtg aacaacaatg gcggtgtctt gactgggagc aaccgcataa agaaagtggg   480
cttcatacat taaaaaaatc tgtaaatttt acggatttgg aaaaaggaag agcaggaggg   540
acctcccgac ttgacccgag aatggcggtg tcttgaccgc gtaaagaaag tggtcttctg   600
tacccgactt gacccgaaaa aagaggaaac gttgaacgag acaatctctg ggaacttcat   660
cgaaatgaac ctcacgactt gactctttcg attgtactgt tttcattgtt cccgcgtaaa   720
acgaccagcc cgggccgtcg accacgcgtg ccctatagta atc                     763

<210> SEQ ID NO 15
<211> LENGTH: 40
<212> TYPE: DNA
<213> ORGANISM: Artificial Sequence
<220> FEATURE:
<223> OTHER INFORMATION: Made in a lab

<400> SEQUENCE: 15
acggataaca gagtctttat attaaacgaa atggtattgc                           40

<210> SEQ ID NO 16
<211> LENGTH: 51
<212> TYPE: DNA
<213> ORGANISM: Artificial Sequence
<220> FEATURE:
<223> OTHER INFORMATION: Made in a lab

<400> SEQUENCE: 16
```

```
tgacgcggcc gcgaccgacg aaaagaaaaa tataacataa gagagtctga a              51
```

<210> SEQ ID NO 17
<211> LENGTH: 27
<212> TYPE: DNA
<213> ORGANISM: Artificial Sequence
<220> FEATURE:
<223> OTHER INFORMATION: Made in a lab

<400> SEQUENCE: 17

```
tatagcggcc gcgggggggg ggggggg                                         27
```

<210> SEQ ID NO 18
<211> LENGTH: 30
<212> TYPE: DNA
<213> ORGANISM: Artificial Sequence
<220> FEATURE:
<223> OTHER INFORMATION: Made in a lab

<400> SEQUENCE: 18

```
cggagaacaa ggtggagggt agattctttc                                      30
```

<210> SEQ ID NO 19
<211> LENGTH: 31
<212> TYPE: DNA
<213> ORGANISM: Artificial Sequence
<220> FEATURE:
<223> OTHER INFORMATION: Made in a lab

<400> SEQUENCE: 19

```
tctgcatctt gaaattgaaa tatgactaac g                                    31
```

<210> SEQ ID NO 20
<211> LENGTH: 363
<212> TYPE: DNA
<213> ORGANISM: Eucalyptus grandis

<400> SEQUENCE: 20

```
aatcgggtga aaatagggcc gccctaaatt agaattgaca acatttcttg ggcaaagtta     60
atgtaagtta catgaaaaaa aaaaaaaagg atagtttgtt ggaagtaatg gagcattgt    120
attgtgaaat tcacgataga gctaacaaaa ataaaggtag ttggtgggtt aacccagtta   180
aaaagaaca ataatttgaa gagaggagag agagagagag gaggggggaga gcatttcgat    240
aaattcacta gaaaaaatgc gtgttttagt ataaatgaga gtggaaatag gccatctag    300
ggaacgatcg atcgcccctg cacccggcca tctggagagt ctgtttatac ttctctccgg   360
ctt                                                                 363
```

<210> SEQ ID NO 21
<211> LENGTH: 839
<212> TYPE: DNA
<213> ORGANISM: Pinus radiata
<220> FEATURE:
<221> NAME/KEY: misc_feature
<222> LOCATION: (1)...(839)
<223> OTHER INFORMATION: n = A,T,C or G

<400> SEQUENCE: 21

```
gtatggagtt ttgaagggct ttactcttaa catttgtttt tctttgtaaa ttgttaatgg    60
tggtttctgt gggggaagaa tcttttgcca ggtccttttg ggtttcgcat gtttatttgg  120
gttattttc tcgactatgg ctgacattac tagggctttc gtgctttcat ctgtgttttc   180
ttcccttaat aggtctgtct ctctggaata tttaattttc gtatgtaagt tatgagtagt  240
```

```
cgctgtttgt aataggctct tgtctgtaaa ggtttcagca ggtgtttgcg ttttattgcg      300
tcatgtgttt cagaaggcct tgcagatta ttgcgttgta ctttaatatt ttgtctccaa      360
ccttgttata gtttccctcc tttgatctca caggaaccct ttcttctttg agcatttct      420 tgtggcgttc tgtagtaata ttttaatttt gggcccgggt tctgagggta ggtgattatt      480
cncagtgatg tgcttttccct ataaggtcct ctatgtgtaa gctgttaggg tttgtgcgtt     540
actattgaca tgtcacatgt cacatatttt cttcctctta tccttcgaac tgatggttct      600
ttttctaatt cgtggattgc tggtgccata ttttatttct attgcaactg tattttaggg      660
tgtctctttc tttttgattt cttgttaata tttgtgttca ggttgtaact atgggttgct      720
agggtgtctg ccctcttctt ttgtgcttct ttcgcagaat ctgtccgttg gtctgtatt     780 gggtgatgaa ttatttattc cttgaagtat ctgtctaatt agcttgtgat gatgtgcag      839

<210> SEQ ID NO 22
<211> LENGTH: 881
<212> TYPE: DNA
<213> ORGANISM: Eucalyptus grandis

<400> SEQUENCE: 22
acgtgacgat gctcgagtct cgcgttctcc tctctcttgt tctgcaaaac agaaaagaga       60
gaatggaggt tggcctctct caattacgtg gacgccaatg agataactca ggtgggcgac      120
aaaacaaacg cctcttgatt tcctcaaacc ccaaaccgaa tccctcgtca aggggcaagg      180
cttttggtcc cgcggcccca cggatcgctc gttcccgtct cgccacgtcg cgtcgcagcg      240
tgtcgagcaa acagaggggt ccgagcgact ataaaatccc gacgccatcg acaccacagt      300
ccatcgaaaa ccttgttcaa ttcccaagtg aaagtgagta actgtgaacg aagagttgaa      360 cttttgcatct cggcgtgtgg attcaagagg aagcagcaaa gtggaaatgg acaactccaa      420
gatgggcttc aatgcaggggc aggccaaggg ccagactcag gagaagagca accagatgat     480
ggataaggca tccaacactg ctcaatctgc aagggattcc atgcaagaga ctggtcagca      540
gatgaaggcc aaagcccagg gtgctgctga tgcagtgaag aatgccaccg ggatgaacaa      600
atgaagagct caagacatga atgaataaat aattaagctc tggttatcat ttgctttttcc      660 ggtcgtttgt tgtcctgttt ttccttgtca agagcttatt atgagggtcc ttttgctctt      720
tccttagttc ttttttgtttc ttggttgttc catgaagaga gcaactctct gtgtttgaga      780
gtactcatct cgcttcataa ggtctcagta tgtagttgcc tttcgagaat gttatgttct      840
ctctcataat gctattctga tttttataaa aaaaaaaaaa a                           881

<210> SEQ ID NO 23
<211> LENGTH: 350
<212> TYPE: DNA
<213> ORGANISM: Eucalyptus grandis

<400> SEQUENCE: 23
ctatagggca cgcgtggtcg acggcccggg ctggtccttt cttacaaaaa gcaaaattct       60 tataatttt tttgatataa taaaaatgat ccataaactt tgcttaatg tgcaacgtaa       120 accataatat attcaacgtg atgcttaaac tttaatcgag tatgcaatgt agtccataat      180
atattcaata tgatccttca atccaattga agtgtgcaat gtggtcgcta gatttttta       240 tgtattcaac ttagtcttta agctaccaac cttccaataa tttatgtttt agaaataata      300
tcgaacatct tttatattat tcaaggaata aaacgaacat gcatcaaaag                 350
```

<210> SEQ ID NO 24
<211> LENGTH: 49
<212> TYPE: DNA
<213> ORGANISM: Eucalyptus grandis

<400> SEQUENCE: 24
actatagggc acgcgtggtc gacggcccgg gctggtactt tttttttct            49

<210> SEQ ID NO 25
<211> LENGTH: 909
<212> TYPE: DNA
<213> ORGANISM: Eucalyptus grandis

<400> SEQUENCE: 25
cagggtaaag aaaatggaat atttgcttgg ccccccagct ttgaaagttg ctgtaagaac      60
acactcacct tgcatttata cgatggttgt gagcagtgca ggctggtggt gctgcaaatt     120
tatgatgctg atgtgatagg cagatgaatg gcagttgagc taagttaaag ccctcataca     180
tagatcagag caggaggagt agtatatata ggcatcttgg caagtcccta aaagagcggc     240
ttcgtgtatt cccacatatt cctctctcgt tagaacgttc agaaatgggt ggccctttga     300
ctcttgatgc agaggttgag gttaagtctc ctgcagacaa gttctgggtg agcgtgagag     360
actccaccaa actgttccca aagatcttcc cggaccagta caagaatatt gaagtccttg     420
agggagatgg gaaggctcct ggctcagttc gcctcttcac gtatggtgaa ggttctccac     480
ttgttaaagt atcaaaggag aagattgatg gtgtggacga agcagacaag gtcgtgacct     540
acagcgttat agacggtgat ctcctgaagt actacaagaa tttcaatggc agcatcaagg     600
taattcctaa aggagacgga agcttggtga atggtcgtg tgggtttgag aaggcaagcg     660
atgaaattcc tgatccccac gtaatcaagg acttcgcaat ccagaatttc aaagagcttg     720
atgagttcat cctcaaggca tagatgccgc caatcgtcta tccggatttg cactaaatat     780
caataaaata atgcggagct ggactccgca cttctatatg catctagtat gagagtcccc     840
tgctgtctct gtttgtattc acttgaaggg ttttctatta agctctcttt actgcctccg     900
aaaaaaaaa                                                                 909

<210> SEQ ID NO 26
<211> LENGTH: 430
<212> TYPE: DNA
<213> ORGANISM: Eucalyptus grandis

<400> SEQUENCE: 26
tggagcttga gatagatcga ccgagagatc ccagcggaaa tagaagattt cctgatacca      60
tcgatccttc ttctccaatg gctgcgaatt tcgtcattcc gaccaaaatg aaggcttggg     120
tgtaccgtga gcacggaaac gtcgccgacg tattgggatt ggacccggaa ctcaaggtcc     180
ctgaattgca agaaggccaa gtgctggtta agttcttgc cgcagcgctc aatccagtcg     240
acgccgcgag aatgaagggg gttatcaagc tcccgggctt ttctctaccg gccgtgccag     300
gttacgatct cgccggcgtt gtggtaaagg tgggccgcga agtgaaggag ctcaagatcg     360
gggacgaggt atatggattt atgtttcacg ccaagaaaga cgggacgctg gctgagtacg     420
cagccgtgga                                                                430

<210> SEQ ID NO 27
<211> LENGTH: 1253
<212> TYPE: DNA
<213> ORGANISM: Eucalyptus grandis

<400> SEQUENCE: 27

```
gcttgagata gatcgactga gagatcctag tggaaataga agatttcctg ataccatcga      60
tccattcttc tccaatggct gcgaatttcg tcattccaac caaaatgaag gcttgggtgt     120
accgtgagca cggagacgtc gccaacgtat tgggattgga cccggaactc aaggtccctg     180
aattgcaaga aggccaagtg ctggttaaag ttcttgccgc ggcgctcaat ccaatcgaca     240
ccgcgagagt gaaggggggtt atcaagctcc cgggcttttc tctaccggcc gtgccaggtt     300
acgatctcgc cggcgttgtg gtgaaggtgg gccgcgaagt gaaggagctc aaggtcgggg     360
acgaggtata tggatttatg tttcacgcca agaaagacgg gacgcggct gagtacgcag     420 ccgtggaaga gtcgttcttg gctttgaagc ccaagaagct gcgtttcggg gaggctgctt     480
ctctgccggt ggtcattcag accgcctatg gaggccttga agagctggc ctctctcatg     540 gcaagtccct cctcgtctta ggtggtgctg gtggcgtcgg cacactcata atacagctag     600
ctaaggaagt ttttggtgca tcaagagtag cagctacatc cagcactggg aagctagagt     660
tgttgaagag cttgggtgct gatctggcca ttgactacac caaagtcaac tttgaagacc     720
tcccagaaaa gtttgatgtt gtctacgata cagttgggga aattgagcgg gcagcgaagg     780
ctgtgaagcc aggagggagc atcgtgacga tcgtaaaaca aaacaagaca ttaccccgc     840 ctgctttctt ttttgcagta acttcgaacc gttcgacctt ggagaagttg aagcccttct     900
tggagagcgg gaaggtgaag ccggtgatcg accccaagag cccgttccca ttttcgcaag     960
ccattgaggc cttctcgtat cttcaaaccc gccgggcaac tggaaaactc gtgattcacc    1020
ccgtcccatg atacacaaac gagaaagaaa taaagcgtcc acatggatct gccttaatca    1080
cgagtcctta attagtagtc gatggtgctt gctgtttgtc tccgtacatt cagcttctct    1140
ttgcatagta gtttctacat agtgcgtgta gagaagcaag tggatgtaca agtaaaataa    1200 ttacttttc tataaacaat attacaaact caaaaaaaa aaaaaaaaa aaa               1253

<210> SEQ ID NO 28
<211> LENGTH: 99
<212> TYPE: DNA
<213> ORGANISM: Eucalyptus grandis

<400> SEQUENCE: 28
gatagatcga ccgagagatc ccagcggaaa tagaagattt cctgatacca tcgatccatt      60
cttctccaat ggctgcgaat tcgtcattc cgaccaaaa                              99

<210> SEQ ID NO 29
<211> LENGTH: 927
<212> TYPE: DNA
<213> ORGANISM: Eucalyptus grandis

<400> SEQUENCE: 29
cgacgtcgca tgctcccggc cgccatgcgg ccgcgggaat tcgattacta tagggcacgc      60
gtggtcgacg gcccgggctg gtactctcac taattcttta gttttccaat ttagcccctt     120
ctgtaattgc tcatcttctt taccaaattc tctaatttgg ccggcgaagg gctgacaagg     180
gattggtcat gtcaccctca ccaaaggttg ccgaaggtcc ggtgacctca gctgacggcc     240
acctacacca aatctagctc actagcagcc taagcccttc atcaactcta gtgaaaggtt     300
ttgagtattt tttaataaaa aatatttaaa aaatatatag cgagagctca ttacaaaaaa     360 atttttaaaaa aaaatctaaa cattacttga actcaaagtg actttataaa gagttttac     420 caaaggatct tggtttcatc atttgcacta cacccaaaac ccaatttcta agttaaatca     480
aacccactgt ctaatagaga taaggtaaat gttataaacc aaattccaaa attccgaagc     540
```

```
actaaatata tttgctgatc ttataatcgc caattgagag ggtctcattc tccaagggat    600
tgtgacatat tagtaattga tagggtctca tccgtaggac tccgactcag ccgcgccacg    660
tgactggatc gctgaacggc gcggaaccag aggagcgtga ttacctaata ttttctccta    720
ccttggcctt gagattgaat tcagaaaaa gaaaagaaa aggaacaac ttcgccgact       780 gttctataaa atgcatgcgc caccccgacc cccacccacg catcacatcc atccagcctc    840
cacgacagac gcataaacac aacacacgtc ggttagagag agagagagag agagagagag    900
agagagagag atgcttggac agttgtc                                       927

<210> SEQ ID NO 30
<211> LENGTH: 411
<212> TYPE: DNA
<213> ORGANISM: Eucalyptus grandis

<400> SEQUENCE: 30
actatagggc acgcgtggtc gacggcccgg gctggtctga aactgtcgct cggcgatgca     60
taccaaaggc tgaaggtatc agaatctaat gcagcttatg taaaagcgcg atcaatttat    120
tgaccccgac gaccttgact ccatacttca cgcctcagct ttgtgttgga tggtcttgac    180
ctctctcacc ctaaaaggta gctcaaaaga atgagacttt ccgtcatact tataaaccga    240
ccaccagcct ctttcacaac cgacatggga caacctcaaa tagaattttt aacaacaccc    300
ttgcacgctc tttctatcca ctttattatg ccatcacatg agcgttttcc acgcgtaaat    360
cggctaccac ccactttcac acggcggcga acgagaaaa aggtcctacc t              411

<210> SEQ ID NO 31
<211> LENGTH: 178
<212> TYPE: DNA
<213> ORGANISM: Eucalyptus grandis

<400> SEQUENCE: 31
cgagtcagca gaaacccagt tacactccgc ccaaacggaa gctaaacctg atgggccata     60
cgatttcttt cactgagcct cttgcttttc ctccggaatc tcacggcacc ggaatgccgg    120
aggaacttgg gaagaaccaa tgatgcctgg tcactgagtg atcgatgaat gcaatagt     178

<210> SEQ ID NO 32
<211> LENGTH: 178
<212> TYPE: DNA
<213> ORGANISM: Eucalyptus grandis

<400> SEQUENCE: 32
gtccaatgtc ctgtcaaagg aggaaagatg actatggccc cggcgccggc ggggactgca     60
tgggatttag tatgttgatt gagtacccgt cgccaccacc ttcaagtaaa tcaggagtca    120
gcagaaaccc agtacactcg ccaaacggag ctaaacctga tggccatacg atttcttt     178

<210> SEQ ID NO 33
<211> LENGTH: 178
<212> TYPE: DNA
<213> ORGANISM: Eucalyptus grandis

<400> SEQUENCE: 33
gcatgggatt tagtatgttg attgagtacc cgtcgccacc accttcaagt aaatcaggag     60
tcagcagaaa cccagtacac tcgccaaacg gagctaaacc tgatggccat acgatttctt    120
tcactgagcc tcttgctttt cctccggaat ctcacggcac cggaatgccg gaggcaac     178
```

<210> SEQ ID NO 34
<211> LENGTH: 1274
<212> TYPE: DNA
<213> ORGANISM: Eucalyptus grandis

<400> SEQUENCE: 34

| | | | | | |
|---|---|---|---|---|---|
| ctatagggca | cgcgtggtcg | acggcccggg | ctggtccttt | cttacaaaaa | gcaaaattct | 60 |
| tataatttt | tttgatataa | taaaaatgat | ccataaactt | ttgcttaatg | tgcaacgtaa | 120 |
| accataatat | attcaacgtg | atgcttaaac | tttaatcgag | tatgcaatgt | agtccataat | 180 |
| atattcaata | tgatccttca | attttaattg | aatgtgcaat | gtggtcgcta | gatttttta | 240 |
| tgtattcaac | ttagtcttta | agctaccaac | cttccaataa | tttatgttta | gaaataatat | 300 |
| cgaacatctt | ttatattatt | caaggaataa | aacgaacatg | catcaaaagt | ttaaatatat | 360 |
| caaataaaat | aaaattttaa | gaattatatt | acatattaaa | attaaagttc | atgattaaat | 420 |
| tgaaataaaa | taaaaattta | aaaatcacgt | tgtatgttgt | gccgaaacaa | aattcagtga | 480 |
| cttgtggtgt | caattttctt | aggtggagct | ccacaagcat | tgagatggag | tgttccttcc | 540 |
| gccgaggttt | tcattgcgtg | gctcaaaacg | gtggcgcgtt | ttgcacgaca | cgagatgcct | 600 |
| cgattgccgc | atcgtgtagg | cgacgcaacg | gaaaaacgcg | ttgccgtggc | gtctatccgg | 660 |
| ggtttcgtct | ccgatgcggc | acgtagccta | taaatgcgca | cgatctcccg | gtctgccaat | 720 |
| tcgctatcga | ttgcagaaga | aaactcaaac | cctaggcgct | ctctctccgt | tcgacctctc | 780 |
| gaagttctcc | tctcttcgcg | tcaagatgca | aatctttgtg | aaaaccctta | ctggcaagac | 840 |
| aatcaccctc | gaggtggaaa | gctcggacac | agtcgataat | gtgaaagcaa | aaatccagga | 900 |
| caaggaaggg | atccctccgg | accagcagag | gcttatcttt | gctggcaagc | agctggaaga | 960 |
| tggccgaacc | ttggccgatt | ataacattca | gaaggagtcc | accctccact | tggtgctccg | 1020 |
| tctcagggga | ggcatgcaaa | ttttttgtgaa | gactcttact | ggcaagacaa | tcaccctcga | 1080 |
| ggtggaaagc | tccgacacag | ttgataatgt | gaaagcaaaa | atccaggaca | aggaagggat | 1140 |
| ccctccggac | cagcagaggc | ttatctttgc | tggcaagcag | ctggaagatg | gccgaacctt | 1200 |
| ggccgattat | aacattcaga | aggagtccac | cctccacttg | gtgctccgtc | tcaagggagg | 1260 |
| catgcaaatc | tttg | | | | | 1274 |

<210> SEQ ID NO 35
<211> LENGTH: 795
<212> TYPE: DNA
<213> ORGANISM: Eucalyptus grandis

<400> SEQUENCE: 35

| | | | | | |
|---|---|---|---|---|---|
| aaaaatacag | gctttcgaaa | gctagtgcgg | tataaataac | ctgggaaaag | caagccgctt | 60 |
| gagctttagt | ttcagtcagc | catggccact | cacgcagctc | ttgctccctc | aaccctcccc | 120 |
| gccaatgcca | agttctctag | caagagctcc | tctcactcct | tccccactca | atgcttctct | 180 |
| aagaggctcg | aggtggcgga | attctcaggc | cttcgtgctg | gatcgtgtgt | gacttatgcg | 240 |
| aagaatgccg | ggagggatc | cttcttcgat | gctgtggctg | ctcagctcac | tcccaagact | 300 |
| tcagcaccag | ctccagctaa | gggagagact | gtcgctaaac | tgaaggtggc | aatcaatggt | 360 |
| ttcggtcgca | ttggtcggaa | cttccttaga | tgctggcacg | ggagaaagaa | ctcgcccctt | 420 |
| gatgtcattg | ttgtcaatga | cagcggtggt | gtcaaaaatg | cttcacattt | gctgaagtat | 480 |
| gattccatgc | tggggacttt | caaagctgat | gtgaaaattg | tggacaatga | gaccatcagc | 540 |
| gtcgatggga | agcccgttaa | ggtcgtctct | aaccggacc | ctctcaagct | ccctggggct | 600 |
| gagctcggca | tcgacattgt | cattgaggga | actggagtct | tcgtggatgg | ccctggtgct | 660 |

-continued

| | |
|---|---|
| ggaaaacata ttcaagctgg tgccaagaaa gttatcatca ctgcaccagc aaaaggcgct | 720 |
| gatataccca cctacgtcta tggtgtgaat gagacagatt attcgcatga agttgctaac | 780 |
| ataatcagca atgct | 795 |

<210> SEQ ID NO 36
<211> LENGTH: 1200
<212> TYPE: DNA
<213> ORGANISM: Eucalyptus grandis

<400> SEQUENCE: 36

| | |
|---|---|
| aaaatatcca tcgacagcat cacccccgctt agagaacggt gtctcggctt ctcacaatgt | 60 |
| ctatagccga atgtacaaaa tcggcataat gttctataat atagcggact ttacagatga | 120 |
| gcattcaaat acgtacgccg tactcgattc ccattcgatt gttcattcat ccgcatgcaa | 180 |
| atttcataga gataatatct gtgcacgtcc ttagattaag aacaaccaaa gagtatctgg | 240 |
| tggaagtttg aagcatgacc accgaagtca gatggaacaa acaaggtggg tggtggggat | 300 |
| atagtggaca aaggaacgag aggtgaatag gaaaaggaga aggcaagatg cgggagatag | 360 |
| gatttacgtg gcgagcggcg attgcacgca tggtccaccc caccctcaac ctcaaacttt | 420 |
| cgaaaatgca acgggcatca gggtggcgat gaaggagacg atggagatat tgttgctttc | 480 |
| tcccccaaa aaacatcatc caatccatcc ccattcctca tcttcaccac aaggagtctg | 540 |
| aagctctcct tcaccggtcc gtcgctttct ctcttatctt cttcttctcc ctcctcttct | 600 |
| cgttcttcct tcgaccgttc tctcggtatc gtgaatttat tgcggggtgg ttcgcatgct | 660 |
| ataaattcca cagcaacgag ggccccttgc cacaatgtcg acgtctccgg ttagcagctg | 720 |
| gtgcgccacc tccttctccc ctgcccattc ctcgctcaag agagccgccg gcctacggcc | 780 |
| ctctctctcc gcccgcctcg gcccttcctc ctcctcctcc tccgtctctc ctccgaccct | 840 |
| catccgtaac gagcccgttt cgccgccccc gccccctgtc atcaaccca cttggacaga | 900 |
| agagatgggc aaggactatg acgaggccat tgaggctctc aagaaactcc tcagtgagaa | 960 |
| gggggacctg aaagccacag cagccgcaaa agtggagcaa ataactgcgg agttgcaaac | 1020 |
| tgcttcccca gacatcaagc catccagctc cgttgacaga atcaaaactg gcttcacctt | 1080 |
| cttcaagaag gagaaatacg acaagaaccc tgctttatat ggtgaactgg caaagcagag | 1140 |
| tccaaagttc atggtgtttg cttgctcgga ctcgagagtg tgcccatctc atgtgctgga | 1200 |

<210> SEQ ID NO 37
<211> LENGTH: 648
<212> TYPE: DNA
<213> ORGANISM: Eucalyptus grandis

<400> SEQUENCE: 37

| | |
|---|---|
| cgacggactc ctttcacgat atcgaaacga ggaaacggag gagaagcaga agaaagaaga | 60 |
| tgaagaaagg cagatggttg gtgatggatg aaactgtcgg gaagctggga gcttcaggga | 120 |
| gttctatttta tggggcgaaa caggggaggg gaaaccgaat ttaccaagat gcccttcttg | 180 |
| gtgggattgg acatggagct gcacgaccgt cgtcccatca cgaagagtct tgctcttcgg | 240 |
| tacacatgca atcgtcggcg aaccgacctt atccgaccgg ttccaagctt gtcctggtaa | 300 |
| aaggtttcga accttggaaa aggcttaaga gatgtatcgt tgccttaacc attattccat | 360 |
| gttcacataa tatttggccc ggttttcagg tcaattttgg agtagcccgg ttcggttcta | 420 |
| gtcccgctcc cgattcaaaa attcattggg aacaaatttt gacactgtct ggtatttttg | 480 |
| gtctaagacc ctacccaatt ttagaactgt acacccttgc tttatcccaa aataaaattg | 540 |

```
tcaattagtc aactttttcac acttgatgat cgattaagta gatggatgac atggtctttt      600
accagcccgg gccgtcgacc acgcgtgccc tatagtgagt cgtattac                    648

<210> SEQ ID NO 38
<211> LENGTH: 288
<212> TYPE: DNA
<213> ORGANISM: Eucalyptus grandis

<400> SEQUENCE: 38
gattgtaata cgactcacta tagggcacgc gtggtcgacg gcccgggctg gtatcgtgaa       60
agaagtccgt cgacgacaat ggccgagaag agcaaggtcc tgatcatcgg agagaagagc      120
aaggtcctga tcatcggaga gaagagcaag gtcctgatca tcggagagaa gagcagggtc      180
cttatcatcg gagaatcgaa ttcccgcggc cgccatggcg gccgggagca tgcgacgtcg      240
ggcccaattc gccctatagt gagtcgtatt acaattcact ggccgtcg                   288

<210> SEQ ID NO 39
<211> LENGTH: 382
<212> TYPE: DNA
<213> ORGANISM: Eucalyptus grandis

<400> SEQUENCE: 39
acagcaatct catctgatga ttcttcagtt cggagctcag aggatacatc atctatagct       60
gaattgagct gtgcaatctt ctcggcaagc accttcctcg ttttctgaaa atcatcagat      120
tttaaggtga atccatattt cgcagatggc catgttactg ctacactctc ttcacagcat      180
acatgaagga ggtcacatag caagcataca taggacctca tatacaaata tgacagcaga      240
ccagcccggg ccgtcgacca cgcgtgccct atagtagtag tggggaagga gtgagaggag      300
ctcttgatga ggaatgtcgg cttttcttcc atcagttgat gttccgggtt cctagtcatt      360
atgccgatgg tggccactcc ag                                               382

<210> SEQ ID NO 40
<211> LENGTH: 986
<212> TYPE: DNA
<213> ORGANISM: Eucalyptus grandis

<400> SEQUENCE: 40
aaatacaaac tggtttaata ttcaactcag ataattacat gacaccacct aaataatgga       60
aagtcaagca aatagacata ttatccccac acataatcaa ctatattcat gactggagag      120
gtgctagatg gtatagagtc cctagttatt atttattttt ttgggcccga aagatcctg       180 atggatctat gctgtttgat actttcgat ttgttttgtc tacagctcaa ataaattagt       240
gcttgggttt tgatatatta tctaatctga tacaagtctt tgtcctggcc aattttttgca     300 gagtttcctg caaaacagtg cactaaagct tccagaggac ctcatgccat gcccaagggc      360
accacctatg atggaacgga gaatcaaacc acagactgaa caggcgttga aatgccccag      420
atgtgattct acaaacacaa aattctgtta ctataacaac tacaatcttt cacaacctcg      480
ccatttctgc aagacctgca ggcgatactg gaccaaagga ggtgccttac gtaacgttcc      540
tgttggtggg ggttgcagaa agaataaacg agccaagcga gcagtagacc atcctgtctc      600
tgctcagaat gaagcatcca cctctgcagc cccaggcaac gaagtacctg accggtctcc      660
ctttgagcca ccatcttcaa aatccatttta ctatggggga gaaaacatga acttaaccgg    720 tctcccctttt agcagaattc agcaggaccg agctgcattg gccactgca actcttcttc    780 cttttctagga atgtcatgtg gcacccaatc ggcctctctg gaaccacatc tttcggcttt    840
```

```
aaatacattt aattcattca agtctaacaa tcctggtctg gattttccta gcttaagcac    900
agaccagaat tcactgtttg agaccagcca gccacaactg tcaagagcaa tggcatctgc    960
cctttttcct atgccaatgg ctcctg                                         986
```

<210> SEQ ID NO 41
<211> LENGTH: 313
<212> TYPE: DNA
<213> ORGANISM: Pinus radiata

<400> SEQUENCE: 41

```
aaaggaaaat tcaaagatct ttagccaatt tttgttgttg tgaccttgaa tttctaaaaa     60
atttaatgga ttcgttttct aaattcctga ttcgtcaaag gctgaagggc acgatagtaa    120
tagaaaatgg acggcagttt atcctttcat ggctggacac acagaatttg tggagggact    180
ctccattctg gtttatccgc cgttagttct ctctgtactc caccctttagt tctctttgta    240 ctcgagacct ttaatgatta gccctgctta tgctgtcatt actgaactca cttccagagc    300
cccaaaaatc tct                                                       313
```

<210> SEQ ID NO 42
<211> LENGTH: 713
<212> TYPE: DNA
<213> ORGANISM: Pinus radiata

<400> SEQUENCE: 42

```
taattcacaa gtagaaaatg agattttttgc aattttgtaa ctaacatttc ccggtctcct    60
ctgtatgttt tcacccctta atgtaattga aatttgcacc cgggttagat tcaaagcgga   120
gaataacatc ggggccttgt tctagacaga gattttttcac aaataacagg ttcgaaggta   180
tgtgtagaca tctgggtagt tgtagaataa agacggagcc cattaggtga tccaatcgaa   240
gagctcagat gggaaaacag ataaaaatta tcgggtggac cttccttcac atgttaatta   300
tatatcaagt gtcgccaatc cttatgtgaa acatttagta aagcttcgcc agagcacttc   360
ttataggcat tctgtgggct ctgttgttgt ggttggaagt actcctttaa gggaggtatc   420
tgaatatttg caacagaagt cagttaaaca agtggttgac tgtctgtttg tacaagatgt   480
tactggcata cctgtgggct tgatagagac ttccaggcgc attgtgcatg taaatcattt   540
ggtgatgcag aagctagccg gagtagagtc tatagagccc actgaagcaa ttggtgtaat   600
caagcttcct agcagcttct acaacttgga atctcttgaa attcactcta gttcccagat   660
atggtgctcg tcgccacatc gtctgcttgt acttgatggc attcaggatc ctg          713
```

<210> SEQ ID NO 43
<211> LENGTH: 28
<212> TYPE: DNA
<213> ORGANISM: Pinus radiata

<400> SEQUENCE: 43

```
ccacctcaca tcaataaatt ttatacga                                        28
```

<210> SEQ ID NO 44
<211> LENGTH: 35
<212> TYPE: DNA
<213> ORGANISM: Pinus radiata

<400> SEQUENCE: 44

```
gctgtttcat tggggtcata gctacgtggt gctga                                35
```

```
<210> SEQ ID NO 45
<211> LENGTH: 1729
<212> TYPE: DNA
<213> ORGANISM: Pinus radiata

<400> SEQUENCE: 45
cttattgaca tataaaagca aagttggatc catctgttat tttgggtccc ctccagaagc      60
cttactaaat gcggacaaaa aatccacgta aagaacttct gaatttaccg tcatctgggc     120
tctgtaatta cgaatttagg gtttcctctg tcaatatctg gtagtgacaa acaaggttta     180
atggcagcct tagcaacaac tgaagtttgt gatacatatc cacgccttgt ggagaatggt     240
gagcttcgtg tcttgcaacc aattttccag atatatggtc gacgtcgagc tttctctgga     300
cctatagtta cactgaaggt ctttgaggac aatgtccttt tgcgggaatt ccttgaggag     360
agaggtaatg gaagagtttt ggtagttgat ggaggaggaa gccttagatg tgccatactg     420
gggggcaatg tagttgtatc tgcccaaaac aatggttggt ctggaataat tgtcactggc     480
tgcataaggg acgttgatga aataaacaga tgtgacattg gtataagagc actgacatct     540
aacccactga aggccaacaa gaagggtgtg ggtgaaaaac atgcgcctat ttacattgct     600
ggtacccgca ttcttccggg ggaatggtgt tatgctgaca gtgatggtat tcttgtttca     660
cagcaagagt tatcactgtg agataataaa attcataagt ttcagattgt gactttcatg     720
tcctgtggaa catatatttg actcgagtta gattctaata ggattaattg atagattctg     780
aaaattgagg aatatctctg gtcatgaaaa tcttcttctc atgtgatctt ttatgctcag     840
ctttgagtac aggatgataa gaagtttgtg catgtttgtc taaaggttta gcaagtatta     900
tcggaccatc ataagagata gattatggaa ctcagggact tgctattttt aatccaaaat     960
aacatttatt ctttgtgttt ttgccaaatt aactttatt tccttggca ccactagtga    1020 tttgcaatat ccagttgctg agaacataga agtgggcaac ggtgagagtt gcaacagtat    1080
ctagcataga tttaacaagt attgttggat cattataaga aaataaacta cagaaccaag    1140
ggaatctagt tgacaacata gttaaagtag gcatggtgct actgtatcga tacatcttca    1200
taaacagaaa aatatgaaca agctctaatg atgggagaaa ctccagcttg gtgttttgat    1260
taagcatcca tattcacacc taaaaggtta caagttccaa aataaaaatt ccaatgaatt    1320
tagccaatct aatcagacct tataagaaat acactaggca tctggggatc aaaatccagt    1380
agtttagaaa gtagttgtaa ataacccaga gacaaaaatc tcaatgatag cttgcttggg    1440
tcataggttt gataataatt gaaaacatag ttgaaaggag aatcctagca atggctagct    1500
tgaataatag atgtacagca aaattacagt agttgagaac aaagatggaa ggataatccc    1560
aacgatagct agcttggaca gtaggatgat tacatcaaaa tcatagcagt tgagaacata    1620
gttggaagga gaatccttat gatggctacg ttggataata ggcgtgatta tcgtaggtag    1680
attagagcac aagatcaaac taatagctgg cgcagctatc gactatttt                1729

<210> SEQ ID NO 46
<211> LENGTH: 1038
<212> TYPE: DNA
<213> ORGANISM: Pinus radiata

<400> SEQUENCE: 46
tgattactat agggcacgcg tggtcgacgg cccgggctgg taaatgagaa catgataagc      60
tgtgtaaatt catgctagtc accataactt ttctcattgc ttttcatcca cactgttgat     120
tcattcatta tataagatca gattcgtatg atatacaggc aaccatagaa acaaccagca     180
aagttactag caggaaatcc aactaggtat catgaagact accaacgcag gctcgataat     240
```

```
gttggtgctc attattttg ggtgctgttt cattggggtc atagctacat cttttgattt      300
ctattacttc gttcaacagt ggcctggttc atactgcgat actcgtagag gatgctgtta      360
ccctcgcacg ggaaggcctg cttccgaatt ttccattcat ggcctctggc ccaactacaa      420
gaccggtaaa tggccacagt tctgtggttc ctccgaagaa ttcgactact caaagatctc      480
agatctggag gaggagctga acaggtattg gggttcgtta agctgtccaa gcagcgatgg      540
acaggaattt tggggacacg agtgggagaa acatggcact tgctctctca atcttgatga      600
gcattcatac tttgagaagg ctctctcctt gagacaaaat atagacattc ttggggctct      660
taaaactgca ggtattaaac ccgatggaag ccaatacagt ttgagcgata tcaaggaagc      720
cattaaacaa aacactgggc agctcccagg aatcgattgc aacacgagcg cagagggaga      780
gcatcaacta tatcaggtgt atgtgtgtgt tgataaatcc gatgcttcca ctgttattga      840
atgccccatt tatccacaca gcaattgccc atccatggtt gtgtttcctc cttttgggga      900
ggatcaggag gaccgagatg gttacacaga aggaatgtac gagctgtaga tctggacaaa      960
cagcatttct tctctccgca tttgattttt atcaatgaaa tttccgattc caacattttg     1020
taaaaaaaaa aaaaaaaa                                                   1038

<210> SEQ ID NO 47
<211> LENGTH: 91
<212> TYPE: DNA
<213> ORGANISM: Pinus radiata

<400> SEQUENCE: 47
aattttccat tcatgcctct gcccaactac aagaccggta aatggccaca gttctgtggt       60
tcctccgaag aattcgatat caagcttatc g                                      91

<210> SEQ ID NO 48
<211> LENGTH: 91
<212> TYPE: DNA
<213> ORGANISM: Pinus radiata

<400> SEQUENCE: 48
gcttttcatc cacactggtg cctcattcat tatataagat cagattcgtg tgatatacag       60
gcaaccatag aaacaaccgg caaagttact a                                      91

<210> SEQ ID NO 49
<211> LENGTH: 809
<212> TYPE: DNA
<213> ORGANISM: Pinus radiata

<400> SEQUENCE: 49
tgatatatat aacttctagc agaatgacac gcgacttgta tatcttttca ttttttaacc       60
catgaaaacc gattagggta ttgcaaatta gggcattgcc attcaaataa ttctcagatg      120
aaagattctc tctaacaatt acaaatgatt attttttcc atgagtgttg catgttcgaa       180
cggtctgccc agtctgtgag agagcataga gaaccctccc tgcccaattt gttagagcat      240
agagaaccct actgcatgag tagtaagaaa atattcggt ctcaattcgg caaagaccac       300
ctcgaatgga tgacttcaac gacaatctca tgatagtgtt ctgatcagca ccagttcacc      360
tatatatttt atctagggtt tagtttgcat gtatcaatcc tctggtgcac taggtaattc      420
tttcccagta tcatatatcc ttaatactgt tttgtctttt aatccatggc taccatcaga      480
acaagctcaa agcagaataa gggagcatca gccatcctct tgcttatcgc gattgcaggg      540
ttagtaaatg cgtgcaacgc tgtgggtatt gagccaatgt gcgacactgt ggtgtcgagt      600
```

```
cttctgaggc ttctgccatg caggacggct gttgatccct caattgccgc cattccactt      660
ccaagctgct gcaacgcggt tgagtcagct gggcttcaat gcctctgtct cgtcgttaac      720
ggccctcctt ttccaggggt cgaccgcggc ctcgcaatgc agctgcctgc caaatgccat      780
ctcacccttc ctccctgtaa cagttagtt                                        809

<210> SEQ ID NO 50
<211> LENGTH: 428
<212> TYPE: DNA
<213> ORGANISM: Eucalyptus grandis

<400> SEQUENCE: 50
tttcttgtga ctattcattt tcctcctgat tatccattca agcccccgaa ggttgcattt       60
aggactaaag ttttccaccc aaatataaat aacaatggaa gtatctgcct tgacatcttg      120
aaggaacagt ggagtcctgc tttgacaatc tccaaggttt gctctcaat ttgctctttg       180 ttgacggatc caaacccaga tgatcctctt gtaccagaga ttgctcatat gtacaagact      240 gatagggca aatatgagtc cactgcacgg agttggactc agaaatatgc aatgggttaa       300 cttttaaaaac tatatatcag tgatggaact ttatccctaa gttggaatct cttcgaatca      360
atgacttgtt tgcttgtaag aaatgttttcc ttaagataag tggctttcct caaaacttga     420
ttgaagtg                                                               428

<210> SEQ ID NO 51
<211> LENGTH: 525
<212> TYPE: DNA
<213> ORGANISM: Pinus radiata

<400> SEQUENCE: 51
cccttctttg ccttcaacta atcctgctca tcctctcctg cccccattcc caagatggc       60 tgcacccaga tcatccgcta aattgggtgc acttttggca atactgctca tagttgcggc      120
agcgcaggct caagattgct caaatgccat ggacaaattg gctccatgca cttcagcagt      180
gggactgtct agcaatggag tgaagccctc atctgagtgc tgtgatgccc tcaaaggaac      240
cagtactggc tgcgtctgca agtctgtgag agcagtgata tcacttcctg ctaagtgcaa      300
tctcccagcc ataacctgct ctggatctcg ctgaaggctc tctgttatgg cgattctcag      360
atcgtggatc tctttaagat tttcagcaag caagtgatag aataaattct cagattttga      420
gatatctata tagcgatttt cagtatcaga ttgtctatag tactcatata tttaagtgat      480
tgaatagcat tctccgattc cgagttggaa acacagacac aatga                      525

<210> SEQ ID NO 52
<211> LENGTH: 1126
<212> TYPE: DNA
<213> ORGANISM: Pinus radiata

<400> SEQUENCE: 52
actagtgatt actataggc acgcgtggtc gacggcccgg gctggtaaat acccaactta        60
atttaattgt tattgagcca gagagatgcg tagtcgctca tgtcacttgt gtttaccaaa      120
aagacataca taaacacctg cacctaaaag ttataatgat aacatgcata caaccctaca      180
acgtacgtag tcacatgcgg ctagaactta accctacc acaaacatag ccacctgcac         240
ccagaagtta taataataac atacatagaa cccttacaat aaaaaaagtt atctccaatg      300
attattaatc tactgcaggc cagccatact cagcttgaac gtgaaaattc gcattgtaag      360
catggcgcca cattaaaata acctcggcaa tattttcatg tccaagtggc cggccagcca      420
```

```
cgctcctcgc actctgagaa tactctattc atccacttgt ctctgccccg caactcatat      480
aaatgtggcc aacccaagca ccatatccat gttcattaat cccctctttg ccttcaacta      540
atcctgctca tccctcttg ccccaattcc caaagatggc tgcacccaga tcatccgcta       600
aatcggctgc acttttcgca atactgctca tagttgcggc agtacaggct gaagattgct      660
caaatgccat ggacaaattg ctccatgca cttcagcagt gggactgtct agcaatggag       720
tgaagccctc atctgagtgc tgtgatgccc tcaaaggaac cagtactggc tgcgtctgca      780
aatctgtgag agcagtgata tcacttcctg ctaagtgcaa tctcccagcc ttaacctgct      840
ctggatctcg ctgaaggctc tctgttatgg cgattctcag atcgtggatc tctttaagat      900
tttcaggaag caagtgatag aataaattct cagatgttga gatatctata tagcgatttt      960
cagtatcaga ttgtctacag taccaatata tttaagtgat tgaatggaat tctcggattc     1020
tgagatagaa atataggcac agaatgtggc cggaggaatg ttcgaattcg agaatgataa     1080
taaataataa atgattgatt tctctctgca aaaaaaaaa aaaaaa                     1126

<210> SEQ ID NO 53
<211> LENGTH: 454
<212> TYPE: DNA
<213> ORGANISM: Pinus radiata

<400> SEQUENCE: 53
atcctgctca tcctctcctg cccccattcc caaagatggc tgcacccaga tcatccgcta       60
aattgggtgc acttttggca atactgctca tagttgcggc agcgcaggct caagattgct      120
caaatgccat ggacaaattg ctccatgca cttcagcagt gggactgtct agcaatggag       180
tgaagccctc atctgagtgc tgtgatgccc tcaaaggaac cagtactggc tgcgtctgca      240
agtctgtgag agcagtgata tcacttcctg ctaagtgcaa tctcccagcc ataacctgct      300
ctggatctcg ctgaaggctc tctgttatgg cgattctcag atcgtggata tctttaagat      360
tttcagcaag tgatagaata aattctcaga ttttgagata tctatatagc gattttcagt      420
atcagattgt ctatagtact catatattta agtg                                  454

<210> SEQ ID NO 54
<211> LENGTH: 335
<212> TYPE: DNA
<213> ORGANISM: Pinus radiata

<400> SEQUENCE: 54
agaagcacct gttaaaaagg aggcctgctc tttgttcatg agcttataga taagccctag       60
tctgcaagga ttattgccct gtagttattt ggaagtagat cattttcaca ggcccagatg      120
cattatattc taatgcagtt gtttgttaat tgaagtgcaa atagttccaa aatgtttaca      180
tgaatcaata gtgaacaaat ccctctgttt tatatcatat tgatggatta ttcgattttt      240
tggtgacgtg gcgcgaaact gcttttcgaa ctcatggaaa tagtaattgt tataatccat      300
aggcatgaga ttcttgttaa tcgtgcacaa ggttt                                 335

<210> SEQ ID NO 55
<211> LENGTH: 336
<212> TYPE: DNA
<213> ORGANISM: Pinus radiata

<400> SEQUENCE: 55
aaaccttgtg cacgattaac aagaatctca tgcctatgga ttataacaat tactatttcc       60
atgagttcga aaagcagttt cgcgccacgt caccaaaaaa tcgaataatc catcaatatg      120
```

```
atataaaaca gagggatttg ttcactattg attcatgtaa acattttgga actatttgca      180
cttcaattaa caaacaactg cattagaata taatgcatct ggtgcctgtg aaaatgatct      240
acttccaaat aactacaggg caataatcct tgcagactag ggcttatcta taagctcatg      300
aacaaagagc aggcctcctt tttaacaggt gcttct                                336

<210> SEQ ID NO 56
<211> LENGTH: 532
<212> TYPE: DNA
<213> ORGANISM: Pinus radiata

<400> SEQUENCE: 56
cgttcgttcc cttcccttc cattgttgcg tttaagccct ccaattttct tttggcgtcc        60 cgttttggg gctcccttga agatctcctc ttcatttcgg gatttcctgc cttcgccgcg       120
ccatttgaag ttctttttct gagagaagaa tttagacatg gctgatcgca tgttgactcg       180
aagccacagc cttcgcgagc gtttggacga gaccctctct gctcaccgca acgatattgt       240
ggccttcctt tcaagggttg aagccaaggg caaaggcatc ttgcagcgcc accagatttt       300
tgctgagttt gaggccatct ctgaggagag cagagcaaag cttcttgatg ggccttttgg       360
tgaagtcctc aaatccactc aggaagcgat tgtgtcgcct ccatgggttg ctcttgctgt       420
tcgtccaagg ccgggcgtgt gggagcacat ccgtgtgaac gtccatgcgc ttgttcttga       480
gcaattggag gttgctgagt atctgcactt caaagaagag cttgctgatg ga              532

<210> SEQ ID NO 57
<211> LENGTH: 3103
<212> TYPE: DNA
<213> ORGANISM: Eucalyptus grandis

<400> SEQUENCE: 57
gggtgaaaac aattaatgag atcatttgaa ttaaggaaag tggaaaggcg gttttctgat        60
tggtacactg aaacaacagg aaggtggtgg aggccgcaat gatggaattt atccactta        120 atcattttat gaaatcgata cactaacctt tgtttctcct aaacccaaag cattaatcc        180 ctgtcctcct cactcgatct cgaaggccag aaggggagg ccgagcctct tgcttttttt        240
cgtgtataaa agggcctccc ccattcctca ttttttcacca tcctccgttc gttcgttccc       300 ttcccttcc attgttgcgt ttaagccctc caattttctt ttggcgtccc gttttggggg        360
ctcccttgaa gatctcctct tcatttcggg atttcctgcc ttcgccgcgc atttgaagt        420 tcttttttctg agagaagaat ttagacatgg ctgatcgcat gttgactcga agccacagcc       480
ttcgcgagcg tttggacgag accctctctg ctcaccgcaa cgatattgtg gccttccttt       540
caagggttga agccaagggc aaaggcatct tgcagcgcca ccagattttt gctgagtttg       600
aggccatctc tgaggagagc agagcaaagc ttcttgatgg ggcctttggt gaagtcctca       660
aatccactca ggaagcgatt gtgtcgcctc catgggttgc tcttgctgtt cgtccaaggc       720
cgggcgtgtg ggagcacatc cgtgtgaacg tccatgcgct tgttcttgag caattggagg       780
ttgctgagta tctgcacttc aaagaagagc ttgctgatga agcttgaat ggtaactttg        840 tgcttgagct tgactttgag ccattcactg cctctttttcc gcgcccgact ctttccaagt       900
ctattggcaa tggcgtcgag tttctcaatc gccatctctc cgctaagctc ttccatgaca       960
aggaaagctt gcaccctctg cttgaattcc tccaagtcca ctgctacaag gggaagaaca      1020
tgatggtgaa tgccagaatc cagaatgtgt tctccctcca acatgtcctg aggaaggcgg      1080
aggagtatct gacctcgctc aaacccgaga ccccgtactc ccagttcgag cacaagttcc      1140
```

```
aggagatcgg gctcgagcgg gggtggggtg acacggctga gcgcgtcctc gagatgatcc    1200
agctcctgtt ggatctcctt gaggctcccg acccgtgcac tctcgagaag ttcttggata    1260
gggttcccat ggtcttcaac gtcgtgatca tgtctcccca cggatacttt gctcaggacg    1320
acgtccttgg ttatccggat accggtggcc aggttgttta catcctggat caagttcgtg    1380
ccctagagga agaaatgctt caccgcatta agcaacaagg actggatatt actcctcgga    1440
ttctcattat cactcggctt cttccagacg cggttggaac cacctgtggc cagcgccttg    1500
agaaagtttt tgggaccgag tactcccaca ttcttcgcgt cccctcaga atgagaagg     1560 gagtcgtccg caagtggatt tcccggttcg aggtgtggcc ctatttggaa agatacactg    1620
aggatgtcgc gagcgaactt gctggagagt tgcagggcaa gcctgatctg atcatcggaa    1680
actacagtga tggaaacatt gttgcttcct tgttagcaca taaattaggt gttacacagt    1740
gtacaatagc ccatgcctc gagaagacga agtacccaga gtcagacata tactggaaga    1800
aatttgagga aaagtaccac ttctcttgcc agttcactgc tgatctcatc gccatgaacc    1860
acaccgactt cattatcacc agcaccttcc aagaaattgc tggaagcaag gatacagtgg    1920
ggcagtatga gagtcacatg aacttcactc ttcctggact ctaccgagtt gtccacggga    1980
tcgacgtctt cgacccgaag ttcaacattg tttcaccagg tgctgacatg agcatctact    2040
ttgcttacac cgaacaggag cggcggttga atccttcca ccctgagatc gaggaactcc     2100
tcttcagcga tgttgagaac aaggaacact tgtgtgtgtt gaaagataag aagaagccta    2160
ttattttcac catggcaagg ctggaccgtg tcaagaactt gacagggctt gttgagtggt    2220
atggcaagaa ctccaagttg agggaactcg ccaacttggt cgtggttgga ggtgacagga    2280
ggaaggattc gaaggacttg gaagagcagt ctgagatgaa gaaaatgtac gacctcatcg    2340
aaaagtacaa gctgaatggc cagttcaggt ggatttcctc ccagatgaac cgggtgagga    2400
atggagagct ctaccgctac atctgtgaca cgaagggagt cttcgttcaa ccggctatct    2460
atgaagcttt cgggttgacc gtggttgagg ccatgacttg tggattgcca accttttgcca   2520 cttgcaatgg tggaccagct gagatcattg tgcatggcaa atcgggctac acattgatc     2580 cttaccatgg tgaccaggcg gccgagcttc ttgtagactt cttcaacaag tgcaagattg    2640
accagtccca ctgggacgag atctcaaagg gtgccatgca gagaattgaa gagaagtata    2700
catggaaaat atattctgag aggctgttga acctgactgc cgtgtatggc ttctggaagc    2760
atgtgactaa ccttgatcgg cgcgagagtc gccggtacct tgaaatgttc tatgccctca    2820
agtatcgccc actggcacag tctgttcctc cggctgtcga gtaaacaaag agacagattg    2880
ttaccagaag acgaagcat tggacttttg aagttttcaa ggaataaaca ttggaaattg     2940
tttgaatttg ggattgccaa gagcgatctt tttcgtttcc tttttttggt ccttttctc    3000 ttctttgttt ccattccgcg aatgtttgca ttttggggtt tgtacccatc aattcagtaa    3060
atggttcatt ttcttttcaa aaaaaaaaaa aaaaaaaaa aaa                        3103
```

<210> SEQ ID NO 58
<211> LENGTH: 326
<212> TYPE: DNA
<213> ORGANISM: Eucalyptus grandis

<400> SEQUENCE: 58

```
ctcgaaaccg agacgctgac tgtgggttga gctctaacca atgggagtga tgtctctctt      60
acgtgcctgc cgtgggcccc agtgacgggc cccaaaagtg taaacgaagg aagctcccgg     120
ggatctgatt ggccgcgacg tccgcctctg acgtggcacc accgacgatt ttttttaat      180
```

```
atcttggtca agtcctaatt taactatggg gtccagatta gaagcttatc cactatggat        240
taaattaaat caaatgggaa ttaaattaaa ttaaaatcat cgtgcggagg tgcacgagat        300
gcacgagatc cgacggcgca gagcag                                             326

<210> SEQ ID NO 59
<211> LENGTH: 311
<212> TYPE: DNA
<213> ORGANISM: Eucalyptus grandis

<400> SEQUENCE: 59
attactatag ggcacgcgtg gtcgacggcc cgggctggta ctctcactaa ttctttagtt         60
ttccaattta gccccttctg taattgctca tcttctttac caaattctct aatttggccg        120
gcgaagggct gacaagggat tggtcatgtc accctcacca aaggttgccg aaggtccggt        180
gacctcagct gacggccacc tacaccaaat ctagctcact agcagcctaa gcccttcatc        240
aactctagtg aaaggttttg agtatttttt aataaaaaat atttaaaaaa tatatagcga        300
gagctcatta c                                                             311

<210> SEQ ID NO 60
<211> LENGTH: 2096
<212> TYPE: DNA
<213> ORGANISM: Eucalyptus grandis

<400> SEQUENCE: 60
gattactata gggcacgcgt ggtcgacggc ccgggctggt ctgagccatt taattcgaga         60
gcacatcgcc caaaattatt cttcttgctg ccataactgt cgaattttct cttttaggta        120
agtaaccaat gatgcatcat gttgacaaaa aggctgatta gtatgatctt ggagttgttg        180
gtgcaaattt gcaagctgac gatggcccct cagggaaatt aaggcgccaa cccagattgc        240
aaagagcaca aagagcacga tccaaccttt ccttaacaag atcatcacca gatcggccag        300
taagggtaat attaatttaa caaatagctc ttgtaccggg aactccgtat ttctctcact        360
tccataaacc cctgattaat ttggtgggaa agcgacagcc aacccacaaa aggtcagatg        420
tcatcccacg agagagagag agagagagag agagagagag agagttttct ctctatattc        480
tggttcaccg gttggagtca atggcatgcg tgacgaatgt acatattggt gtagggtcca        540
atattttgcg ggagggttgg tgaaccgcaa agttcctata tatcgaacct ccaccaccat        600
acctcacttc aatccccacc atttatccgt tttatttcct ctgcttttcct ttgctcgagt        660 ctcgcggaag agagagaaga gaggagagga gagaatgggt tcgaccggat ccagacccca        720
gatgaccccg acccaagtct cggacgagga ggcgaacctc ttcgccatgc agctggcgag        780
cgcctccgtg ctccccatgg tcctcaaggc cgccatcgag ctcgacctcc tcgagatcat        840
ggccaaggcc gggccgggcg cgttcctctc cccgggggaa gtcgcggccc agctcccgac        900
ccagaacccc gaggcacccg tcatgctcga ccggatcttc cggctgctgg ccagctactc        960
cgtgctcacg tgcaccctcc gcgacctccc cgatggcaag gtcgagcggc tctacggctt       1020
agcgccggtg tgcaagttct tggtcaagaa cgaggacggg gtctccatcg ccgcactcaa       1080
cttgatgaac caggacaaaa tcctcatgga aagctggtat tacctgaaag atgcggtcct       1140
tgaaggcgga atcccattca acaaggcgta cgggatgacc cgcttcgagt atcatggcac       1200
cgacccgcga ttcaacaaga tctttaaccg gggaatgtct gatcactcca ccattactat       1260
gaagaagata ctgaaaacat acaagggctt cgagggcctc gagaccgtgg tcgatgtcgg       1320
aggcggcact ggggccgtgc tcagcatgat cgttgccaaa taccccatca atgaaagggat       1380
```

```
caacttcgac cgccccaacg gattgaagac gccccacccc ttcctggtgt caagcacgtc    1440
ggaggcgaca tgttcgtcag cgttccaaag ggagatgcca ttttcatgaa gtggatatgc    1500
catgactgga gtgacgacca ttgcgcgaag ttcctcaaga actgctacga tgcgcttccc    1560
aacaatggaa aggtgatcgt tgcagagtgc gtactccctg tgtacccaga cacgagccta    1620
gcgaccaaga atgtgatcca catcgactgc atcatgttgg cccacaaccc aggcgggaaa    1680
gagaggacac agaaggagtt cgaggcattg gccaaggggg ccggatttca gggcttccaa    1740
gtcatgtgct gcgctttcgg cactcacgtc atggagttcc tgaagaccgc ttgatctgct    1800
cctctgtggt gatgttcatg gttcttggat ttgaaggtc gtgaaggagc ccttttctca    1860
cagttggctt cggcatacca agttcttctc ataaaaggaa acaataagaa gcgactgtat    1920 gatgcgcaa gtggaagtta caagatttgt tgttttatgt ctataaagtt ttgagtcttc     1980
tgcatactga tttcacagaa tgtgtaacga acggcgtat atggatgtgc ctgaatgatg     2040
gaaattgtga tattctgtct ctttttcag taaatcactt cgaacaaaaa aaaaaa        2096

<210> SEQ ID NO 61
<211> LENGTH: 522
<212> TYPE: DNA
<213> ORGANISM: Eucalyptus grandis

<400> SEQUENCE: 61
ctaaaacgct aatcctgccc tgcccttccc ttctgctgct gctgctcgtc acctctctct    60
ccctctcgcg gccagctgcg agatctgccg agtttaagcc tcgtacatca aaatgggtaa    120
ggagaagatt cacatcagca ttgtggtcat tggccatgtc gattctggga agtcaaccac    180
aactggccac ttgatataca agctcggagg aatcgacaag cgtgtgattg agagattcga    240
gaaggaagct gctgagatga acaagagatc gttcaagtat gcttgggtgc ttgacaagct    300
caaggccgag cgcgagcgcg gtattaccat tgatattgcc ttgtggaagt tcgagaccac    360
caagtactac tgcactgtca ttgatgctcc tggacatcgt gactttatta agaatatgat    420
tactggaacc tcccaggccg actgtgctgt ccttatcatt gattccacca ctggtggttt    480
cgaagctggt atttccaagg atggccagac ccgtgaacat gc                       522

<210> SEQ ID NO 62
<211> LENGTH: 420
<212> TYPE: DNA
<213> ORGANISM: Eucalyptus grandis

<400> SEQUENCE: 62
tttgatacgc taacaaacaa acatgtgaa aagcttaatt atggcaatta tcataaatag     60
aaaaaaatta gaaaaaaga gaggaaatgg gccattattt aaattgcaat cgaaagattg     120
agggcaattc tgtttctcta gtgtaaataa gggtgtattt aataattgag ggatggaaat    180
agcatggtca ctcggtaatt atcaaggaaa gcaagaataa aaatgaaaaa aaaaaaaaa    240 aaagcttgaa aggccaatg tcgaaattat gagcgcgaga tgaggacact cctgggaaac     300
gaaaaatggc attcgcgggg ggtgctatat aaagcctcgt gtaagggtgc gttcctcact    360 ctcaaacccct aatcctgccc ttcccttctg ctgctgctgc tcgtcacctc tctcctccct   420

<210> SEQ ID NO 63
<211> LENGTH: 65
<212> TYPE: PRT
<213> ORGANISM: Eucalyptus grandis

<400> SEQUENCE: 63
```

```
Met Asp Asn Ser Lys Met Gly Phe Asn Ala Gly Gln Ala Lys Gly Gln
1               5                   10                  15

Thr Gln Glu Lys Ser Asn Gln Met Met Asp Lys Ala Ser Asn Thr Ala
            20                  25                  30

Gln Ser Ala Arg Asp Ser Met Gln Glu Thr Gly Gln Gln Met Lys Ala
        35                  40                  45

Lys Ala Gln Gly Ala Ala Asp Ala Val Lys Asn Ala Thr Gly Met Asn
    50                  55                  60

Lys
65

<210> SEQ ID NO 64
<211> LENGTH: 152
<212> TYPE: PRT
<213> ORGANISM: Eucalyptus grandis

<400> SEQUENCE: 64

Met Gly Gly Pro Leu Thr Leu Asp Ala Glu Val Glu Val Lys Ser Pro
1               5                   10                  15

Ala Asp Lys Phe Trp Val Ser Val Arg Asp Ser Thr Lys Leu Phe Pro
            20                  25                  30

Lys Ile Phe Pro Asp Gln Tyr Lys Asn Ile Glu Val Leu Glu Gly Asp
        35                  40                  45

Gly Lys Ala Pro Gly Ser Val Arg Leu Phe Thr Tyr Gly Glu Gly Ser
    50                  55                  60

Pro Leu Val Lys Val Ser Lys Glu Lys Ile Asp Gly Val Asp Glu Ala
65                  70                  75                  80

Asp Lys Val Val Thr Tyr Ser Val Ile Asp Gly Asp Leu Leu Lys Tyr
                85                  90                  95

Tyr Lys Asn Phe Asn Gly Ser Ile Lys Val Ile Pro Lys Gly Asp Gly
            100                 105                 110

Ser Leu Val Lys Trp Ser Cys Gly Phe Glu Lys Ala Ser Asp Glu Ile
        115                 120                 125

Pro Asp Pro His Val Ile Lys Asp Phe Ala Ile Gln Asn Phe Lys Glu
    130                 135                 140

Leu Asp Glu Phe Ile Leu Lys Ala
145                 150

<210> SEQ ID NO 65
<211> LENGTH: 117
<212> TYPE: PRT
<213> ORGANISM: Eucalyptus grandis

<400> SEQUENCE: 65

Met Ala Ala Asn Phe Val Ile Pro Thr Lys Met Lys Ala Trp Val Tyr
1               5                   10                  15

Arg Glu His Gly Asn Val Ala Asp Val Leu Gly Leu Asp Pro Glu Leu
            20                  25                  30

Lys Val Pro Glu Leu Gln Glu Gly Gln Val Leu Val Lys Val Leu Ala
        35                  40                  45

Ala Leu Asn Pro Val Asp Ala Ala Arg Met Lys Gly Val Ile Lys
    50                  55                  60

Leu Pro Gly Phe Ser Leu Pro Ala Val Pro Gly Tyr Asp Leu Ala Gly
65                  70                  75                  80

Val Val Val Lys Val Gly Arg Glu Val Lys Glu Leu Lys Ile Gly Asp
                85                  90                  95
```

```
Glu Val Tyr Gly Phe Met Phe His Ala Lys Lys Asp Gly Thr Leu Ala
            100                 105                 110

Glu Tyr Ala Ala Val
        115
```

<210> SEQ ID NO 66
<211> LENGTH: 318
<212> TYPE: PRT
<213> ORGANISM: Eucalyptus grandis

<400> SEQUENCE: 66

```
Met Ala Ala Asn Phe Val Ile Pro Thr Lys Met Lys Ala Trp Val Tyr
  1               5                  10                  15

Arg Glu His Gly Asp Val Ala Asn Val Leu Gly Leu Asp Pro Glu Leu
             20                  25                  30

Lys Val Pro Glu Leu Gln Glu Gly Gln Val Leu Val Lys Val Leu Ala
         35                  40                  45

Ala Ala Leu Asn Pro Ile Asp Thr Ala Arg Val Lys Gly Val Ile Lys
     50                  55                  60

Leu Pro Gly Phe Ser Leu Pro Ala Val Pro Gly Tyr Asp Leu Ala Gly
 65                  70                  75                  80

Val Val Val Lys Val Gly Arg Glu Val Lys Glu Leu Lys Val Gly Asp
                 85                  90                  95

Glu Val Tyr Gly Phe Met Phe His Ala Lys Lys Asp Gly Thr Leu Ala
            100                 105                 110

Glu Tyr Ala Ala Val Glu Glu Ser Phe Leu Ala Leu Lys Pro Lys Lys
        115                 120                 125

Leu Arg Phe Gly Glu Ala Ala Ser Leu Pro Val Val Ile Gln Thr Ala
    130                 135                 140

Tyr Gly Gly Leu Glu Arg Ala Gly Leu Ser His Gly Lys Ser Leu Leu
145                 150                 155                 160

Val Leu Gly Gly Ala Gly Gly Val Gly Thr Leu Ile Ile Gln Leu Ala
                165                 170                 175

Lys Glu Val Phe Gly Ala Ser Arg Val Ala Ala Thr Ser Ser Thr Gly
            180                 185                 190

Lys Leu Glu Leu Leu Lys Ser Leu Gly Ala Asp Leu Ala Ile Asp Tyr
        195                 200                 205

Thr Lys Val Asn Phe Glu Asp Leu Pro Glu Lys Phe Asp Val Val Tyr
    210                 215                 220

Asp Thr Val Gly Glu Ile Glu Arg Ala Ala Lys Ala Val Lys Pro Gly
225                 230                 235                 240

Gly Ser Ile Val Thr Ile Val Lys Gln Asn Lys Thr Leu Pro Pro Pro
                245                 250                 255

Ala Phe Phe Phe Ala Val Thr Ser Asn Arg Ser Thr Leu Glu Lys Leu
            260                 265                 270

Lys Pro Leu Glu Ser Gly Lys Val Lys Pro Val Ile Asp Pro Lys
        275                 280                 285

Ser Pro Phe Pro Phe Ser Gln Ala Ile Glu Ala Phe Ser Tyr Leu Gln
    290                 295                 300

Thr Arg Arg Ala Thr Gly Lys Leu Val Ile His Pro Val Pro
305                 310                 315
```

<210> SEQ ID NO 67
<211> LENGTH: 156
<212> TYPE: PRT
<213> ORGANISM: Eucalyptus grandis -continued

<400> SEQUENCE: 67

Met Gln Ile Phe Val Lys Thr Leu Thr Gly Lys Thr Ile Thr Leu Glu
1               5                   10                  15

Val Glu Ser Ser Asp Thr Val Asp Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ala Asp Tyr Asn Ile Gln Lys Glu
    50                  55                  60

Ser Thr Leu His Leu Val Leu Arg Leu Arg Gly Gly Met Gln Ile Phe
65                  70                  75                  80

Val Lys Thr Leu Thr Gly Lys Thr Ile Thr Leu Glu Val Glu Ser Ser
                85                  90                  95

Asp Thr Val Asp Asn Val Lys Ala Lys Ile Gln Asp Lys Glu Gly Ile
            100                 105                 110

Pro Pro Asp Gln Gln Arg Leu Ile Phe Ala Gly Lys Gln Leu Glu Asp
        115                 120                 125

Gly Arg Thr Leu Ala Asp Tyr Asn Ile Gln Lys Glu Ser Thr Leu His
    130                 135                 140

Leu Val Leu Arg Leu Lys Gly Gly Met Gln Ile Phe
145                 150                 155

<210> SEQ ID NO 68
<211> LENGTH: 238
<212> TYPE: PRT
<213> ORGANISM: Eucalyptus grandis

<400> SEQUENCE: 68

Met Ala Thr His Ala Ala Leu Ala Pro Ser Thr Leu Pro Ala Asn Ala
1               5                   10                  15

Lys Phe Ser Ser Lys Ser Ser His Ser Phe Pro Thr Gln Cys Phe
            20                  25                  30

Ser Lys Arg Leu Glu Val Ala Glu Phe Ser Gly Leu Arg Ala Gly Ser
        35                  40                  45

Cys Val Thr Tyr Ala Lys Asn Ala Gly Glu Gly Ser Phe Phe Asp Ala
    50                  55                  60

Val Ala Ala Gln Leu Thr Pro Lys Thr Ser Ala Pro Ala Pro Ala Lys
65                  70                  75                  80

Gly Glu Thr Val Ala Lys Leu Lys Val Ala Ile Asn Gly Phe Gly Arg
                85                  90                  95

Ile Gly Arg Asn Phe Leu Arg Cys Trp His Gly Arg Lys Asn Ser Pro
            100                 105                 110

Leu Asp Val Ile Val Asn Asp Ser Gly Gly Val Lys Asn Ala Ser
        115                 120                 125

His Leu Leu Lys Tyr Asp Ser Met Leu Gly Thr Phe Lys Ala Asp Val
    130                 135                 140

Lys Ile Val Asp Asn Glu Thr Ile Ser Val Asp Gly Lys Pro Val Lys
145                 150                 155                 160

Val Val Ser Asn Arg Asp Pro Leu Lys Leu Pro Trp Ala Glu Leu Gly
                165                 170                 175

Ile Asp Ile Val Ile Glu Gly Thr Gly Val Phe Val Asp Gly Pro Gly
            180                 185                 190

Ala Gly Lys His Ile Gln Ala Gly Ala Lys Lys Val Ile Ile Thr Ala
        195                 200                 205

Pro Ala Lys Gly Ala Asp Ile Pro Thr Tyr Val Tyr Gly Val Asn Glu

```
              210                 215                 220
Thr Asp Tyr Ser His Glu Val Ala Asn Ile Ile Ser Asn Ala
225                 230                 235

<210> SEQ ID NO 69
<211> LENGTH: 168
<212> TYPE: PRT
<213> ORGANISM: Eucalyptus grandis

<400> SEQUENCE: 69

Met Ser Thr Ser Pro Val Ser Ser Trp Cys Ala Thr Ser Phe Ser Pro
1               5                   10                  15

Ala His Ser Ser Leu Lys Arg Ala Ala Gly Leu Arg Pro Ser Leu Ser
                20                  25                  30

Ala Arg Leu Gly Pro Ser Ser Ser Ser Val Ser Pro Thr
            35                  40                  45

Leu Ile Arg Asn Glu Pro Val Phe Ala Ala Pro Ala Pro Val Ile Asn
50                  55                  60

Pro Thr Trp Thr Glu Glu Met Gly Lys Asp Tyr Asp Glu Ala Ile Glu
65                  70                  75                  80

Ala Leu Lys Lys Leu Leu Ser Glu Lys Gly Asp Leu Lys Ala Thr Ala
                85                  90                  95

Ala Ala Lys Val Glu Gln Ile Thr Ala Glu Leu Gln Thr Ala Ser Pro
            100                 105                 110

Asp Ile Lys Pro Ser Ser Ser Val Asp Arg Ile Lys Thr Gly Phe Thr
        115                 120                 125

Phe Phe Lys Lys Glu Lys Tyr Asp Lys Asn Pro Ala Leu Tyr Gly Glu
130                 135                 140

Leu Ala Lys Gln Ser Pro Lys Phe Met Val Phe Ala Cys Ser Asp Ser
145                 150                 155                 160

Arg Val Cys Pro Ser His Val Leu
                165

<210> SEQ ID NO 70
<211> LENGTH: 214
<212> TYPE: PRT
<213> ORGANISM: Eucalyptus grandis

<400> SEQUENCE: 70

Met Pro Cys Pro Arg Ala Pro Pro Met Met Glu Arg Arg Ile Lys Pro
1               5                   10                  15

Gln Thr Glu Gln Ala Leu Lys Cys Pro Arg Cys Asp Ser Thr Asn Thr
                20                  25                  30

Lys Phe Cys Tyr Tyr Asn Asn Tyr Asn Leu Ser Gln Pro Arg His Phe
            35                  40                  45

Cys Lys Thr Cys Arg Arg Tyr Trp Thr Lys Gly Gly Ala Leu Arg Asn
50                  55                  60

Val Pro Val Gly Gly Gly Cys Arg Lys Asn Lys Arg Ala Lys Arg Ala
65                  70                  75                  80

Val Asp His Pro Val Ser Ala Gln Asn Glu Ala Ser Thr Ser Ala Ala
                85                  90                  95

Pro Gly Asn Glu Val Pro Asp Arg Ser Pro Phe Glu Pro Ser Ser
            100                 105                 110

Lys Ser Ile Tyr Tyr Gly Gly Glu Asn Met Asn Leu Thr Gly Leu Pro
        115                 120                 125

Phe Ser Arg Ile Gln Gln Asp Arg Ala Ala Leu Ala His Cys Asn Ser
130                 135                 140
```

```
Ser Ser Phe Leu Gly Met Ser Cys Gly Thr Gln Ser Ala Ser Leu Glu
145                 150                 155                 160

Pro His Leu Ser Ala Leu Asn Thr Phe Asn Ser Phe Lys Ser Asn Asn
            165                 170                 175

Pro Gly Leu Asp Phe Pro Ser Leu Ser Thr Asp Gln Asn Ser Leu Phe
            180                 185                 190

Glu Thr Ser Gln Pro Gln Leu Ser Arg Ala Met Ala Ser Ala Leu Phe
        195                 200                 205

Ser Met Pro Met Ala Pro
        210

<210> SEQ ID NO 71
<211> LENGTH: 166
<212> TYPE: PRT
<213> ORGANISM: Pinus radiata

<400> SEQUENCE: 71

Met Ala Ala Leu Ala Thr Thr Glu Val Cys Asp Thr Tyr Pro Arg Leu
1               5                   10                  15

Val Glu Asn Gly Glu Leu Arg Val Leu Gln Pro Ile Phe Gln Ile Tyr
            20                  25                  30

Gly Arg Arg Arg Ala Phe Ser Gly Pro Ile Val Thr Leu Lys Val Phe
        35                  40                  45

Glu Asp Asn Val Leu Leu Arg Glu Phe Leu Glu Glu Arg Gly Asn Gly
    50                  55                  60

Arg Val Leu Val Val Asp Gly Gly Ser Leu Arg Cys Ala Ile Leu
65                  70                  75                  80

Gly Gly Asn Val Val Val Ser Ala Gln Asn Asn Gly Trp Ser Gly Ile
                85                  90                  95

Ile Val Thr Gly Cys Ile Arg Asp Val Asp Glu Ile Asn Arg Cys Asp
            100                 105                 110

Ile Gly Ile Arg Ala Leu Thr Ser Asn Pro Leu Lys Ala Asn Lys Lys
        115                 120                 125

Gly Val Gly Glu Lys His Ala Pro Ile Tyr Ile Ala Gly Thr Arg Ile
    130                 135                 140

Leu Pro Gly Glu Trp Cys Tyr Ala Asp Ser Asp Gly Ile Leu Val Ser
145                 150                 155                 160

Gln Gln Glu Leu Ser Leu
                165

<210> SEQ ID NO 72
<211> LENGTH: 236
<212> TYPE: PRT
<213> ORGANISM: Pinus radiata

<400> SEQUENCE: 72

Met Leu Val Leu Ile Ile Phe Gly Cys Cys Phe Ile Gly Val Ile Ala
1               5                   10                  15

Thr Ser Phe Asp Phe Tyr Tyr Phe Val Gln Gln Trp Pro Gly Ser Tyr
            20                  25                  30

Cys Asp Thr Arg Arg Gly Cys Cys Tyr Pro Arg Thr Gly Arg Pro Ala
        35                  40                  45

Ser Glu Phe Ser Ile His Gly Leu Trp Pro Asn Tyr Lys Thr Gly Lys
    50                  55                  60

Trp Pro Gln Phe Cys Gly Ser Ser Glu Glu Phe Asp Tyr Ser Lys Ile
65                  70                  75                  80
```

```
Ser Asp Leu Glu Glu Leu Asn Arg Tyr Trp Gly Ser Leu Ser Cys
            85                  90                  95

Pro Ser Ser Asp Gly Gln Glu Phe Trp Gly His Glu Trp Lys His
            100                 105                 110

Gly Thr Cys Ser Leu Asn Leu Asp Glu His Ser Tyr Phe Glu Lys Ala
            115                 120                 125

Leu Ser Leu Arg Gln Asn Ile Asp Ile Leu Gly Ala Leu Lys Thr Ala
            130                 135                 140

Gly Ile Lys Pro Asp Gly Ser Gln Tyr Ser Leu Ser Asp Ile Lys Glu
145                 150                 155                 160

Ala Ile Lys Gln Asn Thr Gly Gln Leu Pro Gly Ile Asp Cys Asn Thr
                165                 170                 175

Ser Ala Glu Gly Glu His Gln Leu Tyr Gln Val Tyr Val Cys Val Asp
                180                 185                 190

Lys Ser Asp Ala Ser Thr Val Ile Glu Cys Pro Ile Tyr Pro His Ser
                195                 200                 205

Asn Cys Pro Ser Met Val Val Phe Pro Pro Phe Gly Glu Asp Gln Glu
            210                 215                 220

Asp Arg Asp Gly Tyr Thr Glu Gly Met Tyr Glu Leu
225                 230                 235

<210> SEQ ID NO 73
<211> LENGTH: 92
<212> TYPE: PRT
<213> ORGANISM: Pinus radiata

<400> SEQUENCE: 73

Met Ala Ala Pro Arg Ser Ser Ala Lys Leu Gly Ala Leu Leu Ala Ile
1               5                   10                  15

Leu Leu Ile Val Ala Ala Ala Gln Ala Gln Asp Cys Ser Asn Ala Met
            20                  25                  30

Asp Lys Leu Ala Pro Cys Thr Ser Ala Val Gly Leu Ser Ser Asn Gly
            35                  40                  45

Val Lys Pro Ser Ser Glu Cys Cys Asp Ala Leu Lys Gly Thr Ser Thr
        50                  55                  60

Gly Cys Val Cys Lys Ser Val Arg Ala Val Ile Ser Leu Pro Ala Lys
65                  70                  75                  80

Cys Asn Leu Pro Ala Ile Thr Cys Ser Gly Ser Arg
                85                  90

<210> SEQ ID NO 74
<211> LENGTH: 92
<212> TYPE: PRT
<213> ORGANISM: Pinus radiata

<400> SEQUENCE: 74

Met Ala Ala Pro Arg Ser Ser Ala Lys Ser Ala Ala Leu Phe Ala Ile
1               5                   10                  15

Leu Leu Ile Val Ala Ala Val Gln Ala Glu Asp Cys Ser Asn Ala Met
            20                  25                  30

Asp Lys Leu Ala Pro Cys Thr Ser Ala Val Gly Leu Ser Ser Asn Gly
            35                  40                  45

Val Lys Pro Ser Ser Glu Cys Cys Asp Ala Leu Lys Gly Thr Ser Thr
        50                  55                  60

Gly Cys Val Cys Lys Ser Val Arg Ala Val Ile Ser Leu Pro Ala Lys
65                  70                  75                  80

Cys Asn Leu Pro Ala Leu Thr Cys Ser Gly Ser Arg
```

<210> SEQ ID NO 75
<211> LENGTH: 92
<212> TYPE: PRT
<213> ORGANISM: Pinus radiata

<400> SEQUENCE: 75

Met Ala Ala Pro Arg Ser Ser Ala Lys Leu Gly Ala Leu Leu Ala Ile
1               5                   10                  15

Leu Leu Ile Val Ala Ala Gln Ala Gln Asp Cys Ser Asn Ala Met
            20                  25                  30

Asp Lys Leu Ala Pro Cys Thr Ser Ala Val Gly Leu Ser Ser Asn Gly
        35                  40                  45

Val Lys Pro Ser Ser Glu Cys Cys Asp Ala Leu Lys Gly Thr Ser Thr
    50                  55                  60

Gly Cys Val Cys Lys Ser Val Arg Ala Val Ile Ser Leu Pro Ala Lys
65                  70                  75                  80

Cys Asn Leu Pro Ala Ile Thr Cys Ser Gly Ser Arg
                85                  90

<210> SEQ ID NO 76
<211> LENGTH: 125
<212> TYPE: PRT
<213> ORGANISM: Eucalyptus grandis

<400> SEQUENCE: 76

Met Ala Asp Arg Met Leu Thr Arg Ser His Ser Leu Arg Glu Arg Leu
1               5                   10                  15

Asp Glu Thr Leu Ser Ala His Arg Asn Asp Ile Val Ala Phe Leu Ser
            20                  25                  30

Arg Val Glu Ala Lys Gly Lys Gly Ile Leu Gln Arg His Gln Ile Phe
        35                  40                  45

Ala Glu Phe Glu Ala Ile Ser Glu Glu Ser Arg Ala Lys Leu Leu Asp
    50                  55                  60

Gly Ala Phe Gly Glu Val Leu Lys Ser Thr Gln Glu Ala Ile Val Ser
65                  70                  75                  80

Pro Pro Trp Val Ala Leu Ala Val Arg Pro Arg Pro Gly Val Trp Glu
                85                  90                  95

His Ile Arg Val Asn Val His Ala Leu Val Leu Glu Gln Leu Glu Val
            100                 105                 110

Ala Glu Tyr Leu His Phe Lys Glu Glu Leu Ala Asp Gly
        115                 120                 125

<210> SEQ ID NO 77
<211> LENGTH: 805
<212> TYPE: PRT
<213> ORGANISM: Eucalyptus grandis

<400> SEQUENCE: 77

Met Ala Asp Arg Met Leu Thr Arg Ser His Ser Leu Arg Glu Arg Leu
1               5                   10                  15

Asp Glu Thr Leu Ser Ala His Arg Asn Asp Ile Val Ala Phe Leu Ser
            20                  25                  30

Arg Val Glu Ala Lys Gly Lys Gly Ile Leu Gln Arg His Gln Ile Phe
        35                  40                  45

Ala Glu Phe Glu Ala Ile Ser Glu Glu Ser Arg Ala Lys Leu Leu Asp
    50                  55                  60

-continued

Gly Ala Phe Gly Glu Val Leu Lys Ser Thr Gln Ala Ile Val Ser
65                  70                  75                  80

Pro Pro Trp Val Ala Leu Ala Val Arg Pro Arg Pro Gly Val Trp Glu
                85                  90                  95

His Ile Arg Val Asn Val His Ala Leu Val Leu Glu Gln Leu Glu Val
            100                 105                 110

Ala Glu Tyr Leu His Phe Lys Glu Glu Leu Ala Asp Gly Ser Leu Asn
        115                 120                 125

Gly Asn Phe Val Leu Glu Leu Asp Phe Glu Pro Phe Thr Ala Ser Phe
    130                 135                 140

Pro Arg Pro Thr Leu Ser Lys Ser Ile Gly Asn Gly Val Glu Phe Leu
145                 150                 155                 160

Asn Arg His Leu Ser Ala Lys Leu Phe His Asp Lys Glu Ser Leu His
                165                 170                 175

Pro Leu Leu Glu Phe Leu Gln Val His Cys Tyr Lys Gly Lys Asn Met
            180                 185                 190

Met Val Asn Ala Arg Ile Gln Asn Val Phe Ser Leu Gln His Val Leu
        195                 200                 205

Arg Lys Ala Glu Glu Tyr Leu Thr Ser Leu Lys Pro Glu Thr Pro Tyr
    210                 215                 220

Ser Gln Phe Glu His Lys Phe Gln Glu Ile Gly Leu Glu Arg Gly Trp
225                 230                 235                 240

Gly Asp Thr Ala Glu Arg Val Leu Glu Met Ile Gln Leu Leu Leu Asp
                245                 250                 255

Leu Leu Glu Ala Pro Asp Pro Cys Thr Leu Glu Lys Phe Leu Asp Arg
            260                 265                 270

Val Pro Met Val Phe Asn Val Val Ile Met Ser Pro His Gly Tyr Phe
        275                 280                 285

Ala Gln Asp Asp Val Leu Gly Tyr Pro Asp Thr Gly Gly Gln Val Val
    290                 295                 300

Tyr Ile Leu Asp Gln Val Arg Ala Leu Glu Glu Met Leu His Arg
305                 310                 315                 320

Ile Lys Gln Gln Gly Leu Asp Ile Thr Pro Arg Ile Leu Ile Ile Thr
                325                 330                 335

Arg Leu Leu Pro Asp Ala Val Gly Thr Thr Cys Gly Gln Arg Leu Glu
            340                 345                 350

Lys Val Phe Gly Thr Glu Tyr Ser His Ile Leu Arg Val Pro Phe Arg
        355                 360                 365

Asn Glu Lys Gly Val Val Arg Lys Trp Ile Ser Arg Phe Glu Val Trp
    370                 375                 380

Pro Tyr Leu Glu Arg Tyr Thr Glu Asp Val Ala Ser Glu Leu Ala Gly
385                 390                 395                 400

Glu Leu Gln Gly Lys Pro Asp Leu Ile Ile Gly Asn Tyr Ser Asp Gly
                405                 410                 415

Asn Ile Val Ala Ser Leu Leu Ala His Lys Leu Gly Val Thr Gln Cys
            420                 425                 430

Thr Ile Ala His Ala Leu Glu Lys Thr Lys Tyr Pro Glu Ser Asp Ile
        435                 440                 445

Tyr Trp Lys Lys Phe Glu Glu Lys Tyr His Phe Ser Cys Gln Phe Thr
    450                 455                 460

Ala Asp Leu Ile Ala Met Asn His Thr Asp Phe Ile Ile Thr Ser Thr
465                 470                 475                 480

Phe Gln Glu Ile Ala Gly Ser Lys Asp Thr Val Gly Gln Tyr Glu Ser
                485                 490                 495

His Met Asn Phe Thr Leu Pro Gly Leu Tyr Arg Val Val His Gly Ile
                500                 505                 510

Asp Val Phe Asp Pro Lys Phe Asn Ile Val Ser Pro Gly Ala Asp Met
            515                 520                 525

Ser Ile Tyr Phe Ala Tyr Thr Glu Gln Glu Arg Leu Lys Ser Phe
        530                 535                 540

His Pro Glu Ile Glu Glu Leu Leu Phe Ser Asp Val Glu Asn Lys Glu
545                 550                 555                 560

His Leu Cys Val Leu Lys Asp Lys Lys Pro Ile Ile Phe Thr Met
                565                 570                 575

Ala Arg Leu Asp Arg Val Lys Asn Leu Thr Gly Leu Val Glu Trp Tyr
                580                 585                 590

Gly Lys Asn Ser Lys Leu Arg Glu Leu Ala Asn Leu Val Val Gly
        595                 600                 605

Gly Asp Arg Arg Lys Asp Ser Lys Asp Leu Glu Glu Gln Ser Glu Met
        610                 615                 620

Lys Lys Met Tyr Asp Leu Ile Glu Lys Tyr Lys Leu Asn Gly Gln Phe
625                 630                 635                 640

Arg Trp Ile Ser Ser Gln Met Asn Arg Val Arg Asn Gly Glu Leu Tyr
                645                 650                 655

Arg Tyr Ile Cys Asp Thr Lys Gly Val Phe Val Gln Pro Ala Ile Tyr
                660                 665                 670

Glu Ala Phe Gly Leu Thr Val Val Glu Ala Met Thr Cys Gly Leu Pro
                675                 680                 685

Thr Phe Ala Thr Cys Asn Gly Gly Pro Ala Glu Ile Ile Val His Gly
                690                 695                 700

Lys Ser Gly Tyr His Ile Asp Pro Tyr His Gly Asp Gln Ala Ala Glu
705                 710                 715                 720

Leu Leu Val Asp Phe Phe Asn Lys Cys Lys Ile Asp Gln Ser His Trp
                725                 730                 735

Asp Glu Ile Ser Lys Gly Ala Met Gln Arg Ile Glu Glu Lys Tyr Thr
                740                 745                 750

Trp Lys Ile Tyr Ser Glu Arg Leu Leu Asn Leu Thr Ala Val Tyr Gly
                755                 760                 765

Phe Trp Lys His Val Thr Asn Leu Asp Arg Arg Glu Ser Arg Tyr
        770                 775                 780

Leu Glu Met Phe Tyr Ala Leu Lys Tyr Arg Pro Leu Ala Gln Ser Val
785                 790                 795                 800

Pro Pro Ala Val Glu
                805

<210> SEQ ID NO 78
<211> LENGTH: 264
<212> TYPE: PRT
<213> ORGANISM: Eucalyptus grandis

<400> SEQUENCE: 78

Met Gly Ser Thr Gly Ser Glu Thr Gln Met Thr Pro Thr Gln Val Ser
  1               5                  10                  15

Asp Glu Glu Ala Asn Leu Phe Ala Met Gln Leu Ala Ser Ala Ser Val
            20                  25                  30

Leu Pro Met Val Leu Lys Ala Ala Ile Glu Leu Asp Leu Leu Glu Ile
        35                  40                  45

Met Ala Lys Ala Gly Pro Gly Ala Phe Leu Ser Pro Gly Glu Val Ala
    50                  55                  60

```
Ala Gln Leu Pro Thr Gln Asn Pro Glu Ala Pro Val Met Leu Asp Arg
 65                  70                  75                  80

Ile Phe Arg Leu Leu Ala Ser Tyr Ser Val Leu Thr Cys Thr Leu Arg
                 85                  90                  95

Asp Leu Pro Asp Gly Lys Val Glu Arg Leu Tyr Gly Leu Ala Pro Val
            100                 105                 110

Cys Lys Phe Leu Val Lys Asn Glu Asp Gly Val Ser Ile Ala Ala Leu
        115                 120                 125

Asn Leu Met Asn Gln Asp Lys Ile Leu Met Glu Ser Trp Tyr Tyr Leu
    130                 135                 140

Lys Asp Ala Val Leu Glu Gly Gly Ile Pro Phe Asn Lys Ala Tyr Gly
145                 150                 155                 160

Met Thr Ala Phe Glu Tyr His Gly Thr Asp Pro Arg Phe Asn Lys Ile
                165                 170                 175

Phe Asn Arg Gly Met Ser Asp His Ser Thr Ile Thr Met Lys Lys Ile
            180                 185                 190

Leu Glu Thr Tyr Lys Gly Phe Glu Gly Leu Glu Thr Val Val Asp Val
        195                 200                 205

Gly Gly Gly Thr Gly Ala Val Leu Ser Met Ile Val Ala Lys Tyr Pro
    210                 215                 220

Ser Met Lys Gly Ile Asn Phe Asp Arg Pro Asn Gly Leu Lys Thr Pro
225                 230                 235                 240

His Pro Phe Leu Val Ser Ser Thr Ser Glu Ala Thr Cys Ser Ser Ala
                245                 250                 255

Phe Gln Arg Glu Met Pro Phe Ser
            260

<210> SEQ ID NO 79
<211> LENGTH: 136
<212> TYPE: PRT
<213> ORGANISM: Eucalyptus grandis

<400> SEQUENCE: 79

Met Gly Lys Glu Lys Ile His Ile Ser Ile Val Val Ile Gly His Val
 1               5                  10                  15

Asp Ser Gly Lys Ser Thr Thr Thr Gly His Leu Ile Tyr Lys Leu Gly
            20                  25                  30

Gly Ile Asp Lys Arg Val Ile Glu Arg Phe Glu Lys Glu Ala Ala Glu
        35                  40                  45

Met Asn Lys Arg Ser Phe Lys Tyr Ala Trp Val Leu Asp Lys Leu Lys
    50                  55                  60

Ala Glu Arg Glu Arg Gly Ile Thr Ile Asp Ile Ala Leu Trp Lys Phe
 65                  70                  75                  80

Glu Thr Thr Lys Tyr Tyr Cys Thr Val Ile Asp Ala Pro Gly His Arg
                 85                  90                  95

Asp Phe Ile Lys Asn Met Ile Thr Gly Thr Ser Gln Ala Asp Cys Ala
            100                 105                 110

Val Leu Ile Ile Asp Ser Thr Thr Gly Gly Phe Glu Ala Gly Ile Ser
        115                 120                 125

Lys Asp Gly Gln Thr Arg Glu His
    130                 135

<210> SEQ ID NO 80
<211> LENGTH: 229
<212> TYPE: PRT
<213> ORGANISM: Eucalyptus grandis
```

<400> SEQUENCE: 80

```
Met Gln Ile Phe Val Lys Thr Leu Thr Gly Lys Thr Ile Thr Leu Glu
1               5                   10                  15
Val Glu Ser Ser Asp Thr Ile Asp Asn Val Lys Ala Lys Ile Gln Asp
            20                  25                  30
Lys Glu Gly Ile Pro Pro Asp Gln Gln Arg Leu Ile Phe Ala Gly Lys
        35                  40                  45
Gln Leu Glu Asp Gly Arg Thr Leu Ala Asp Tyr Asn Ile Gln Lys Glu
    50                  55                  60
Ser Thr Leu His Leu Val Leu Arg Leu Arg Gly Gly Met Gln Ile Phe
65                  70                  75                  80
Val Lys Thr Leu Thr Gly Lys Thr Ile Thr Leu Glu Val Glu Ser Ser
                85                  90                  95
Asp Thr Ile Asp Asn Val Lys Ala Lys Ile Gln Asp Lys Glu Gly Ile
            100                 105                 110
Pro Pro Asp Gln Gln Arg Leu Ile Phe Ala Gly Lys Gln Leu Glu Asp
        115                 120                 125
Gly Arg Thr Leu Ala Asp Tyr Asn Ile Gln Lys Glu Ser Thr Leu His
    130                 135                 140
Leu Val Leu Arg Leu Arg Gly Gly Met Gln Ile Phe Val Lys Thr Leu
145                 150                 155                 160
Thr Gly Lys Thr Ile Thr Leu Glu Val Glu Ser Ser Asp Thr Ile Asp
                165                 170                 175
Asn Val Lys Ala Lys Ile Gln Asp Lys Glu Gly Ile Pro Pro Asp Gln
            180                 185                 190
Gln Arg Leu Ile Phe Ala Gly Lys Gln Leu Glu Asp Gly Arg Thr Leu
        195                 200                 205
Ala Asp Tyr Asn Ile Gln Lys Glu Ser Thr Leu His Leu Val Leu Arg
    210                 215                 220
Leu Arg Gly Gly Phe
225
```

<210> SEQ ID NO 81
<211> LENGTH: 345
<212> TYPE: DNA
<213> ORGANISM: Eucalyptus grandis

<400> SEQUENCE: 81

```
taataaatga tgaatttatt ataaacgtat ccgtttgaga ttttttgtggg tcataggtgt      60
atcaatttga aatctttgat agtaacaaaa ataatttttag gtagtttatg ttttttcatga   120
tataaaccctt gaaagttaat gctactaaat tgttatatat atattaggca aattacaacc    180
ttaatgcaac agttaatgac gtgatactgt tcagattata gatacaatgg ttatccttga    240
atgaataaga agaagtccta agggcaagtg ctatgagctt gcacgactgc ttttgcgcca    300
ttttttgttta ccagcccggg ccgtcgacca cgcgtgccct atagt                   345
```

<210> SEQ ID NO 82
<211> LENGTH: 72
<212> TYPE: DNA
<213> ORGANISM: Eucalyptus grandis

<400> SEQUENCE: 82

```
cagtagggga cttgttcccc caagggcacg tgtcgttggt gaagctctgg cggtggatga     60
accgcgtggg cc                                                         72
```

<210> SEQ ID NO 83
<211> LENGTH: 544
<212> TYPE: DNA
<213> ORGANISM: Eucalyptus grandis

<400> SEQUENCE: 83

| | | | | | |
|---|---|---|---|---|---|
| actagtgatt | tcgtcgtctt | cgtcttcttc | gtcttctgga | acttcgttgc | tccgagcttt | 60 |
| atcagaaccg | gcgatggaaa | tgaaaccctc | gttctctctc | cctcgctcct | ctctttcttc | 120 |
| tatccaggag | cgtttgtaca | ctgggagtac | agagcttctt | gcgataccga | aactacccct | 180 |
| ggacgactgg | ccttttttgcc | tcgcgccccc | tctctgagcc | ggggcgcaat | ttgtcccttt | 240 |
| cccagagcga | agtgtcgatt | ttgtccttcc | acgaggcttt | acctactccc | atcgcccgag | 300 |
| ccccaagccc | aggcccaaat | gcctgttcct | tgtggccctg | ccaacattcc | ctttgaaatt | 360 |
| aaaaaattaa | aaaaaaactc | tctgccaggc | aaaagtaaag | attaacacca | ccaaaattta | 420 |
| taacaaattt | atcattcatt | aattttcgtt | aaattttatt | ttcaaattac | tgagtcgaat | 480 |
| tacatgtata | aattcacgga | tgtatcggtt | cgagattttta | tcctctaatt | atcattagtg | 540 |
| tatg | | | | | | 544 |

<210> SEQ ID NO 84
<211> LENGTH: 515
<212> TYPE: DNA
<213> ORGANISM: Eucalyptus grandis

<400> SEQUENCE: 84

| | | | | | |
|---|---|---|---|---|---|
| gattactata | gggcacgcgt | ggtcgacggc | ccgggctggt | ctgccttcct | ttaactcccc | 60 |
| ttttttgtaa | cttttttaaaa | tgtagtttta | aatttaattt | aattactttt | tatattaatt | 120 |
| atttaccaca | tcagagacaa | acaatgtctt | ttttttgtatt | ttctagtcac | gtcaacatgc | 180 |
| aaaacaacgc | cattttgcac | tcaccttgcc | ggaaaattgc | cacgtcaaca | atttggctag | 240 |
| agtggcgctt | aagtgatcta | ttttgctcca | attttggcac | ttaagtgtca | ttttcctaaa | 300 |
| ttttagcact | taaagtattc | ctctatgtca | agttttgaca | cttggggtgt | actttgtcca | 360 |
| atcataaacc | gtataagttc | actttaaaca | aaaatggcgc | aaaagcagtc | gtgcaagctc | 420 |
| atagcacttg | cccttaggac | ttcttcttat | tcattcaagg | ataaccattg | tatctataat | 480 |
| ctgaacagta | tcacgtcatt | aactgttgca | ttaag | | | 515 |

<210> SEQ ID NO 85
<211> LENGTH: 515
<212> TYPE: DNA
<213> ORGANISM: Eucalyptus grandis

<400> SEQUENCE: 85

| | | | | | |
|---|---|---|---|---|---|
| actagtgatt | tcgtcgtctt | cgtcttcttc | gtcttctgga | acttcgttgc | tccgagcttt | 60 |
| atcagaaccg | gcgatggaaa | tgaaaccctc | gttctctctc | cctcgctcct | ctctttcttc | 120 |
| tatccaggag | cgtttgtaca | ctgggagtac | agagcttctt | gcgataccga | aactacccct | 180 |
| ggacgactgg | ccttttttgcc | tcgtgccccc | tctctgagcc | ggggcgcaat | ttgtcccttt | 240 |
| cccagagcga | agtgtcgatt | ttgtccttcc | acgaggcttt | acctactccc | atcgcccgag | 300 |
| ccccaagccc | aggcccaaat | gcctgttcct | tgtggccctg | ccaacattcc | ctttgaaatt | 360 |
| aaaaaattaa | aaaaaaactc | tctgccaggc | aaaagtaaag | attaacacca | ccaaaattta | 420 |
| taacaaattt | atcattcatt | aattttcgtt | aaattttatt | ttcaaattac | tgagtcgaat | 480 |
| tacatgtata | aattcacgga | tgtatcggtt | cgaga | | | 515 |

<210> SEQ ID NO 86
<211> LENGTH: 782
<212> TYPE: DNA
<213> ORGANISM: Eucalyptus grandis

<400> SEQUENCE: 86

```
gagggtttca tttccatcgc cggttctgat aaagctcgga gcaacgaagt tccagaagac      60
gaagaagacg aagacgacga cggcgacatg ccttgcttga acatctccac caacgtcagc     120
ctcgacggcc tcgacacctc cgccattctc tccgagacca cctccggcgt cgccaagctc     180
atcggcaagc ccgaggccta tgtgatgatt gtgttgaagg ggtcagtccc catggctttt     240
ggtgggactg agcaacctgc tgcctatggc gagttggtgt caatcggcgg tttgaacccc     300
gatgtgaaca agaagctgag tgctgcaatt gcttcaatcc tcgaaaccaa gctgtccatc     360
cccaagtcgc ggttcttcct gaaattttat gataccaagg gttccttctt tggatggaat     420
ggatccacct tctgagctgt tggtcgcatt ctcctcagtg tttaccatgt atttcggccc     480
taaactctac ttctaggcct gttaaaagtg tcttttttaa ggtaattctg ctattacccc     540
tcttaagtgc atcttatcag taaacatgga atatcctgaa ctttgattat atgccggctc     600
gtggctgtgg aagcacttct ttatgttacc accagcttct caggtgaata taagctttgc     660
ccagtctgtt ctctggggga tttgcttggt gggtagtggc aatcagatgg ttttgtcact     720
tttgtgcata tttaagtagt aaatgtccac gacagcccaa agagtagcaa tccgggtgca     780
ct                                                                    782
```

<210> SEQ ID NO 87
<211> LENGTH: 115
<212> TYPE: PRT
<213> ORGANISM: Eucalyptus grandis

<400> SEQUENCE: 87

Met Pro Cys Leu Asn Ile Ser Thr Asn Val Ser Leu Asp Gly Leu Asp
1               5                   10                  15

Thr Ser Ala Ile Leu Ser Glu Thr Thr Ser Gly Val Ala Lys Leu Ile
            20                  25                  30

Gly Lys Pro Glu Ala Tyr Val Met Ile Val Leu Lys Gly Ser Val Pro
        35                  40                  45

Met Ala Phe Gly Gly Thr Glu Gln Pro Ala Ala Tyr Gly Glu Leu Val
    50                  55                  60

Ser Ile Gly Gly Leu Asn Pro Asp Val Asn Lys Lys Leu Ser Ala Ala
65                  70                  75                  80

Ile Ala Ser Ile Leu Glu Thr Lys Leu Ser Ile Pro Lys Ser Arg Phe
                85                  90                  95

Phe Leu Lys Phe Tyr Asp Thr Lys Gly Ser Phe Phe Gly Trp Asn Gly
            100                 105                 110

Ser Thr Phe
        115

<210> SEQ ID NO 88
<211> LENGTH: 1521
<212> TYPE: DNA
<213> ORGANISM: Pinus radiata

<400> SEQUENCE: 88

```
ccttcaaaga caacagagaa agttatgcaa tatgctggca gctagctctt gggataatct      60
atttagcgat gggtttgtcg agaagttggg agcatttatt gtgaagcttc acagaaaaaa     120
```

```
tgtcgaatac atcaagcaca tgaagaagca atttgtgcca taggctatct ttagcctcat    180
ggatgttaaa ataatttctt tctttccttc cttcttcttt cttacccacc aaaacacaaa    240
ataatagttt caaattttga attttcaccc aattttatga aggacaaaa ttacttagag     300
tctttcactc tttaatttat attctacata agtacctaaa gaggctctcc gacaatcata    360
tgataccata aaagtaacct cgattagaga gcgcctctcc atacaatcat ttgattttcg    420
agttaaatca aaattatagg ctatttccaa atcaatctat cgtccaactg aaaatttcaa    480
atgaatggaa ccagcacgga gtttcgtagg aaatagaagt aataggtgaa agaagcatt    540
gtcgaatttg aaagaatacc ctacgttttc atttcaaaaa ccatggtttt ttgtaagagg    600
gattaagttg actcaaggtt gtagaaggtt gacataacaa tagcatgcag gcacaggatg    660
catgtagtgc ccgtaatttg gaccaaccta gtaagattgt cacccgtttc aaatgactgc    720
ctacaagtgc atgcaaaggc catggaagtt gatggttagt gaaaagatcc ggagagacga    780
ttattccatc atgcaatgca catcgcacgc ttgctttatt actcacacga ccaacgttcc    840
cttcatccac ggaattaatt tctctaatcg atccaataaa ccgccttcga tgtcgatttc    900
caaatgaatt aaatcgttac atgcccaccc gacttcacac atgctccctg cacgtgcaac    960
caaatccatt acgcccaccg ggcccggccc tgctcacaca tcttgcatcg cccaactact   1020
ctgattttac atgaatatca atactattcc ctccacttat aaaatggcca aacgccctgc   1080
ttagttctca aagcagatca gagcctttca agagcttccg caaagatttt ctttgcgagt   1140
aatttgatcg agaaggatgt ctgcatcgaa cggaactaat ggtgttgtcg cagtcaagtc   1200
tcgccgacag cacagacctg ggaaaacgac agccatggcg ttcgggaggg cgtttccaga   1260
tcagctggtg atgcaggagt tcctcgtcga tggatatttc cgcaacacga attgccagga   1320
ccccgtcctc cgccagaagc tcgaaaggct ttgcaagacg acgacggtga agacgcgata   1380
cgtggtgatg tcggatgaaa tattggcgca gcatcctgag ctggcagtgg aaggttcggc   1440
caccgtccga cagcgactcg agatctcgaa cgtggccgtg accgacatgg cggtggacgc   1500
gtgccgtgac tgcctcaaag a                                            1521
```

<210> SEQ ID NO 89  
<211> LENGTH: 2590  
<212> TYPE: DNA  
<213> ORGANISM: Eucalyptus grandis
<400> SEQUENCE: 89

```
ctgaaactgt cgctcggcga tgcataccaa aggctgaagg tatcagaatc taatgcagct     60
tatgtaaaag cgcgatcaat ttattgaccc cgacgacctt gactccatac ttcacgcctc    120
agctttgtgt tggatggtct tgacctctct caccctaaaa ggtagctcaa agaatgaga    180
ctttccgtca tacttataaa ccgaccacca gcctctttca caaccgacat gggacaacct    240
caaatagaat ttttaacaac acccttgcac gctctttcta tccactttat tatgccatca    300
catgagcgtt ttccacgcgt aaatcggcta ccacccactt tcacacggcg gcgaaacgag    360
aaaaaggtcc tacctttgac tccccccgcg tcccaaattc tcactcccga ccggtaaccg    420
agctcacaag tttcagcctt tcatcatcat cactcgaagg cagagagaag gacatacact    480
aaagacaacg aaacagtctc tccatcccgc catccgacac gatccacatt acggtacgga    540
acacatcccg cggagcaacc cgacgtccca aactcttcgc tgatcaaaac cagtccggtc    600
gactccgttt cgcgcggacg caacgtgaga gagggagaga gagagagaga gtaccggcga    660
ggggatgatg ctgtgcggaa gcgtcgtcgg gcgctctccc ggcgaacgcg tctctacatt    720
```

-continued

| | |
|---|---|
| ccggcgacgg cgacggcgac gaaggcgggg aggggaatgc cgcggggttt ctgcaacgac | 780 |
| ggaagctcac ggcattttc agagagagag agagagatgg cacgtcagag cgccattccc | 840 |
| ccacgcgacg ttccgccttc cggtattcct tccgggagaa aaagtgggca aattgcaata | 900 |
| gacaaaaaaa aaagaaaaa aagacggtc acccaaatta tttcttataa cacaaaaaat | 960 |
| cgtacctata aatatatct atcactaact tgtgcagtat gacaaattta cacatttacc | 1020 |
| tgaaactgtt tttataacat aaaaaattta aacattttc tgtgacaata aatgttcaca | 1080 |
| caaatataaa actgggattt ttatttcaat tacaaattta gaataaatgc gcaacataaa | 1140 |
| tacaaattta tgattttcg tgttggcaag aaagtttgag ataaatgtat cattgtaggt | 1200 |
| aaagtttaga gtttttttt atggctttta accaaaatgc acattttagt tccgagttct | 1260 |
| aaaagaaaaa ttactatttt cctttacatt tacttatgta ggtgtgtaat tataaatatt | 1320 |
| aattctcttt aggatttgta acaattcttt gagcttttgt tttgccttta ggccattaga | 1380 |
| attactaaaa agttaataat ataaacattt tttcgaccac ggtcaccatt catacctaac | 1440 |
| ttctaattat tgaaagattc tcgcatttga tcgaaatcca tttactctca taaatttgag | 1500 |
| gttttgaacg gtatctacca taagatcatg gtttattaca aaacacttat ggcgggtggc | 1560 |
| gcggacctgg cgagaatgtg gctactttaa tgatgaggat ttgagatatt ataccacgat | 1620 |
| ccataataat aaaggagcgc ggcaatcata tcttttttca tataaaggac gatttatttt | 1680 |
| ctatgctgtg agtatttgct cttggaatta taagatatta gagatcaaac ctatcaccaa | 1740 |
| cggtgatttg aaattaaaga agtccttgta tcacttacaa aaataaatat ataaaaaaag | 1800 |
| ctttcattgt gcacttgaat atttaaacat aaattattag tagtagataa tttttttaatt | 1860 |
| taactaataa tgagcactca ttttagaaa aatagttttc aaatcattca ttttctactt | 1920 |
| aaaaaaacca attgaccaac taattagta tctctcattc agttggtgaa tgaatgactc | 1980 |
| gcactctaac ccttcacttg gcgagtcatt ctgtgtagac cagtctctgc aaatctagcc | 2040 |
| atgctcatct agcaactacc ttcaagcgca agtactttgt catgtagacc aaacgttgag | 2100 |
| caacacggaa tgaatcctaa cgcacttgga aaacaatcaa tccacgctac gcaagctaat | 2160 |
| gctcacacaa gcatcatgat acccgaagcc gaaaatacat gagtcgaaag acatcgaact | 2220 |
| ccgccgtcct cgcgaatcat ccgaatcgca tgtcacgccg ctcgacttgg tagcttaacg | 2280 |
| agccttccag tacctgctgt ttaaatgctt tgtcaatgtg attcgaatcc tttcaaagat | 2340 |
| cctgaaagtg cagcttcaaa aatggcgtcg accaaatggg cttgcgttgc tgcaatctcg | 2400 |
| ctcctactga gcctaggatc gagcgctgct cagaggtctc tccttatgag cagcgccaac | 2460 |
| tggcaagagg ccggtgagcc gacggatctg gacttacgtg gaggaattgc cggaaccctg | 2520 |
| gggtcatcaa gtgagggcgg caccatggcc agctccgaca tgggcggttt tggccaggac | 2580 |
| atgcctggtg | 2590 |

<210> SEQ ID NO 90
<211> LENGTH: 1172
<212> TYPE: DNA
<213> ORGANISM: Eucalyptus grandis

<400> SEQUENCE: 90

| | |
|---|---|
| actctcacta attctttagt tttccaattt agccccttct gtaattgctc atcttcttta | 60 |
| ccaaattctc taatttggcc ggcgaagggc tgacaaggga ttggtcatgt caccctcacc | 120 |
| aaaggttgcc gaaggtccgg tgacctcagc tgacggccac ctacaccaaa tctagctcac | 180 |
| tagcagccta agcccttcat caactctagt gaaaggtttt gagtattttt taataaaaaa | 240 |

```
tatttaaaaa atatatagcg agagctcatt acaaaaaaat tttaaaaaaa aatctaaaca        300
ttacttgaac tcaaagtgac tttataaaga gttttttacca aaggatcttg gtttcatcat       360
ttgcactaca cccaaaaccc aatttctaag ttaaatcaaa cccactgtct aatagagata        420
aggtaaatgt tataaaccaa attccaaaat tccgaagcac taaatatatt tgctgatctt        480
ataatcgcca attgagaggg tctcattctc caagggattg tgacatatta gtaattgata       540
gggtctcatc cgtaggactc cgactcagcc gcgccacgtg actggatcgc tgaacggcgc       600
ggaaccagag gagcgtgatt acctaatatt ttctcctacc ttggccttga gattgaattt       660
cagaaaaaga aaagaaaaa ggaacaactt cgccgactgt tctataaaat gcatgcgcca        720
ccccgacccc cacccacgca tcacatccat ccagcctcca cgacagacgc ataaacacaa       780
cacacgtcgg ttagagagag agagagagag agagagagag agagagagat gcttggacag       840
ttgtcgcacg agacggaaat gaaggtggga gcaggcaaag catgggagct gtatggcacg       900
ctcaagctgg tcctgctggc caagcaggaa ttctctaata ccatctgcga cgtcttggaa       960
ggtgatggcg gcgttggcac cgtcatcaag ctcaattttg gaagtttatc ctatacagag      1020
aagtacacaa aggtggacca cgagcgccgc gtgaaagaaa cggaggcgat cgaaggtggg      1080
ttcctggaca tggggtctcg ctgtatcgat tgcgattcga agtgataggc aaggacgagg      1140
aggagtcgtt ccgttattaa agccccccccc cc                                    1172

<210> SEQ ID NO 91
<211> LENGTH: 446
<212> TYPE: DNA
<213> ORGANISM: Eucalyptus grandis

<400> SEQUENCE: 91
gggtgaaaac aattaatgag atcatttgaa ttaaggaaag tggaaaggcg gttttctgat         60
tggtacactg aaacaacagg aaggtggtgg aggccgcaat gatggaattt atccactttta       120
atcattttat gaaatcgata cactaacctt tgtttctcct aaacccaaag gcattaatcc        180
ctgtcctcct cactcgatct cgaaggccag aaggggggagg ccgagcctct tgcttttttt      240
cgtgtataaa agggcctccc ccattcctca ttttttcacca tcctccgttc gttcgttccc      300
ttccctttcc attgttgcgt ttaagccctc caattttctt ttggcgtccc gttttttgggg     360
ctcccttgaa gatctcctct tcatttcggg atttcctgcc ttcgccgcgc catttgaagt       420
tcttttttctg agagaagaat ttagac                                            446

<210> SEQ ID NO 92
<211> LENGTH: 2119
<212> TYPE: DNA
<213> ORGANISM: Pinus radiata

<400> SEQUENCE: 92
atcttattcc cacctcacat caataaattt tatacgattt taacatctctt aaaattaaaa        60
gaatcaagaa ggcatccagg tgataaagcc acgtccaata taaaatctcc tcggtggatc        120
ctttcaatcc agctacccaa tgcggcgaaa ataacgctga ttggactggg ctacactgta        180
atcacaaatt cccttccgtt tagatttcaa ctcgttgacc tacgagtatt ttatcgattt        240
aaaattatac aaaaaattgt ggaatgtttt acataagcaa aacttaaata atgtaaatag        300
cgatgatgct ttacttgtac ctaaaaattt cttccaaatt aaaccaaata tcaaatccta        360
gattgatgag ttccagtgga gtctgccatt ttatttcttt ctctctttca ttctttgcaa       420
cgaaaggaga aaatccttaa cacaattcga aaacgataat gattctggca aaagagaaaa       480
```

```
aaaacgtgaa gattagacac ttgttttgtt ttaaatgagc aatcacatgt gaatagagag      540
ggttttatgg gcctggtttt gtgtgcataa tttcttatga aagcgatgtg cctggagcgt      600
tgaagctcat agaacattgc aacaagagat cgagagtgtg ggttagaaaa ccgcaacaat      660 agttgtgtc gtgtttttct atattcagag gtgttgtgtg gtaaatatct ctggatttat       720
ctcgaatgcg tcacttttac agacacagaa gctcagcgga aaccctcaac gctttaaggg      780
ccataaattt gctcagtttt aaaaattgtt tgatttccca ggtttgaata ttttcttttt      840
gttatcggaa gtggctctgc cttatgagta tcatgttctt ggttttgtgt gggcgctta      900 ttgattcagg tatgtattat ttctagtcct tttatcagc ataggtggaa tgttctgtat       960
tttatatttt ggggccatac acatggaacc gttgtcatta ccatgcttta tagataatgt     1020
ctctctgaat tgttttat aggcttttgc ctcctacgca gattttaa ggaaaataca         1080 aagatatta gccaattttt gttgttgtga ccttgaattt ctaaaaaatt taatggattc      1140
gttttctaaa ttcctgattc gtcaaaggct gaagggcgcg atagtaatag aaaatggacg     1200
agagtttatc ttttcatggc tggacacaca gaatttgtgg agggggattct ccattctggt    1260 ttatccaccg ttagttctct ctgtactcca cccttagttc tctttgtact cgagaccttt    1320
aatgattaac cctgcttatg ctgtcagtac tgaactcact tccagagccc caaaaatctc    1380
tcccaagttt gccttatttc ttaaaataat tcacaagtag aaaatgagat ttttgcaatt    1440
ttgtaactaa catttcccgg tctcctctgt atgttttcac cccttaatgt aattgaaatt    1500
tgcacccggg ttagattcaa agcggagaat aacatcgggg ccttgttcta gacagagatt    1560
tttcacaaat aacaggttcg aaggtatgtg tagacatctg ggtagttgta gaataaagac     1620
ggagcccatt aggtggatcc aatcgaagaa ctcagatggg aaaacagata aaaattatcg    1680
ggtggacctt cctccacatg ttaattatat atcaagtgtc gccaatcctt atgtgaaaca    1740
tttagtaaag cttcgccaga gcacttctta taggcattct gtgggctctg ttgttgtggt    1800
tggaagtact cctttaaggg aggtatctga atatttgcaa cagaagtcag taaaacaagt    1860
ggttgactgt ctgttttgtac aagatgttac tggcatacct gtgggcttga tagagacttc    1920
caggcgcatt gtgcatgtaa atcatttggt gatgcagaag ctagccggag tagagtctat    1980
agagcccact gaagcaattg gtgtaatcaa gcttcctagc agcttctaca acttggaatc    2040
tcttgaaatc actctagttc ccagatatgg tgctcgtcgc cacatcgtct gcttgtactt    2100
gatggcattc aggatcctg                                                  2119
```

<210> SEQ ID NO 93
<211> LENGTH: 2571
<212> TYPE: DNA
<213> ORGANISM: Eucalyptus grandis

<400> SEQUENCE: 93

```
aaggtaactg gttcagcaga gcgcagatac caaatacttg ttcttctagt gtagccgtag       60
ttaggccacc acttcaagaa ctctgtagca ccgcctacat acctcgctct gctaatcctg     120
ttaccagtgg ctgctgccag tggcgataag tcgtgtctta ccgggttgga ctcaagacga     180
tagttaccgg ataaggcgca gcggtcgggc tgaacggggg gttcgtgcac acagcccagc     240
ttggagcgaa cgacctacac cgaactgaga tacctcagc gtgagctatg agaaagcgcc      300
acgcttcccg aagggagaaa ggcggacagg tatccggtaa gcggcagggt cggaacagga     360
gagcgcacga gggagcttcc aggggggaaac gcctggtatc tttatagtcc tgtcgggttt    420
cgccacctct gacttgagcg tcgatttttg tgatgctcgt caggggggcg gagcctatgg    480
```

```
aaaaacgcca gcaacgcggc cttttttacgg ttcctggcct tttgctggcc ttttgctcac    540
atgttctttc ctgcgttatc ccctgattct gtggataacc gtattaccgc ctttgagtga    600
gctgataccg ctcgccgcag ccgaacgacc gagcgcagcg agtcagtgag cgaggaagcg    660
gaagagcgcc caatacgcaa accgcctctc cccgcgcgtt ggccgattca ttaatgcagc    720
tggcacgaca ggtttcccga ctggaaagcg ggcagtgagc gcaacgcaat taatgtgagt    780
tagctcactc attaggcacc ccaggcttta cactttatgc ttccggctcg tatgttgtgt    840
ggaattgtga gcggataaca atttcacaca ggaaacagct atgaccatga ttacgccaag    900
ctatttaggt gacactatag aatactcaag ctatgcatcc aacgcgttgg gagctctccc    960
atatggtcga cctgcaggcg gccgcgaatt cactagtgat tggcccgggc tggtctggag   1020
tggccaccat cggcataatg actaggaacc cggaacatca actgatggaa gaaaagccga   1080
cattcctcat caagagctcc tctcactcct tccccactac tactataggg cacgcgtggt   1140
cgacggcccg ggctggtctg ctgtcatatt tgtatatgag gtcctatgta tgcttgctat   1200
gtgacctcct tcatgtatgc tgtgaagaga gtgtagcagt aacatggcca tctgcgaaat   1260
atggattcac cttaaaatct gatgattttc agaaaacgag gaaggtgctt gccgagaaga   1320
ttgcacagct caattcagct atagatgatg tatcctctga gctccgaact gaagaatcat   1380
cagatgagat tgctgttgcc cctgatgaaa ttgaagctgc tgtttgatgg cccaaacctc   1440
ccaggcctac gatcatggtc atcttctgtt ttggtgcaat tggctctacc tttttggtgg   1500
cctccatata acagaataat ggttcatatt gtaaatcttc tgtttatttt ctaaagacca   1560
atgcactcag tttcttttga tatgattgtc tcgattgagg aagtgcatca ttcgtggtat   1620
gattatgcag aataccattt aactcagcag actttgtacc gtatcatcgc agcttttccc   1680
ttcttgtgta tgcataaatc tagtccttca ttgaaggtga tcgccgttac agtctggata   1740
gtgtgtgcca tcagatggca ctacgattag tgtggttgac atggtgtcaa cttgaaagcc   1800
aattggtgac gatggtactt aatgtaagat tggcagatgg tgagaacgag atttttgctcc   1860 agaatggcaa agcaaggcta agttgtagcg aatcaaatga tctacgaacc atcctagctg   1920
gctgtgtgac cacacactga agttctattg aactaagcca gttatggatg atatgggagg   1980
agaaaattga gaaatccatc agatggagtg ttggccgtgt tgggcttttg tcgcaggccg   2040
atacttcgaa ttcaggcgta ttttttattcc tgactgccgc ctctcccgga aagggaaggc   2100
ggatattatt ctctgaacga tttccaccat caactccaca tcgatctcca agccagaaat   2160
atacacaccc caatttttctt ttaaatatat gggacatata tggtgtaggc tctcgcgcat   2220
gttaacacat aagctctctc aacaaaaatc tggctcgtgc ttttaaccga gaagttcacg   2280
agtcattgaa ggagtggcct ttaggggagg gagagagatg gattggtggt taaaatcagt   2340
ctgtggctca catttatacc gtggagatcc cccaacagca accttatccc attatatatc   2400
cccacaacac catattcacc actcgttcct tctaattggc ttccaaccat aattcacaga   2460
cacacatgta gtgaccaatg agaaaggaag aaaaatacag gctttcgaaa gctagtgcgg   2520
tataaataac ctgggaaaag caagccgctt gagctttagt ttcagtcagc c            2571
```

<210> SEQ ID NO 94
<211> LENGTH: 1406
<212> TYPE: DNA
<213> ORGANISM: Pinus radiata

<400> SEQUENCE: 94

```
aaagaggcgg aggaattgtc tagatggtca aaagtgaccg gaatctaagc aaaaaatttc     60
```

```
aaaaaatgtt gtaaaggtag cgtttgaatt gtgttttga tggtggaaat ggattcaacg      120
ccatcaaaaa cgtctaagac acctaaaatt ttgaatttta acaactatat cttggattta      180
caaaaatcct tgccggattt tctctaaact ccttcacctt acgcaaaaga tatatatttt      240
tttgtgtgat gttgtgcatt ataagtttga tagtgaagta atgatatata tcctttatgt      300
gatggatgat tgaataatga atatattaaa tgaaataaat aatgatggga taatgaatat      360
attatatgaa ataaatataa agtaaaatgc tattttttaa tggtgttaat gatgaattag      420
tatcatcctt aaataatttg ttagtgaatt attaaaatga tgagttagca tggtcgttaa      480
ataaattgtt agtgaattat tatatttata tatttcctta ttagaaagtt ttttttttgt      540
aaaagttttc cttgaacttc acccatattt aattatcaat aatttatatt taataaatga      600
tatatataac ttctagcaga atgacacgcg acttgtatat cttttcattt tttaacccat      660
gaaaaccgat tagggtattg caaattaggg cattgccatt caaataattc tcagatgaaa      720
gattctctct aacaattaca aatgattatt ttttccatg agtgttgcat gttcgaacgg       780
tctgcccagt ctgtgagaga gcatagagaa ccctccctgc ccaatttgtt agagcataga      840
gaaccctact gcatgagtag taagaaaaat attcggtctc aattcggcaa agaccacctc      900
gaatggatga cttcaacgac aatctcatga tagtgttctg atcagcacca gttcacctat      960
atattttatc tagggtttag tttgcatgta tcaatcctct ggtgcactag gtaattcttt     1020
cctagtatca tatatcctta atactgtttt gtctttaat ccatggctac catcagaaca      1080
agctcaaagc agaaatcggg agcatcagcc atcctcttgc ttatcgcgct tgcagggtta     1140
gtaaatgcgt gcaacgctgt gggtattgag ccaatgtgcg acactgtggt gtcgagtctt     1200
ctgaggcttc tgccatgcag gacggctgtt gatccctcaa ttgccgccat tccacttcca     1260
agctgctgca acgcggttga gtcagctggg cttcaatgcc tctgtctcgt cgttaacggc     1320
cctccttttc caggggtcga ccgcggcctc gcaatgcagc tgcctgccaa atgccatctc     1380
acccttcctc cctgtaacag ttagtt                                          1406

<210> SEQ ID NO 95
<211> LENGTH: 2546
<212> TYPE: DNA
<213> ORGANISM: Pinus radiata

<400> SEQUENCE: 95
ctggtagaac aagcagctca aggagcacca aggcacgagc ccactttgca tgttgtagac       60
taacgaattt tacattagaa taaaatatgt cgacaatatc gaggagatct tctccaaaat      120
ccaactcatt aatctctatt atgcacaaac gagtgatgtg tcgagactca tctgccaaca      180
agccatcaac atcaagaagg gaacggaata gagccaaagg gaaccctaga gaccctcatc      240
cacataataa tgaaatattc cacgtgtgtt tttcaaaatt tgaaaatttc atgtattttt      300
tggttgattg gttgtggtct ggttttttcc aaattcaatc tagttcaagt ttttggagtc      360
gaccagttgg gtaaccagtc taattctggt aacattgcat tgtacttgat ctcaataaaa      420
gcatatagga tagaattatc ttctgtcttg atggtttcca tgagaaccaa ctgctatact      480
atgaaaaata tcaatgttcc acaatatttt tgggacaagg gaacacaaga ttgagtcaac      540
agttcaggac cccagaaaaa ttattcctga gttcgcagat tattttccta aaagtgaaca      600
attcaagacc ctagccaaat cattcccaag tccaagttat gtgacactgc gactaacaag      660
gcaagttgga agaaaccatc aatcaatctc ctagttaatg acagtccttg taagaagttc      720
aagaagatta acaccagaag aggtcatgct gactgctttt atccaattct ctctgctctt      780
```

-continued

```
caccaacaga aatagccaag atggttgtac ccattcccta atctaattta ttatatgaat      840
ttctctttat ttttctacat ataaaaaaca aaaacttttc ttgatggtca aacagaaaag      900
gcagttcgat tggatttaaa catccaaata cctcccacag attgagaagg ccaagcccca      960
atccaacagt ccatgatata atatttattc aatcacactc aagataatgc aatgaaggtg     1020
caccacgcta ttagattctg cacagaactc agatgactgt aattatcaac tttaaccagg     1080
agtaatttaa aaactcaatt gtgcttcagc tatgtggaaa aactttggca ctggaaatgg     1140
tataaatgtt gttgaataag caaacatttt tcaagcactg aattcaaagt caagtcaaag     1200
gaacatctta cttgggctgt acaggaaatc tgaagtacaa aattagcgaa aaaacaggag     1260
aaagagagta gtcattacat gttataacat taccatatag gattttgtaa tacttcttga     1320
tatttcaact tcccgactga tgaaatgtat gccactacag aacaggtcag tcatgtatgt     1380
gagcaattag ccaaactagg tcctaaggtt caaccagtgc agacaacgct gtaactgaaa     1440
caaatttgtg ggacaattaa aaattctcta ccaggatagt tgtaccagta ggtgcccttt     1500
tcaaaccatg atttaaaaca caagggtggc ttaccacttg accaaatcat ttaataacca     1560
acccctcgaa catatcaaga aagaaaacat ctgcatataa gtaaattgaa agatgatatt     1620
taagaggcac tgccttaaat tttccatttg gacaaatcca cattgcttga taagcataaa     1680
accttggtta agagcaagtt tagggaacca tcaaatattt ctacatactt tacaatagtg     1740
tgtttataaa gctaatcaaa tgcttctatt taaatatata gcaacctaca caagaaattc     1800
actaggacag caatcacttg gccaatgtga ttaccaatat aaccatactt gaagagcata     1860
cataaatcac aaataatgat tcaattagaa atatcttaaa gataaactat tattcaatgt     1920
acatgttaca aagaacctca cctgtccgcc tttgaggagc aagtagacaa ctaaaagcgg     1980
aggttacatc ctgaactgaa cttgttctcc tctgttccaa gaacttgcat tgtattttga     2040
gtaacttcac tcgtgccgaa ttcggcacga gaaaacactt tgattgcttc cgcgggtggg     2100
ttttactttc tctggaatag ttagttccgc cgttttttgga agatttatca gaatggccaa     2160
aattcaggtg tcaaacggga gcgtcgtggt ggtggcggcg atgatattta tggtggcggt     2220
ggccatgcaa aaccatcacg tcgccgccca aagtgctgac tgcgcaccac cgcggagttg     2280
ctgagcccct gcgcctcggc ggtgggaaac aacccgcaga ccccactccc gaatgctgtg     2340
ctgttctcca gaccgccgat gtcgactgca tctgcgccct cgtcgaatca accataaaat     2400
tgccttccga atgtggtctt gacacccccc agtgcccaag cgactagatt ctcaagaccg     2460
tgactgagtg ttggtttcag agccagtaaa cattcattct gctaataaat gagtgtatgg     2520
agctttaata ttggaaaatg cttcat                                          2546
```

<210> SEQ ID NO 96
<211> LENGTH: 4726
<212> TYPE: DNA
<213> ORGANISM: Pinus radiata

<400> SEQUENCE: 96

```
gattactata gggcacgcgt ggtcgacggc cctggctggt cctaggacac cgtaatatat       60
aacctcgaca tggcttacaa agctttgact tgcattctca ttgggcttac aatggtgctg      120
ccaaaaatga aaagtacat atgtaccct gttgaaatga gcagtaatag gcttgaacaa       180
tagtgaattg ctacaaaatt atgaatgcct ttctttgctt gaatgtgggc taaggagaag      240
tgggatttac atttgacttg caaatcctaa gacttgtcta gagctaagcc tccgagggag      300
gaaccatctt acatagtctt gagtctagag cggagaagat agccaaattt gaaaggaaac      360
```

```
ttttatttat ggggagaagg caaacaactt gaggggaag gatgatcaat aagtagggta      420
agggaatcca caacagaggg cactaaggaa atggggtgt tagaattggc aactagggcc      480
aaattccacc ttgggatagc tctctggatg gagatgatga ttgcattaga ttcctctttt    540
cgagaggacc aagattgata taagatcat ctcatttgga caagcatagg tatgattttg      600
aatttatacc cactcatgca caatttttt aggtccgcca catcatcatg taggctcatg      660
aagcccaacg gacatgactc ttcgcccta tcgtcttgta taaatacaag tgtcctccca      720
cctcatttgg catcttcatc tcttacagat tctctcttct tccctcattg gttcttgcat    780
cattgggcat tctctctctc ccacgtgtgg cacaaggagg atgaaattac aagaccgaaa    840
ataatagaaa ttttgcaatt tgaccagcat tgaccatgac cttccaagca tcattcgact    900
tcaattttt tgggttattt ttgtctcaac aagccgcata ttttggcaaa aaaatcgagg     960
cattctgggc acttcgacta caaaccaaaa ttgtaggttg actgcaaatt tcaaatagtt    1020
tgactattga cattgtcact gttttcgatt gactttgacc tcctaattag gccgagtttg    1080
actagggag gctgatttgt tttaaggaca tttgattgat gctttgacta gcattgactt    1140
ttatagttaa ggttgaagtt tgactacagt tgactgcata aatttgcaga gatgttttga    1200
ctttgaattg ggcaagtcaa tttgaatttt gtactatctc tctattttga acatttgata    1260
taataataag aagattcgat caagggttt tccccgcatt gggtttttc cctggcatcc      1320
gccaaatctg tgttctctt gtctttgctt gtcttatgca ttttgtttca ttttctatct    1380
acttttactg tcaatgtgat tattgtcagt gttattggaa attggaaatt gtgattgggc    1440
tgctaaggaa cattgaagta aattgtgcta acaaagaac ataccattgt taacgaaaat     1500
taacaagggg gaaacacaga ggaatggttg caattgcaag attgtcattg attttgactt    1560
caagtgagga aggtcgcgtg gaggtcgcaa ggggagagga ataggagaga aggccctatc    1620
aacttgttca aggagagggg caatacaagg aatggaggaa ccctcaccaa tgaataatcc    1680
atgcacaaaa gtaatagaat gaacaaactt accacacgga agagcttcct tgttgccaaa    1740
agccttgcct ccgagacctg aatcctccaa tgcatcaaaa ttattgatca ttgaatcaac    1800
cacgattagg gccacttcct tggctaataa agcaattagt gtagcaaatt ctaaagctaa    1860
cttcaaagaa accttagctt tccaaaaaac aattgaaggg aggcaatgaa gatggcttat    1920
cacactaagc ctaaacatgc cccaccctat ggcatctaaa acatctaaaa gggattcact    1980
agtaatcgat cttttgtact tatgaaaat tcccatgaac caattcgatc tcttccaaaa     2040
agccatctat gaggtcaacc tcaacctggc tctaatgttg attgagcttg taatcctagc    2100
cctactccaa tcttaagaac caaccaattt tatttccaat tgattcaagg accctacac    2160
tccaaagaa gcaagggaag gccaaggaga atggcccaaa cttgagcaga gaataaggat     2220
tctctgtgag ggtcgaaact aacatcccat tcacgtaaaa tcaaaccaga gagacctcaa    2280
ctccaactct tcttaatgat gaagcacaaa tattatttg agtgaaattt gaaaccaaga    2340
aaacctctca ctaatatatg gaagaggggc aatattcaac cattggtacc caaatcgcct    2400
caagacactt accaagggag ccaaccaaac aatcttacca caaaaccaac caacagtgtt    2460
tttacccaca agctcttgga tggaatccag gataatgtct tcaccaacaa ccatcttatg    2520
tctatccttg caagcacaaa tgcattgagc tttagatttg gagtgcataa atacaggggg    2580
gtatccaggg gggggagggg gtttgctaga accccagact caccaaggca tgaagacaaa    2640
atgaggagag agggatctag attggggat gcaagttgat gaagcatgaa aaggcaatcc     2700
atcaccctgc atggcatatt tacgaaggtt gttcagagga atgagaacta atggatgaac    2760
```

-continued

| | |
|---|---|
| aacagctggt agaacaagca gctcaaggag cgccaaggca cgagcccact ttgcatgttg | 2820 |
| tagactaacg aattttacat tagaataaaa tatgtcgaca atatcgagga gatcttctcc | 2880 |
| aaaatccaac tcattaatct ctattatgca caaacgagtg atgtgtcgag actcatctgc | 2940 |
| caacaagcca tcaacatcaa gaagggaacg gaatagagcc aaagggaacc ctagagaccc | 3000 |
| tcatccacat aataatgaaa tattccacgt gtgttttca aatttggaa atttcatgta | 3060 |
| ttttttggtt gattgttgtg gtctggtttt ttccaaattc aatctagttc aagttttgg | 3120 |
| agtcgaccag ttgggtaacc agtctaattc tggtaacatt gcattgtact tgatctcaat | 3180 |
| aaaagcatat aggatagaat tatcttctgt cttgatggtt gccatgagaa ccaactgcta | 3240 |
| tactatgaaa aatatcaatg ttccacaata tttttgggac aagggaacac aagattgagt | 3300 |
| caacagttca ggaccccaga aaaattattc ctgagtttgc agattatttt cctaaaagtg | 3360 |
| aacaattcaa gaccctagcc aaatcattcc caagtccaag ttatgtgaca ctgcgactaa | 3420 |
| caaggcaagt tggaagaaac catcaatcaa tctcctagtt aatgacagtc cttgtaagaa | 3480 |
| gttcaagaag attaacacca gaagaggtca tgctgactgc ttttatccaa ttctctctgc | 3540 |
| tcttcaccaa cagaaatagc caagatggtt gtacccattc cctaatctaa tttattatat | 3600 |
| gaatttctct ttattttct acatataaaa aacaaaaact tttcttgatg gtgaaacaga | 3660 |
| aaaggcagtt cgattggatt taaacatcca aatacctccc acagattgag aaggccaagc | 3720 |
| cccaatccaa cagtccatga tataatattt attcaatcac actcaagata atgcaatgaa | 3780 |
| ggtgcaccac gctattagat tctgcacaga actcagatga ctgtaattat caactttaac | 3840 |
| caggagtaat ttaaaaactc aattgtgctt cagctatgtg gaaaaacttt ggcactggaa | 3900 |
| atggtataaa tgttgttgaa taagcaaaca ttttagaaca ttttttcaagc actgaattca | 3960 |
| aagtcaagtc aaaggaacat cttacttggg ctgtacagga aatctgaagt acaaaattag | 4020 |
| tgaaaaaaca ggagaaagag agtagtcatt acatgttata acattaccat ataggattt | 4080 |
| gtaatacttc ttgatatttc aacttcccga ctgatgaaat gtataccact acagaacagg | 4140 |
| tcagtcatgt atgtgagcaa ttagccaaac taggtcctaa ggttcaacca gtgcagacaa | 4200 |
| cgctgtaact gaaacaaatt tgtgggacaa ttaaaaattc tctaccagga tagttgtgcc | 4260 |
| agtaggtgcc cttttcaaac catgatttaa aacacaaggg tggcttacca cttgaccaaa | 4320 |
| tcatttaata accaaccct cgaacatatc aagaaagaaa acatctgcat ataagtaaat | 4380 |
| tgaaagatga tatttaagag gcactgcctt aaattttcca tttggcaaat ccacattgct | 4440 |
| tgataagcat aaaaccttgg ttaagagcaa gtttagggaa ccatcaaata tttctacata | 4500 |
| ctttacaata gtgtgtttat aaagctaatc aaatgcttct atttaaatat atagcaacct | 4560 |
| acacaagaaa ttcactagga cagcaatcac ttggccaatg tgattaccaa tataaccata | 4620 |
| cttgaagagc atacataaat cacaaataat gattcaatta gaaatatctt aaagataaac | 4680 |
| tattattcaa tgtacatgtt acaaagaacc tcacctgtcc gcctt | 4726 |

<210> SEQ ID NO 97
<211> LENGTH: 635
<212> TYPE: DNA
<213> ORGANISM: Pinus radiata

<400> SEQUENCE: 97

| | |
|---|---|
| aaattctatg aaaaaaatcc aatcatatta aaagtccaat tgattagcaa ttttatgaga | 60 |
| aaaatccaat tatgttaaaa gtcactgagt gtggccgaaa ttgtgaccga aattgaatgc | 120 |
| aataaccgag ggttttttcaa accaaggtta agcctctcat cattggggtg tgtatgaaaa | 180 |

-continued

```
tgtaatgggc atcgataacc ttttattaca acttcacgaa aattgcctct attcaatggg      240
tgtggatgaa aatgtaagtg cgcatcgata atggaaagcg atatgcagca aaatcaataa      300
acctgacttc ccatgtgagt gatgatttga tcgtacaact gatggtgtga agttactttc      360
agcttcacct tcgggcataa tcagggaagt agggccaagt tgcttagta tcactctaat       420 ccccaacacc gtgattacta tcttcatcaa caatggccac cttcgtcatt actttaactg      480
gtgggataca gctactttac aactgtaaat ttgttgaggc agcctatcct cagcctatac      540
atactaatta ttgcagctcg attaggtatc tgctgtgaga atagctgtgt atctctgcgc      600
tggttgcagg atccaagttc ctctcagagc cctcc                                 635
```

<210> SEQ ID NO 98
<211> LENGTH: 468
<212> TYPE: DNA
<213> ORGANISM: Pinus radiata

<400> SEQUENCE: 98

```
ctggtaaatt gagattccaa attattgatg cgaagcttcc tcgtggctgg tcggtgctgc      60
tggcatccaa accctaaatg aaaaagaaaa aggtgtccgg acggattttt ttagtatttt      120
tttcttattt tttttatgaa ccgtcggatt cgagatcgga cggcgatccg aaactgcaag      180
cgtcggccgt cggatgcagc atcggacggc aagaaggaa ccctaaaacg cattgcaacg       240
tgcttggtgg gtggagggtc tatggccagt atatgttgat aacaagggag aggaagtagt      300
cctcttcatc tagtgcgagt ctctctgctt ttctacgccg ctgcgaagct gttctgtggt      360
gtttctgatt ctccagactc aggcagtcgt ttttgtaaga gaatttagtt catcatggga      420
aaggagaaaa cccatatcaa cattgtggtt attggccatg tcgactcc                   468
```

<210> SEQ ID NO 99
<211> LENGTH: 222
<212> TYPE: DNA
<213> ORGANISM: Pinus radiata

<400> SEQUENCE: 99

```
atccaaaccc taaatgaaaa agaaaaaggt gtccggacgg attttttag tattttttt        60 tcttattttt tttttatgaa ccgtcggatt cgagatcgga cggcgatccg aaactgcaag      120
cgtcggccgt cggatgcagc atcggacggc aagaaggaa ccctaaaacg cattgcaacg       180
tgcttggtgg gtggagggtc tatggccaga tatgttgtaa tc                         222
```

<210> SEQ ID NO 100
<211> LENGTH: 597
<212> TYPE: DNA
<213> ORGANISM: Pinus radiata

<400> SEQUENCE: 100

```
aaatgaggca gctaactatt tatttggttt tggcttcact gacttgttcc ttagtgtatt      60
aatgaacaat ctctttagac tcagagatgg tgagaaagat tctatgagaa atattcttgt      120
tattgcttcg actcatatcc cccaaagagt ggatccagct ctaatagctc caaatcgatt      180
agatagatcg atcaatattc gaatgcttgt tatcccacaa cgacaaaggg aatttcctat      240
tcttttatgt agcaaaggat tatactcggg aaaatgtccc gatgaatttg gatctataac      300
catagattat gatgcacgag ctctattagc tcaggcctct ctgctgctcc ttggattgca      360
atctcattct ctgatttgcc gtgctgtttg ctctgctcac ttcagcccag atggagacct      420
tcttgttcac atcggagtct gtaaatgagg gacacccaga caaactctgt gaccagattt      480
```

```
ctgatgcagt gttggatgca tgcctcaccc aggaccccga cagcaaggta gcatgcgaga    540
cttgcactaa aacgaacatg gtcatggttt ttggtgaaat caccaccaag gccgatg      597

<210> SEQ ID NO 101
<211> LENGTH: 669
<212> TYPE: DNA
<213> ORGANISM: Pinus radiata

<400> SEQUENCE: 101
cctggaaatg ctatattaac tcaacaaagg attttcagcc aatcacaatt tgacaggttt    60
gaaatgaaag attacaggca tttccaatgg aacagaatat aattacttta ttccctcaaa   120
gtatcgtata aaataaatct tttgctccac acactttgga aaatacattt tcaacaatgc   180
accgacaaac tttttctacc acgttatgga accatacaag ttaaatttaa acacgaatta   240
cgcgtatatt tctaataaat cgatggttga gattgaatgc cgtgggcgat tctcacgcgt   300
ccgattggga tcactagtcc atcactcatg gtctgcattg cctttaaatt ggcggggcga   360
ggaaagacca atgcgtcatt ggtgtagacg agctctatta gctcaggcct ctctgctgct   420
ccttggattg caatctcatt ctctgatttg ccgtgctgtt tgctctgctc acttcagccc   480
agatggagac cttcttgttc acatcggagt ctgtaaatga gggacaccca gacaaactct   540
gtgaccagat ttctgatgca gtgttggatg catgcctcac ccaggacccc gacagcaagg   600
tagcatgcga gacttgcact aaaacgaaca tggtcatggt ttttggtgaa atcaccacca   660
aggccgatg                                                           669

<210> SEQ ID NO 102
<211> LENGTH: 230
<212> TYPE: DNA
<213> ORGANISM: Pinus radiata

<400> SEQUENCE: 102
atccacctcg gaatgaaatc actatgcaca ctccaccttt tttttggctt cttttctcgt    60
tgcctttacc atcagaatca agcacgaaga gtaaatatca cccatgcttt acaagtgggt   120
tggtagcatt agcgattccc ttcaccaaat gaacccttty ctggtgatga gtggacaacc   180
taaagttgtt tgctggtgat gagtggacaa ccagagtggg ggttggggaa                230

<210> SEQ ID NO 103
<211> LENGTH: 596
<212> TYPE: DNA
<213> ORGANISM: Eucalyptus grandis

<400> SEQUENCE: 103
actttgaaag ggtctcgagt caaagtgctc aaattgagag ggagaatttt agaacaaaat    60
cagatttgga gaatacatgc cattttaggg ggattttggg gatttcgcat atggcgtcgc   120
gtcgtcggcg ccttcttctt tacagattgt atcctcccat taaccgcgtg gacctgcact   180
gtaaccccga aacggtgggg gccaatttcg tctttccgcc tcctccactc agcttcgtgg   240
aagattaaaa tcctcaccgt ccgtgcaaac gccacgtggc gcgttagttt gcgcgtggaa   300
aggtcctcac gaaccgtaaa gggcaaaaaa aagggaaaat aaaaaaggag gaggaggagg   360
gaggaggaag aattgtccga ttgaaaataa gagtgcggtg gtgtggtgtg ggtagatctt   420
gaattgaacg agctcaatcc gcgtatttaa acccgccccg cttcctcatt cttccttgtc   480
catttcaact ctccctctct ccctctcttc tgccctcga tcgatccagc gatcttccta    540
tttccggacg cggggagcag ctcctcttgt cgaaggttct aaattagtgt ggagag        596
```

<210> SEQ ID NO 104
<211> LENGTH: 653
<212> TYPE: DNA
<213> ORGANISM: Eucalyptus grandis

<400> SEQUENCE: 104

```
aaaattttcc tttattttct tttcattaaa aagataaata aataaaaaaa aaaaagaagg      60
aaaacacatc gaggtgaggc ttaaaggtgc taggcaagga ccaccaagcc tacacaaggg     120
tcggcgaccc tcaccaatgc tggggcgagg gtgagcaacc ctcatccaaa tctggagagg     180
gttgtcactc gagaaagggt cactggccct cccctaaccg ctactaacat cgttggcctt     240
cgtcaccacc gcactaacaa tgggccacta attttatatt tttcgtgata ttaatcctat     300
taaaaatgaa atatctcct taattaatta agcttgtcag gaccgatgta aacaaaatta      360
atgtaaatgg acgcgccttt gacttgccaa caaactcgaa acgacgtttc ctccgtctga     420
taactatctc gcgacctccg acgacatccg acggtgcaga tcgggtcccg gtcaaccatc     480
cagatccacc cgattttctc ccggccctcg acaactccca ccaccacctc tttcctccct     540
cttccttcc ttcctttctc accagatttt cccgagaaaa tcacagagag agaaagaaaa      600
acctcaccgc ctagagagag aaagagagaa agagggaaga gagagagaga gag            653
```

<210> SEQ ID NO 105
<211> LENGTH: 342
<212> TYPE: DNA
<213> ORGANISM: Eucalyptus grandis

<400> SEQUENCE: 105

```
agttgggtaa ccagtctaat tctggtaaca ttgcattgta cttgatctca ataaaagcat      60
ataggataga attatcttct gtcttgatgg tttccatgag aaccaactgc tatactatga     120
aaatatcaa tgttccacaa tattttggg acaagggaac acaagattga gtcaacagtt       180
caggacccca gaaaaattat tcctgagttc gcagattatt ttcctaaaag tgaacaattc     240
aagaccctag ccaaatcatt cccaagtcca agttatgtga cactgcgact aacaaggcaa     300
gttggaagaa accatcaatc aatctcctag ttaatgacag tc                        342
```

<210> SEQ ID NO 106
<211> LENGTH: 342
<212> TYPE: DNA
<213> ORGANISM: Eucalyptus grandis

<400> SEQUENCE: 106

```
ggtctggaag ctcatctctc caatttggtg aagattacag ctataagagg tagctatgat      60
gtgctggcca aatgcaagtg atgaaatacg tggaccacca agtgcgaagg cattcgaaga     120
acgagggtcg aatttatagt gggcgaagga tgattaggtg gaatatgaca agaaaatagg     180
tttgaaagag aaataaatat tatgatagtg aagggtcttc acatggttag tttgatctgt     240
ccgagggtgt ccacccttgt ctgatccgca attgctcttg gtcgtgctga attttagagt     300
gtagccaaag taagaatttt cctttcactg tccggacatt tc                        342
```

<210> SEQ ID NO 107
<211> LENGTH: 948
<212> TYPE: DNA
<213> ORGANISM: Eucalyptus grandis

<400> SEQUENCE: 107

```
ctgacaaatg caaatatcta aaaccattgg ttgtttggtg cttgcaagtc tggattaccc      60
```

-continued

```
cactttatgt tcacctttc aataatgaat aacaaggtac tcgggaaaaa aaggaaaggg        120
aaattcgcac aaccaaagtt gctatgcaga agtcaactca atcctaatca agttgatgag        180
agtgttgggc cctattttct gcagcaaaca tgaatctcga ttcatctccc tcgcaaaaga        240
taaggaagct gcaaaagctt tcctcctaag tttgttggca agcaaattga ttttgtacca        300
gaaataaata caaagtgaaa cccaagcaat cacgcatggc ctgatttgtg ccatgtccat        360
ttgatctccc tctactattt ttcctgcttt ctcaagcaaa ctagttgctg taacagtgaa        420
tgatcccccg gctctctctc tctctctctc tctctctctc catttattcc atccatgttt        480
ttgcttttcg cacaacactt atcattgagg tgctaactac tgaattcccc taactaaaaa        540
ttggaacctc tcacctaatt tcattttctc ccactttgat gagcaccact ctctttccca        600
gatttcaaat aaattgccac tctctccctc ctctttcctc acacaaccaa aagccttctt        660
caagtaccac ttcttcactg tcctctcttc acaatccccc tcttaccaag agcaaagcaa        720
aaaacatgat gaagagactg tcatttctgc tcctactggt cctgctcttc caatgctcta        780
ccaccttggc tcagcctgcg gccgcccag ctccgcctgt gatagccccg gctgcacctg        840
ctacgcctgc cttaggcccg gctcctcctg tcttaggccc agctcctgca ggcccaaccg        900
acatcacgaa ggtcctcaag aaggtgagcc aatttacggt gctgctca                    948
```

<210> SEQ ID NO 108
<211> LENGTH: 362
<212> TYPE: DNA
<213> ORGANISM: Eucalyptus grandis

<400> SEQUENCE: 108

```
ccatcactca taatcaacaa ggatatctca tcatgtcttc caaccaaatt aaacccaga         60 catctctaaa gcagtatgga aaagaaaaca gtccggaagt ctctagctca aaaactgtaa       120
ccccgaccta attccggttg tctctgatta catcaattct tatgtcttaa cactccattc       180
gcacctccac aataaataga tcggcccttc atctcccctt accatcgaat ccaatcccaa       240
aaacacttgc tcagacacca tcaaatcctt cgcaaagtct ttttcttaca aaaaacaaac       300
gaaagcaacc atgaagcacc agttcattgt tctggctctc ttattcctca tcaacacagc       360
cc                                                                     362
```

<210> SEQ ID NO 109
<211> LENGTH: 326
<212> TYPE: DNA
<213> ORGANISM: Eucalyptus grandis

<400> SEQUENCE: 109

```
aaaaattaca atcaatggtt atcaatggat gttacaaagg gaggttacat atagaggtta        60
taaaagaggg ttacaaatag atgtctcaaa caattaccaa gcggttagat tgactccact       120
attttgacgg ttctccttgac tttactatct caacgattac tttatttcat catgttgacg       180
gttgcatcca tgattgttga cttcactttt tgtcgattcc ttcaagctgc tgattcttca       240
agttgccaat aattttattc ataaatgacg aaactctagc ctcatccatt aagtttgtta       300
cttgtccaca ataattaaat tcggta                                            326
```

<210> SEQ ID NO 110
<211> LENGTH: 296
<212> TYPE: DNA
<213> ORGANISM: Pinus radiata

<400> SEQUENCE: 110

```
tgctcccggt catgacaccg ccattctcgc tcttcatttc caattcaaat cacttggttg    60
ttgttcacac acacgggtct ttatatgacg agtgctgctg cgattataaa tagacggggc   120
aattacaaca aaaactcaca gcatttgaag gaagttggag tggtagagtg agaaatacac   180
agcctaatct gaaggaagtt cgagtaatag agtgagaaat ggatcttctt ctcctcatga   240
tgatgcttgt gatgatgggt gtagcaatgc ctactcattc tcaacaaatc actagt       296
```

<210> SEQ ID NO 111
<211> LENGTH: 723
<212> TYPE: DNA
<213> ORGANISM: Pinus radiata

<400> SEQUENCE: 111

```
cgttttacgc gggaacaatg aaaacagtac aatcgaaaga gtcaagtcgt gaggttcatt    60
tcgatgaagt tcccagagat tgtctcgttc aacgtttcct ctttttttcgg gtcaagtcgg   120 gtacagaaga ccactttctt tacgcggtca agacaccgcc attctcgggt caagtcggga   180
ggtccctcct gctcttcctt tttccaaatc cgtaaaattt acagattttt ttaatgtatg   240
aagcccactt tctttatgcg gttgctccca gtcaagacac cgccattgtt gttcacacgc   300
acgggtcttt atatgacgag tgctgctgcg attataaata gacgggcaa ttacaacaaa   360 aactcacagc atttgaagga agttggagtg gtagagtgag aaatcatttg aaggagttg    420 gagtggtaga gtgagaaatc atttgaaggg agttgagaaa tatattggga atctctcttt   480
tttgcagcaa ttagatcttt cctttaatgc tttgagtggg agaattccga cagagttggg   540
gaacctctct cttttgcggc aataagttgg agtggtagtt ggagtggtag agtgagaaat   600
acacagccta atctgaagga agttggagtg atagagtgag aaatggatcg tcttcttctc   660
ttcatgttga tgcttgtgat gatgggtgta gcaatgccta ctcattctca acaaatcact   720
agt                                                                  723
```

<210> SEQ ID NO 112
<211> LENGTH: 1301
<212> TYPE: DNA
<213> ORGANISM: Pinus radiata

<400> SEQUENCE: 112

```
actatagggc acgcgtggtc gacggccctg gctggtagcg acagagctgg ttcagtgacc    60
gttcgtgatt agccgcagta aaacaaaacc ctaaccgtaa ccctttcgcg cagattccat   120
ccttccccgt cctaccaaaa cccaaacttc ttgcccgaac tcaccttcta tgtattaatt   180
cttattatta tttaataata ataaatagtt aaacataaat ttataaatta attaattttt   240 atgatttta ttttagttta aaaatgtgac attgttatag attaatgctt atgaacgttt    300
attggccata attaccctaa ttaattataa ttaaaatata tagttataat taaaaaattg   360 tatatttat aaattgaatt aagaatttct gatgatattt catcattcaa ttccatctta    420
tcaaagttag agggaatagt taaccatgta ctagatctat tcatagctaa catttgccaa   480
gttcgtacta ggagacttgg atttttttta aaacataatt ttggcagtaa aaagtgaatt   540
ctattgtttt gaaaacaaaa caaaatacag gaagcgtgat tgtgggggttg ttgttgaact   600 tgcccgggca aaagaagaat gattagcggt agaggagtta gtagttacgt tcaactaaat   660
gcgtgactaa attatttatc ctccgccatg aagcaggtg attcacacac aacttgctgc    720
acacattgct ctcaaacctt tcctataaat atccgtagca ggggctgcga tgatacacaa   780
cgcatttaat caaactactt tgattacttt ctgtgggttc tactttcttt gaatagtcag   840
```

-continued

| | |
|---|---|
| ttctgctgtt tttagaagat ttataagaat ggccaaaatt caggtatcaa acgggaacgt | 900 |
| cgtggtggtg gctgcgatgt tatttatggt ggtggtggcc atgcaaaacc atcacgtcgc | 960 |
| cgcccaaagt gctgactgcg ccgccaccgc ggagtccctg agccctgcg cctcggcggt | 1020 |
| gggaaacaac ccacaggatc ccactcccga atgctgtgct gttcttcaga ccgctaatgt | 1080 |
| cgactgcatc tgcgccctcg tccaatcaac catgcaattg ccttccgaat gcggtcttga | 1140 |
| gactcctcag tgcccaagcg actagggtct caagaccgtg actgagtgct ggtttcagag | 1200 |
| acagtagaca ttctgcctaa taaatgattg tatgagagct tttatatatg gaattgctca | 1260 |
| tatgcttttcc tagatatgaa attattaaat tccatatgct t | 1301 |

<210> SEQ ID NO 113
<211> LENGTH: 3070
<212> TYPE: DNA
<213> ORGANISM: Eucalyptus grandis

<400> SEQUENCE: 113

| | |
|---|---|
| agcaccatca gcaaaaaata gatgggatag agtgggacac cacctgttca gtttgattcc | 60 |
| cttgagatga cctacagtga tagcttgatg aataagatgg gataatagat tcaccagagg | 120 |
| gataaaaagg tagggagata ggggatctcc ccgtctgatg cctcgggtag gttgaaaata | 180 |
| aggcaaaagt tcgccgttga atttgacagc aaaagacacc gtcgttatgc attgcatgat | 240 |
| ccattgtacc catgtagggt gaaatcctag agtgaggaga tagtccttta gaaagtccca | 300 |
| ttccacccta tcataggctt tctgcatatc cattttaaga acagcccgga attgacgtct | 360 |
| acattttctg actttaaatt gatgtagaac ctcttagact attaaaatat tgtcctgaat | 420 |
| ttgacgtcca ctgacaaaag cgcttttgctc ctggaaaata agtacaggca ggtagggctt | 480 |
| aaggcgattg gcaatcacct tagaaatgat cttatatgcg taattacaaa gactgatggg | 540 |
| gcggtattgg tctaattgtt caggatgtgg taccttgggt attagggcta tgatggttcg | 600 |
| attgagattc ggtggtatga tgccagaatt aaaaaagtgc tgcactgatg agaatagttc | 660 |
| atcctggagt atatcccaat gatgctggta gaagagtcca ttcaagccat ctggaccggg | 720 |
| ggccttggta agtcccagtt ggaaagtagc ctctctaact tccttcttgg taacaggagc | 780 |
| tattagggac atattcatct cattagtaac aacctaagga cactggttca gaataggcaa | 840 |
| gtagtctcga tgtcccactg tctgaaatag atgtgaaaag taacctatcg tcatcatctt | 900 |
| caaaatttca ggatcgcgca cccaagcttg attgtcatcc tgcaacatac taatcttgtt | 960 |
| tcgttgttgt ctttgtatag ttgttgcatg aaaaaattta gtattttttgt cccccccagct | 1020 |
| gagccatttta attcgagagc acatcgccca aaattattct tcttgctgcc ataactgtcg | 1080 |
| aattttctct tttaggtaag taaccaatga tgcgccatgt tgacaaaaag gctgattagt | 1140 |
| atgatcttgg agttgttggt gcaaatttgc aagctgacga tggcccctca gggaaattaa | 1200 |
| ggcgccaacc cagattgcaa agagcacaaa gagcacgacc caacctttcc ttaacaagat | 1260 |
| catcaccaga tcggccagta agggtaatat taatttaaca aatagctctt gtaccgggaa | 1320 |
| ctccgtattt ctctcacttc cataaacccc tgattaattt ggtgggaaag cgacagccaa | 1380 |
| cccacaaaag gtcagatgtc atcccacgag agagagagag agagagagag agagagagtt | 1440 |
| ttctctctat attctggttc accggttgga gtcaatggca tgcgtgacga atgtacatat | 1500 |
| tggtgtaggg tccaatattt tgcgggaggg ttggtgaacc gcaaagttcc tatatatcga | 1560 |
| acctccacca ccatacctca cttcaatccc caccatttat ccgttttatt tcctctgctt | 1620 |
| tcctttgctc gagtctcgcg gaagagagag aagagaggag aggagagaat gggttcgacc | 1680 |

```
ggctccgaga cccagatgac cccgacccaa gtctcggacg acgaggcgaa cctcttcgcc    1740
atgcagctgg cgagcgcctc cgtgctcccc atggtcctaa aggccgccat cgagatcgac    1800
ctcctcgaga tcatggccaa ggacgggccg ggcgcgttcc tctccacggg ggaaatcgcg    1860
gcacagctcc cgacccagaa ccccgaggca cccgtcatgc tcgaccggat cttccggctg    1920
ctggccagct actccgtgct cacgtgcacc ctccgcgacc tccccgatgg caaggtcgag    1980
cggctctacg gcttagcgcc ggtgtgcaag ttcttggtca agaacgagga cggggtctcc    2040
atcgccgcac tcaacttgat gaaccaggac aaaatcctca tggaaagctg gtattacctg    2100
aaagatgcgg tccttgaagg cggaatccca ttcaacaagg cgtacgggat gaccgcgttc    2160
gagtatcatg gcaccgaccc gcgattcaac aagatcttta ccggggaat gtctgatcac    2220
tccaccatta ctatgaagaa gatactggaa acatacaagg gcttcgaggg cctcgagacc    2280
gtggtcgatg tcggaggcgg cactggggcc gtgctcagca tgatcgttgc caaatacccca   2340
tcaatgaaag ggatcaactt cgaccgcccc aacggattga agacgcccca cccctccctg    2400
gtgtcaagca cgtcggaggc gacatgttcg tcagcgttcc aaagggagat gccattttca    2460
tgaagtggat atgccatgac tggagtacga accattgcgc gaagttcctc aagaactgct    2520
acgatgcgct tcccaacaat ggaaaggtga tcgttgcaga gtgcgtactc cctgtgtacc    2580
cagacacgag cctagcgacc aagaatgtga tccacatcga ctgcatcatg ttggcccaca    2640
acccaggcgg gaaagagagg acacagaagg agttcgaggc attggccaaa ggggccggat    2700
ttcagggctt ccaagtcatg tgctgcgctt tcggcactca cgtcatggag ttcctgaaga    2760
ccgcttgatc tgctcctctg tggtgatgtt catggttctt ggatttgaaa ggtcgtgaag    2820
gagccctttt ctcacagttg gcttcggcat accaagttct tctcataaaa ggaaacaata    2880
agaagcgact gtatgatggc gcaagtggaa gttacaagat ttgttgtttt atgtctataa    2940
agttttgagt cttctgcata ctgatttcac agaatgtgta acgaaacggc gtatatggat    3000
gtgcctgaat gatggaaatt gtgatattct gtcttctttt tcagtaaatc acttcgaaca    3060
aaaaaaaaaa                                                          3070
```

<210> SEQ ID NO 114
<211> LENGTH: 1227
<212> TYPE: DNA
<213> ORGANISM: Pinus radiata

<400> SEQUENCE: 114

```
aaatttcaag aggaagagat taattctttt aatttataaa attatataat aaaatatttta     60
tatttaattt agatgataag tttatgaggt gtagaataga tagtgatggg tgtattattg    120
agttattccc ctaatgtgga gacaattgat tagaagttct atgagaaaaa tccaatcatg    180
ttaaagtgac ccctaatgtg aagacaattg attagaaatt ctatgaaaaa aatccaatca    240
tattaaaagt ccaattgatt agcaatttta tgagaaaaat ccaattatgt taaaagtcac    300
tgagtgtggc cgaaattgtg accgaaattg aatgcaataa ccgagggttt tcaaaccaa     360
ggttaagcct ctcatcattg gggtgtgtat gaaaatgtaa tgggcatcga taaccttta    420
ttacaacttc acgaaaattg cctctattca atgggtgtgg atgaaaatgt aagtgcgcat    480
cgataatgga aagcgatatg cagcaaaatc aataaacctg acttcccatg tgagtgatga    540
tttgatcgta caactgatgg tgtgaagtta ctttcagctt caccttcggg cataatcagg    600
gaagtagggc caagtttgct tagtatcact ctaatcccca acaccgtgat tactatcttc    660
atcaacaatg gccaccttcg tcattacttt aactggtggg atacagctac tttacaactg    720
```

| | | |
|---|---|---|
| taaatttgtt gaggcagcct atcctcagcc tatacatact aattattgca gctcgattag | 780 |
| gtatctgctg tgagaatagc tgtgtatctc tgcgctggtt gcaggatcca agttcctctc | 840 |
| agagccctcc atggaagcgc agtcagtttc agttgttgag cagcgccccc atgccctact | 900 |
| attttcattt ccgttacagg gccacatcaa gcctttcatg aacttggcca agattttgtc | 960 |
| cagccggggc ttctatgtca cttttgccag taccgaattt gttgtaaagc gcctcgcaga | 1020 |
| atgtggtgaa agtatcgccc atcgtgattc gatggtgtgc agcagaacg atgatgtatg | 1080 |
| taacataaaa tttgaaacag tgcccgacgg actgcctccc caccacgatc gcagtactca | 1140 |
| gaatcttgcg gagctcttcc aatccatgga agagaacgct catattcact tccacaagtt | 1200 |
| gatggagaag ctccagaatc ttcggga | 1227 |

<210> SEQ ID NO 115
<211> LENGTH: 1169
<212> TYPE: DNA
<213> ORGANISM: Eucalyptus grandis

<400> SEQUENCE: 115

| | | |
|---|---|---|
| ttcattatat gattattacg tcataatgat cgatttctag aaatttggag acatatgtaa | 60 |
| attcaggagg aatttcaaga aacgcgcgtt actttgaaag ggtctcgagt caaagtgctc | 120 |
| aaattgagag ggagaatttt agaacaaaat cagatttgga gaatacatgc cattttaggg | 180 |
| ggattttggg gatttcgcat atggcgtcgc gtcgtcggcg ccttcttctt tacagattgt | 240 |
| atcctcccat taaccgcgtg gacctgcata gggcacgcgt ggtcgacggc ccgggctggt | 300 |
| ttcattatat gattattacg tcataatgat cgatttctag aaatttggag acatatgtaa | 360 |
| attcaggagg aatttcaaga aacgcgcgtt actttgaaag ggtctcgagt caaagtgctc | 420 |
| aaattgagag ggagaatttt agaacaaaat cagatttgga gaatacatgc cattttaggg | 480 |
| ggattttggg gatttcgcat atggcgtcgc gtcgtcggcg ccttcttctt tacagattgt | 540 |
| atcctcccat taaccgcgtg gacctgcact gtaaccccga aacggtgggg gccaatttcg | 600 |
| tctttccgcc tcctccactc agcttcgtgg aagattaaaa tcctcaccgt ccgtgcaaac | 660 |
| gccacgtggc gcgttagttt gcgcgtggaa aggtcctcac gaaccgtaaa gggcaaaaaa | 720 |
| aagggaaaat aaaaaaggag gaggaggagg aggaggaag aattgtccga ttgaaaataa | 780 |
| gagtgcggtg tgtggtgtg ggtagatctt gaattgaacg agctcaattc gcgtatttaa | 840 |
| acccgccccg cttcctcatt cttccttgtc catttcaact ctccctctct ccctctcttc | 900 |
| tgcccctcga tcgatccagc gatcttccta tttccggacg cggggagcag ctcctcttgt | 960 |
| cgaaggttct aaaattagtgt ggagagatgg tgaagatctg ctgcattggt gctggctatg | 1020 |
| tcggcgggcc tactatggcc gtgattgctc tcaagtgccc gtcagtagaa gttgcggtcg | 1080 |
| ttgatatttc tgtctctcgc atacaagcct ggaacagcga acagctccct atctatgaac | 1140 |
| caggccttga tgcggtggtg aagcaatgc | 1169 |

<210> SEQ ID NO 116
<211> LENGTH: 947
<212> TYPE: DNA
<213> ORGANISM: Eucalyptus grandis

<400> SEQUENCE: 116

| | | |
|---|---|---|
| ggtctggaag ctcatctctc caatttggtg aagattacag ctataagagg tagctatgat | 60 |
| gtgctggcca aatgcaagtg atgaaatacg tggaccacca agtgcgaagg cattcgaaga | 120 |
| acgagggtcg aatttatagt gggcgaagga tgattaggtg gaatatgaca agaaaatagg | 180 |

```
tttgaaagag aaataaatat tatgatagtg aagggtcttc acatggttag tttgatctgt      240
ccgagggtgt ccacccttgt ctgatccgca attgctcttg gtcgtgctga attttagagt      300
gtagccaaag taagaatttt cctttcactg tccggacatt tcgattgcta catggaccat      360
cccgtgtcta cccattcttg agaaccttcg agtggaaagc atgaataacc caccttgtac      420
tatataggtt gccgaatatg cctagggcgc gaccatcatt gagacggagt tggggtgctc      480
cgctcggttc accaccacca ccaccaccac caccaccacc accaccattg ggcactgata      540
tagcgactcc accactaccc caaccgaggt tggcaaactc tagattgtac atgggatata      600
tcggagtagt tgaacatgat cagatcaatg gtagtggtta agactctaga aattattgaa      660
gcaatatgtt aaatcagata cgtgtgagaa agtgacttac taattgctat ggctttcatg      720
atacttaaac ttcaatgaat tggtaatgtg aagagcaatg tgatctccac aaatactact      780
agaaggccaa gtccttttct ttatgccgaa gtcctaaagt ttaatatttc aactctacct      840
atatcaaatt tgtatgcaaa ttgcataatc gcactgattt ctatggtttt attaatctag      900
ataagaactc tctccaagac attaactaat taagattgac cccattt                    947
```

<210> SEQ ID NO 117
<211> LENGTH: 1766
<212> TYPE: DNA
<213> ORGANISM: Eucalyptus grandis

<400> SEQUENCE: 117

```
atccagatcc ctacgaactg gattcacaca gtcactgctg taagctctgg tttttttttag     60 cttaggaagc aggttatgat caaacatgat taaaccatcg cgtgttcgcc agccatcaga     120
aatggaaagg caaatgttgt tatagtgatg gacagatcat gctgagatga ttgattatga     180
atcttactga tgactgtcat ttatgttatc gcactctgtg tgtgtgggtg tgtgtaatga     240
gtaatatcaa attaaccaga cgataggtgt tgaagattag ctgttgggcc accgtggcga     300
aaggtgtctt atacaagcca tcggcagtga cgcagaactg tagagaaccg ctgtaacaag     360
tcttcgaatg cattctttta atgtacagca cgacatgaag ggggttcgag tgtagcgaac     420
agttcgtgcg agaaagatca ttttcaatag cataaaagag tctgctttct gctgcaaaca     480
tggaaagaac ttacatttca atcattgagg agaagattat aacaaatcct aaatggttga     540
gattttagtt agtccattcg aactaaagtg gcgaagatgt cagttttttca agtggatgat     600 atttctcatg tatgttccgc agaggcaatc accttgtttg taactagaca tctagagaac     660
ctaacaagga ttgatggggg tgaggtgaaa tgtctgtttc ctctttaata tggatccagc     720
gatgccttac agagcggatg gatggcactg gcaagtctta atccttagct cgaatgtttg     780
attggtaaca gatgcctttt cttctttttc aatcacagct gacaaatgca aatatctaaa     840
accattggtt gtttggtgct tgcaagtctg gattacccca ctttatgttt cacctttcaa     900
taatgaataa caaggtactc gggaaaaaaa ggaaagggaa attcgcacaa ccaaagttgc     960
tatgcagaag tcaactcaat cctaatcaag ctgatgagag tgttgggccc tattttctgc    1020
agcaaacatg aatctcgatt catctcccctc gcaaagata aggaagctgc aaaagctttc    1080
ctcctaagtt tgttggcaag caaattgatt ttgtaccaga aataaataca aagtgaaacc    1140
caagcaatca cgcatggcct gatttgtgcc atgtccattt gatctccctc tactattttt    1200
cctgctttct caagcaaact agttgctgta acagtgaatg atcccccggc tctccccctc    1260
tctctctctc tctctctcca tttattccat ccatgttttt gctttcgca caacacttat     1320 cattgaggtg ctaactactg aattcccccta actaaaaatt ggaacctctc gcctaatttc    1380
```

-continued

| | |
|---|---|
| attttctccc actttgatga gcaccactct ctttcccaga tttcaaataa attgccactc | 1440 |
| tctccctcct ctttcctcac acaaccaaaa gccttcttca agtaccactt cttcactgtc | 1500 |
| ctctcttcac aatccccctc ttaccaagag caaagcaaaa aacatgatga agagactgtc | 1560 |
| atttctgctc ctactggtcc tgctcttcca atgctctacc accttggctc agcctgcggc | 1620 |
| cgccccagct ccgcctgtga tagccccggc tgcacctgct acgcctgcct taggcccggc | 1680 |
| tcctcctgtc ttaggcccag ctcctgcagg cccaaccgac atcacgaagg tcctcaagaa | 1740 |
| ggtgagccaa tttacggtgc tgctca | 1766 |

<210> SEQ ID NO 118
<211> LENGTH: 1928
<212> TYPE: DNA
<213> ORGANISM: Eucalyptus grandis

<400> SEQUENCE: 118

| | |
|---|---|
| ctggttccac gtcaagcacc tcctggagtg acaaggaaat gccaccggaa aatcaagatt | 60 |
| gctgttttag gctcactttt ttcctgagct aagtgggtcg catttcaaga aacagtagaa | 120 |
| gttacgttct ccatggaaac tcgaaaggat aaaaattaag aaacggaagc tccatgagaa | 180 |
| cgatggggggt cagcatcact cctattgtat tgtgctctca ttatctctgg cctacttgag | 240 |
| aagtgatctg ggattcgcta ttagtgaaaa caatcgcagg ctaactaaga tcttttatgc | 300 |
| taatcatatg gagaaatatc cctcttaagg gaagcatatg agttttttct taggatgact | 360 |
| acgcttattc aaaacctatc atacacgtca tgccaataat acccacttgt tgttccttta | 420 |
| ctcaggatcc tcgatagcca atactaattg gcaagaacct tgagtaacaa gctgaggtat | 480 |
| acataggcct atcattcatt tactagactc gattgcaagc acacatgatg cacatttata | 540 |
| tcagcaatca gcaatcatat ttccgaaaat tgtctctcag agaaaaagag agagagagag | 600 |
| agtccatagt atgtcatagc caaagaaaaa attagcaaca agatctcgag gtattgttga | 660 |
| aaggtagggc aatatcaaga attccattgt aattaatgtg tctagacaac atctaagaaa | 720 |
| aaaaagtgaa agaaaagagc tatatagtta ataatattta tacatgttgg agataaactt | 780 |
| gagttagagg tttatgacct cctagattga ttaaacagac caaatagtag taatcagggc | 840 |
| acttcttaaa tctactaata tattgttcaa acatgacttt taacctatct tgattagaaa | 900 |
| tgagtgttca agaaaacta atcatgcata tattttgtcg cccaatcacc ctagggtgga | 960 |
| aaaaaggcta tctactcaac aaatgctaaa attttacggc tacacgtggc cacagttgca | 1020 |
| gtacaattca tctcaaggaa ggactaaaac tgcaaagaga agaagactac ataggaaaaa | 1080 |
| ggaaaacaaa gaagccttga agtaaagagg agcataactc actcaactga gtgtgttcgc | 1140 |
| caatgtggca agaaaaagc ctctaagatc ctcacaaatg gccacgtgga ctcacacggc | 1200 |
| accctataca agtactacta ctactacagg actatgccag aaggagaagt gttagcgtga | 1260 |
| gtaccacgtg cgcacgcaga atctaagcct agcaaaaact atgctgagtc aagcagctcc | 1320 |
| cccacccatg aagatagtac tgtaatgtga ctcttgacag cgaaaccaaa cagtactcca | 1380 |
| agagaaaagc caaagcagca aaatgggggc ccgcagcaag aacctctgac tcgacctgga | 1440 |
| cccaccaaga acaacagcca gccacaaaat aacgtaaaga cttttgcgg ccactaactc | 1500 |
| ctcgacaagt ggcactgctt ggattcccctt catcttgcct tcacttaacc cccacccctcc | 1560 |
| ctcacactgc attcacttca aacactcccc agtttcagag tttcattgag aaatatgttg | 1620 |
| aaggaagaca cgagtggcag cggcggcagc agcggcagcg gcagcggtgg taatagctgg | 1680 |
| gcacgtgtgt gtgacacttg ccgctcggca gcatgcaccg tgtactgccg tgccgacttg | 1740 |

```
gcttacctat gctccagctg tgacgctcgt attcacgcag ccaccgtgtg gcctcgcgcc    1800
atgagcgcgt gtgggtgtgc gaagcgtgcg agcgcgcccc ggctgccttc ctctgcaagg    1860
ctgatgcagc atcactgtgc accgcctgcg atgcagacat acactcagcc aacccgcttg    1920
cgcgccgc                                                              1928

<210> SEQ ID NO 119
<211> LENGTH: 602
<212> TYPE: DNA
<213> ORGANISM: Eucalyptus grandis

<400> SEQUENCE: 119
attgggagga agtagagtgt gctgtgtgag attggtcgat gagctggctc ttgtggagat      60
ggcaagtgat tgtggcttct gtgatgcata tatataggca agggacgtga tgcggaggaa     120
gtatgtatca tcagcttata ataatgattg gtcagtttgt aagtgaatat taagggcctc     180
atgggtgttg gttcacggcc caaggcgggg cccactcacc gggggattta tcgtgtaagg     240
atacatccag ggtcagggtg tttggggaca cactttgcca tcttatgtgg gcatgatcag     300
attgagaaga atccgatcct tcttttcct aaaccattga acccaccatg agaatctttg      360
tttggaggga aaaataaaaa aatagattga gacgtattct aggagaggat agcaaaagaa     420
tgtgactttg tttgtttgtg tatcggattg atctaaggaa aaaagacact aaccgttcta     480
caattttcat acaactcttt catttaagca ccgtgacttc caaaaatcga tcatccttat     540
acggttggaa atcacacgtg gcattgctgt aaaagaaata gttgatgggt ctcattgaag     600
at                                                                    602

<210> SEQ ID NO 120
<211> LENGTH: 1326
<212> TYPE: DNA
<213> ORGANISM: Pinus radiata

<400> SEQUENCE: 120
aaaaaaggga aacattatac caaattttat gatatctttc aacaacatac tcttctatat      60
atggtgcctc ctctgatgga cccttgtcaa cttctctctt tatgtgtaa tgcctcaaga     120 gcccccactc acaagataat atcttttcca taatataata tatattccta ttgaagcagt     180
cttttgatgt accgagtaca ctactcatgg tgaaggccgt gtcttgcagc ttttcccatg     240
gtttattttg aaagtaatag tactggacct catttgcaac gacacataat attcttactg     300
acgacacttt gtttgatttc ttatagaaaa atgcaaggtg gcacaaaaag atggaaagcc     360
cgacctatca agcatacgaa gggtcatgtt cacaccctct gaaatcttca gagtctcacc     420
ctatgttgga cgctaatcaa tgggatcacg ctgaaacata tcgtaaatga cgaatcaatc     480
aatcaatcat tgaaaaatat accagataac tcctacgatg gaggggatta tttgcgtacc     540
ctccgcgtgg gtgggcacat tggcaggtc ctttggtaag tcttggagac agagtcacgt      600
ttccataatt gaagtggaca tttatgaatc tttcgaaagt tgtagaactc ttaattttcg     660
acggaatagt ttgacacgtt ttgtacgatc tggtttttcc ggggaacgcc aattttggtt     720
tctgaaggac agcatttaca atattgtctg tcgttgacca ggacagctgg ctcggaactc     780
gggtttccga tgcgcaggaa gcgcattgaa atgagaaaat aatctagttc tacctgtgga     840
gctatcacaa aatactaaaa ctggtggaca tacctcttgt ctgttctcga aatcggccaa     900
aatgggaaag aagagggtag agctgaaacg cattcaaaac cctagcagtc gacatgctac     960
tttctctaaa cgcaagaatg gattgctaaa aaaggcgttc gagctttctg tcctctgtga    1020
```

```
tgctgaagtc gctctcatca tttctctga aactggcaag atttacgaat ttgcgagcaa    1080
taacgatatg gcagcaattc tgggaaaata ccgagtacac gaagaaggca ctgaaacgtc    1140
cagtccaaca tcgcttcaaa acgtaaagta tcatgaatca gggcttgaga aattgcaaga    1200
gaagttgacc gctttgcaaa agaaggaaaa gaacttgatt ggtgaagact tggaggtatt    1260
aacaatgaaa gaactgcaac ggcttgaaaa acagttacaa attggcataa aaaggttagt    1320
gataga                                                                1326
```

<210> SEQ ID NO 121

<400> SEQUENCE: 121

000

<210> SEQ ID NO 122

<400> SEQUENCE: 122

000

<210> SEQ ID NO 123

<400> SEQUENCE: 123

000

<210> SEQ ID NO 124

<400> SEQUENCE: 124

000

<210> SEQ ID NO 125
<211> LENGTH: 1489
<212> TYPE: DNA
<213> ORGANISM: Eucalyptus grandis

<400> SEQUENCE: 125

```
atcattgcac agatgctggc ctatcaagcg tccatcgatt aatgtcatga tgattcgtgt      60
catcaatttt cccatagcga gtcagcgacc accgcatgca cgatgccgat gtcgccgtgc     120
gaaaaacatc gagcagacgg catgctaaag acatgcattt cggtcctctc tgatggtgaa     180
ttgcaatgca gaagagactc ggatggattt gatttcaaag tgacgacact gacttctgcg     240
cattcgttta tacatgcata ttcttcaaaa ggatgcttct gccacttctc ttttcagtg     300 gctttcagtt caagaaaccc cattaatttc aaaagagaaa gcaggtggct atctgcacgg     360
aagaatggtc tcattgttct atttaagcat ttcctttttt cattgcacgt gtggtctaga     420 agagttttc cttcctcat atgaagccaa ataccatgt ccgagtttca cataatacaa      480
aacatttccc aggaagaaaa tgttcccaga gaccacatga gttctcttga atctcttgaa     540
atttataacc ctgacccatg aaatcgggca agaaaaactg taatggcatc agcaggatgt     600
gaagagaatg gaggcggcgt acacctaatg cggttttacc gagtcggata tggttgtcgt     660
atggacaaca ggctgttgat ttggtaagtg tcggattttt tagggagaca aaagtccaac     720
ctatccccaa gcaaatccgg ggaattcgat ggtctcttga atatgtaaat gcttttgaac     780
ttcagtgact gagtccaaat gatcttcttc ttctgcaagc taactaacct tcggtccttc     840
tcttggctgc ttttttgcaac tactactata ttattgcttt tagtaatggt ggtagttgca     900
atagaagtaa gcatagtgaa aaagtgttga tcggcaacaa acaaagaagc ttaattatta     960
```

```
ccgatccagc acaccttaat catctccaac tgttctctat tcttgcatct tcaaccgtaa    1020
tcagcagata atcctcgtca ttaatcatta ttctgaaaca acctgttgcc ccaccaaaga    1080
aaactcatag gtgactctgc tttgttctct tgcaatgcca tatatacacc tgaaattctg    1140
atcgctctca ctcatctgtc gcattcaaag cctcaaagcc gcttgtttct gaactttgc    1200 cttggcttca agaagaaag  tcctcaaata gaagatcgac catatgggac tgaagatatt    1260
ctcagtcggc tttgctcttc tttgttgctt ctgttcactt ggcttctgtg atcaagacgg    1320
ttttctgagt ttagcttgtg gtggaactac caattacacg gattcatcca acatctggtg    1380
gattaccgac agtgatttca taagcacagg aaagactacc tatgttgaca atatcgaggg    1440
caattcatct ggtgtttcgc ttcggttctt cccagattcc aaagtccat              1489

<210> SEQ ID NO 126
<211> LENGTH: 1273
<212> TYPE: DNA
<213> ORGANISM: Eucalyptus grandis

<400> SEQUENCE: 126
ttgtaaatta tgtgtgctta atagggtctt gttaatcaat gatcagtgta ttttttacgc      60
atgtgatgaa aaagtaattg cttttgagaa tatagttaca tcgaaaggac aatcaattcg     120
tttgacattg taattttta tttgatagtt taacaagtgc ctcggaacac tcttcaacat      180
atcctttcac tttattttgc atatttatgc ttgtacaaca acattttcaa ttgggtgatc     240
ataattcgta atatttataa ttttttgtta acaatgagta actctatact cctggattga     300
gcaaacatat ttgtaaagta gttatgagag tattacttat acttagacgt tgtgagatac     360
tcatgatcgt atcatatgtc cactagagga tatagattta cctagatgaa gccccttct     420 tagaagtagg aaaaaaaaaa ctattatatt gacttgaacc catatcataa aaagtacgag     480
actcaaaatc caatcttaca tgtatatgtg tatatatata tgttcgcaaa tgataacaat     540
cttttcaaga atcaagacac cagaaaacca tatttcaat  atccgtcaat gtcaatgtcc     600
tactcacatc gaacaggact gccgcgtaca caacaagttc cccagctaca gatttaccta     660
caattaggaa atgcaacccg aaaagacagg tctccatttc ttccttcact ttcccactca     720
tgaaaatgaa atatataatc acaaaatgcc tgagcgacac taaaggaacc aaagaacaac     780
gattccaact cagagagaga gagagagaga gagagaggga ctaattttg  gctgctcaac     840 aaaggaagca actttattca aatccatttt gctttagcgt gcccgtaatt ccaaccaaac     900
atatcctcaa agcccctaata tatactccca caagcgcacc tcgtttccta cacacaagta     960
caaagcgtca acttcttctt cgctaaactg gtctcacaga cactcgcttg tccctcagtc    1020
cacactttgg cttagctcac agcaactatg gctgagacag cggaacccca gaagctggtc    1080
gagctcgaga aggtgcccga ccccgaggcc ggcgtgcccc gaaaggaga  ggaggcgccc    1140 ccagaacccc cacttccgcc cccagtgccg gcgccgccgg tggaaacttg cgtcttggtt    1200
gacgtggcac ttagggtttt gctcttcgca gcgacactga ccgctgtggt ggtgatggtc    1260
acggcgaacc aaa                                                       1273

<210> SEQ ID NO 127
<211> LENGTH: 3720
<212> TYPE: DNA
<213> ORGANISM: Eucalyptus grandis

<400> SEQUENCE: 127
cgaagttcag ctcccgcttc cctgatgttt tcaaatcttc tttcaagtta gaagtacata      60
```

```
tacagcaaac aagatccaac ccttttctta tcatgagccc ttacttccac aagtgacatt    120
tggcactagt cccacaattt aatcattcta tttccattct ctgtaaatgt accctattca    180
aagttgggac ataatgaccc ttttgaagcg ttaggatcac actttattaa aagggaacaa    240
caacattgac agcaaatgca cgcactttcg ataaagttca gacagtataa taagttctca    300
ttccaaaagg ccccaatgtg gaaggtacga cttctctaac cctgttttga tttgatttt     360 tcgcagagga aaaatcatca ccaaagactt ataaaaattg aagtagcaaa gaaagaaaa     420 gcaagattag caaacagaga ggagaaagag aggggaagga gtgatgggcc aacagccatt    480
ctcccagaaa ccacataaaa aacaaacaca gaatgatcac ttgtgaagaa cacgcggagt    540
tccaagcaaa gcatctcgag aatcaatgtc gctctttctt cacaagcatt ggacagaaaa    600
aaagagcaag ctctaagttt ccagcgaaaa gcccgaaaat taggacgaag ggcgacgaga    660
aaacgaaaaa ctagaaggaa acaaaaatca aaataaaaag gaaagagagg cctgtgcgag    720
taataacgat tgtaaggcaa gacgatgaac cggcaaagct tgattcctgg ttgcaaattg    780
gggacgaaga tggctcaaaa taggagtgac gggcggtgat tttaccgcga agcgaaacct    840
agaatgcaag gagcaaagaa gagggtggtg gcagaatcga cgccgacagt ggcagcagag    900
tcgacgccag cagcagcggc ggagtgtatg agcggagaag gcgtagtagc tgatggtggt    960
ggagtcgaca agaggagaag gcaagaagga agagtcgtcc ggaaccaatg tgtttggctt    1020
tgggtgtgga tgttttgtat tttggtgaga tgagagaacg tgtttgtttc attgtttaag    1080
attaataatg tgttcacgag ccgaacaatg tttcgacctt aacccgactc aaaacatggt    1140
tgtttgcttg ttttgtaatt gttacctaaa taatattaag acctaaaaca tcgtgttcgg    1200
gttgagtttt tggacactcc tacctgtgat agccaccgcg agcgtagact actggatttg    1260
atatttggaa gcacgaccac ctttattgc caattggaaa gataaaaacg aggcacgaat    1320
gggaccaaaa tgagcaagaa atacggtatc tttggatgcc atgtttgcca tttgtcacct    1380
tacgcagagt gctagtgtaa attctcaatc aaagagcacg ggatacgttt tgttcagaac    1440
ttcacaccat gagcaggctt ggaaaaggag gaccgtaaag gaaatcacca tattgtagat    1500
gttcaaaata agttaacgaa tcagaaaaag aatacccatt tagccgaatt taattaacgt    1560
aatctttacg tgggacaact aaagtggaaa ttttttttaac ttgtgctgat gttttagctt   1620
taaaatgcaa tcaccagcct aaaatatatc ttgattcatt atttgaaatc tcgaatgtaa    1680
attttagtag tatatcataa atatctccgt ttggcctact ttctaatgca gcatccgttt    1740
gatagggtgt cgacgactca actctacgta cgtaaaaaaa aaaaattaaa aaatgccata    1800
ttgactttat agtgtagcac gtcatcaaat tgggcgagca gtcgtcggat ggaattaaaa    1860
ttacatcaaa tggaaattgt tgttggttg cactttgggt caattttttt tggactttga     1920
tgtaagtaat taagttaagt aatgatttcc attcactagg aagtcgaagc ccacacaacc    1980
ttgaaaaaaa aaaaaaaaaa agacatcagt ccatgcaaac aacgaattaa ctgaatttaa    2040
tgaagaatac gagaaacgta aaaacttgat aagtttatta aacgatagga atgacattta    2100
gattaatgta agtacaagta tctatagaga gttatacaaa tatatatata tatatatata    2160
tatatataat atttcagata gttttatgaa aatacttaaa attaaataga agaaaaaata    2220
tcaaactgat attgctctaa atgggattct acttttacta tcatagagat aataagctaa    2280
ggtataatta agtagaacta tcgtaatata tataatatca ataagataaa aaagtaaata    2340
gaaagatagc cactttttt gttattgagg aaatggattg aaatgaaata atattacgaa     2400
atcaacaata gtgatagaag gaatgatttg acctagttat ggaatatcga gtgactaaat    2460
```

-continued

```
caggcaaatc gaaagtttaa gaatttaggt tgcacattta gctatgttta aagaccatat    2520
tgtatctgtc atgatagttt agagacttgc gactctctct cttgcgcatt caaacaaaag    2580
aagaacaaaa aatttaagaa tgacgttgtg cactcggtca gagttaaaga actattagtg    2640
tgattttttc attttaagt aaacaaaaca cgatgtggga gatgtgggag attggaaaag     2700
tgatggctaa aatttggaag aaaaatagaa atatgatcat gattgaagat ttataaaata    2760
aataatcatg gtacggactg aaactttaaa aaaatagtaa atgtactatg gtagacaaaa    2820
acaaattgag agtgtatatg gtaagggcaa cgctctttcc attccttata taactaaatt    2880
cacctaactc ttccaaaaat acaaagttgc atctatttta cattagtagt cccaaattta    2940 tttactttt ttttttttag tttttatatc tacataagat ttacttacca tagttaagaa     3000
tttatatgtt taattttagt taattttata ttttctatgt atattagagg cactatcttt    3060
cttttatccg ataatgcaat tttctttgat acgctaacaa acaaaacatg tgaaaagctt    3120
aattatggca attatcataa atagaaaaaa attagaaaaa aagagaggaa atgggccatt    3180
atttaaattg caatcgaaag attgagggca attctgtttc tctagtgtaa ataagggtgt    3240
atttaataat tgagggatgg aaatagcatg gtcactcggt aattatcaag gaaagcaaga    3300
ataaaaatgg aaaaaaaaaa aaaaaagct tgaagaggcc aatgtcgaaa ttatgagcgc     3360
gagatgagga cactcctggg aaacgaaaaa tggcattcgc gggggtgct atataaagcc     3420 tcgtgtaagg gtgcgttcct cactctcaaa ccctaatcct gcccttccct tctgctgctg    3480
ctgctcgtca cctctctcct ccctctcgcg gccagctgcg agatctgccg agtttaagcc    3540
tcgtacatca aaatgggtaa ggagaagatt cacatcagca ttgtggtcat tggccatgtc    3600
gattctggga agtcaaccac aactggccac ttgatataca agctcggagg aatcgacaag    3660
cgtgtgattg agagattcga gaaggaagct gctgagatga caagagatc gttcaagtat     3720
```

<210> SEQ ID NO 128
<211> LENGTH: 25
<212> TYPE: DNA
<213> ORGANISM: Eucalyptus grandis

<400> SEQUENCE: 128

```
tgagcggata acaatttcac acagg                                            25
```

<210> SEQ ID NO 129
<211> LENGTH: 25
<212> TYPE: DNA
<213> ORGANISM: Eucalyptus grandis

<400> SEQUENCE: 129

```
tcgagttttt tgatttcacg ggttg                                            25
```

<210> SEQ ID NO 130
<211> LENGTH: 1962
<212> TYPE: DNA
<213> ORGANISM: Eucalyptus grandis

<400> SEQUENCE: 130

```
atgcgccatg ttgacaaaaa ggctgattag tatgatcttg gagttgttgg tgcaaatttg    60
caagctgacg atggcccctc agggaaatta aggcgccaac ccagattgca aagagcacaa    120
agagcacgac ccaacctttc cttaacaaga tcatcaccag atcggccagt aagggtaata    180
ttaatttaac aaatagctct tgtaccggga actccgtatt tctctcactt ccataaaccc    240
ctgattaatt tggtgggaaa gcgacagcca acccacaaaa ggtcagatgt catcccacga    300
```

| | |
|---|---|
| gagagagaga gagagagaga gagagagagt tttctctcta tattctggtt caccggttgg | 360 |
| agtcaatggc atgcgtgacg aatgtacata ttggtgtagg gtccaatatt ttgcgggagg | 420 |
| gttggtgaac cgcaaagttc ctatatatcg aacctccacc accatacctc acttcaatcc | 480 |
| ccaccattta tccgttttat ttcctctgct ttcctttgct cgagtctcgc ggaagagaga | 540 |
| gaagagagga gaggagagaa tgggttcgac cggctccgag acccagatga ccccgaccca | 600 |
| agtctcggac gacgaggcga acctcttcgc catgcagctg gcgagcgcct ccgtgctccc | 660 |
| catggtccta aaggccgcca tcgagatcga cctcctcgag atcatggcca aggacgggcc | 720 |
| gggcgcgttc ctctccacgg gggaaatcgc ggcacagctc ccgacccaga accccgaggc | 780 |
| acccgtcatg ctcgaccgga tcttccggct gctggccagc tactccgtgc tcacgtgcac | 840 |
| cctccgcgac ctccccgatg gcaaggtcga gcggctctac ggcttagcgc cggtgtgcaa | 900 |
| gttcttggtc aagaacgagg acggggtctc catcgccgca ctcaacttga tgaaccagga | 960 |
| caaaatcctc atggaaagct ggtattacct gaaagatgcg gtccttgaag cggaatccc | 1020 |
| attcaacaag gcgtacggga tgaccgcgtt cgagtatcat ggcaccgacc cgcgattcaa | 1080 |
| caagatcttt aaccggggaa tgtctgatca ctccaccatt actatgaaga agatactgga | 1140 |
| aacatacaag ggcttcgagg gcctcgagac cgtggtcgat gtcggaggcg gcactggggc | 1200 |
| cgtgctcagc atgatcgttg ccaaataccc atcaatgaaa gggatcaact tcgacctgcc | 1260 |
| ccaacggatt gaagacgccc caccccttcc tggtgtcaag cacgtcggag cgacatgtt | 1320 |
| cgtcagcgtt ccaaagggag atgccatttt catgaagtgg atatgccatg actggagtga | 1380 |
| cgaccattgc gcgaagttcc tcaagaactg ctacgatgcg cttcccaaca atggaaaggt | 1440 |
| gatcgttgca gagtgcgtac tccctgtgta cccagcacg agcctagcga ccaagaatgt | 1500 |
| gatccacatc gactgcatca tgttggccca caacccaggc gggaaagaga ggacacagaa | 1560 |
| ggagttcgag gcattggcca aaggggccgg atttcagggc ttccaagtca tgtgctgcgc | 1620 |
| tttcggcact cacgtcatgg agttcctgaa gaccgcttga tctgctcctc tgtggtgatg | 1680 |
| ttcatggttc ttggatttga aggtcgtga aggagcccctt ttctcacagt ggcttcggc | 1740 |
| ataccaagtt cttctcataa aaggaaacaa taagaagcga ctgtatgatg gcgcaagtgg | 1800 |
| aagttacaag atttgttgtt ttatgtctat aaagttttga gtcttctgca tactgatttc | 1860 |
| acagaatgtg taacgaaacg gcgtatatgg atgtgcctga atgatggaaa ttgtgatatt | 1920 |
| ctgtcttctt tttcagtaaa tcacttcgaa caaaaaaaa aa | 1962 |

<210> SEQ ID NO 131
<211> LENGTH: 534
<212> TYPE: DNA
<213> ORGANISM: Eucalyptus grandis

<400> SEQUENCE: 131

| | |
|---|---|
| atgcgccatg ttgacaaaaa ggctgattag tatgatcttg gagttgttgg tgcaaatttg | 60 |
| caagctgacg atggcccctc agggaaatta aggcgccaac ccagattgca aagagcacaa | 120 |
| agagcacgac ccaacctttc cttaacaaga tcatcaccag atcggccagt aagggtaata | 180 |
| ttaatttaac aaatagctct tgtaccggga actccgtatt tctctcactt ccataaaccc | 240 |
| ctgattaatt tggtgggaaa gcgacagcca acccacaaaa ggtcagatgt catcccacga | 300 |
| gagagagaga gagagagaga gagagagagt tttctctcta tattctggtt caccggttgg | 360 |
| agtcaatggc atgcgtgacg aatgtacata ttggtgtagg gtccaatatt ttgcgggagg | 420 |
| gttggtgaac cgcaaagttc ctatatatcg aacctccacc accatacctc acttcaatcc | 480 |

```
ccaccattta tccgttttat ttcctctgct ttcctttgct cgagtctcgc ggaa        534
```

<210> SEQ ID NO 132
<211> LENGTH: 485
<212> TYPE: DNA
<213> ORGANISM: Eucalyptus grandis

<400> SEQUENCE: 132

```
gtgcaaattt gcaagctgac gatggcccct cagggaaatt aaggcgccaa cccagattgc   60
aaagagcaca aagagcacga cccaaccttt ccttaacaag atcatcacca gatcggccag  120
taagggtaat attaatttaa caaatagctc ttgtaccggg aactccgtat ttctctcact  180
tccataaacc cctgattaat ttggtgggaa agcgacagcc aacccacaaa aggtcagatg  240
tcatcccacg agagagagag agagagagag agagagagag tttctctct atattctggt   300
tcaccggttg gagtcaatgg catgcgtgac gaatgtacat attggtgtag ggtccaatat  360
tttgcgggag ggttggtgaa ccgcaaagtt cctatatatc gaacctccac caccatacct  420
cacttcaatc cccaccattt atccgtttta tttcctctgc tttcctttgc tcgagtctcg  480
cggaa                                                              485
```

<210> SEQ ID NO 133
<211> LENGTH: 306
<212> TYPE: DNA
<213> ORGANISM: Eucalyptus grandis

<400> SEQUENCE: 133

```
ttccataaac ccctgattaa tttggtggga aagcgacagc caacccacaa aaggtcagat   60
gtcatcccac gagagagaga gagagagaga gagagagaga gttttctctc tatattctgg  120
ttcaccggtt ggagtcaatg gcatgcgtga cgaatgtaca tattggtgta gggtccaata  180
ttttgcggga gggttggtga accgcaaagt tcctatatat cgaacctcca ccaccatacc  240
tcacttcaat ccccaccatt tatccgtttt atttcctctg ctttcctttg ctcgagtctc  300
gcggaa                                                             306
```

<210> SEQ ID NO 134
<211> LENGTH: 293
<212> TYPE: DNA
<213> ORGANISM: Eucalyptus grandis

<400> SEQUENCE: 134

```
tgattaattt ggtgggaaag cgacagccaa cccacaaaag gtcagatgtc atcccacgag   60
agagagagag agagagagag agagagagtt ttctctctat attctggttc accggttgga  120
gtcaatggca tgcgtgacga atgtacatat tggtgtaggg tccaatattt tgcgggaggg  180
ttggtgaacc gcaaagttcc tatatatcga acctccacca ccatacctca cttcaatccc  240
caccatttat ccgttttatt tcctctgctt tcctttgctc gagtctcgcg gaa         293
```

<210> SEQ ID NO 135
<211> LENGTH: 119
<212> TYPE: DNA
<213> ORGANISM: Eucalyptus grandis

<400> SEQUENCE: 135

```
ggagggttgg tgaaccgcaa agttcctata tatcgaacct ccaccaccat acctcacttc   60
aatccccacc atttatccgt tttatttcct ctgctttcct tgctcgagt ctcgcggaa   119
```

<210> SEQ ID NO 136

-continued

```
<211> LENGTH: 99
<212> TYPE: DNA
<213> ORGANISM: Eucalyptus grandis

<400> SEQUENCE: 136
agttcctata tatcgaacct ccaccaccat acctcacttc aatccccacc atttatccgt    60
tttatttcct ctgctttcct ttgctcgagt ctcgcggaa                           99

<210> SEQ ID NO 137
<211> LENGTH: 66
<212> TYPE: DNA
<213> ORGANISM: Eucalyptus grandis

<400> SEQUENCE: 137
tcacttcaat ccccaccatt tatccgtttt atttcctctg ctttcctttg ctcgagtctc    60
gcggaa                                                               66
```

COMPOSITIONS AND METHODS FOR THE MODIFICATION OF GENE EXPRESSION

CROSS-REFERENCE TO RELATED APPLICATIONS

This application claims priority to: U.S. patent application Ser. No. 10/291,447, filed Nov. 8, 2002, which is incorporated by reference herein in its entirety, which claims priority to U.S. Provisional Patent Application 60/345,397, filed Nov. 9, 2001; priority to U.S. Provisional Patent Application No. 60/425, 087, filed Nov. 8, 2002, which is incorporated herein by reference; priority to U.S. patent application Ser. No. 10/137,036, filed Apr. 30, 2002, which claims priority to U.S. patent application Ser. No. 09/276,599, filed Mar. 25, 1999 (now U.S. Pat. No. 6,380,459) and priority to U.S. patent application Ser. No. 09/724,624, filed Nov. 28, 2000 (now abandoned), which is a CIP of U.S. patent application Ser. No. 09/598,401, filed Jun. 20, 2000 (now U.S. Pat. No. 6,596, 925), which claims priority to International Patent Application No. PCT/NZ00/00018, filed Feb. 24, 2000 and to U.S. Provisional Patent Application No. 60/146,591, filed Jul. 30, 1999, and is a CIP of U.S. patent application Ser. No. 09/276, 599, filed Mar. 25, 1999 (now U.S. Pat. No. 6,380,459).

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: ARBG 004 07US 2nd Sub SeqList.txt, date recorded: Dec. 4, 2008, file size 157 kilobytes).

TECHNICAL FIELD OF THE INVENTION

This invention relates to the regulation of polynucleotide transcription and/or expression. More specifically, this invention relates to polynucleotide regulatory sequences isolated from *Eucalyptus grandis* that are capable of initiating and driving the transcription of polynucleotides in plant vascular tissues, and the use of such regulatory sequences in the modification of transcription of endogenous and/or heterologous polynucleotides involved in wood formation.

BACKGROUND OF THE INVENTION

Gene expression is regulated, in part, by the cellular processes involved in transcription. During transcription, a single-stranded RNA complementary to the DNA sequence to be transcribed is formed by the action of RNA polymerases. Transcription is initiated by the binding of RNA polymerase to characteristic recognition sequences in the promoter region of the gene. As used herein, the term "promoter" refers to the 5' non-coding region of a eukaryotic gene that is involved in transcription initiation and regulation, which generally comprises between 100 and 1000 (or more) nucleotides upstream of the transcription start site. Generally, the promoter includes the transcription start site, and farther upstream from the transcription start site, the initiator region, comprising characteristic sequence motifs involved in binding RNA polymerase and initiating transcription, and cis-acting transcription control elements (also referred to as "promoter-proximal elements") which extend several hundred bases upstream of the transcriptional start site and interact with trans-acting protein factors to regulate transcription. Such cis-acting control elements may be cell-or-tissue specific and may determine the responsiveness of transcription of the particular gene associated with the promoter to hormones and other endogenous signals. Other cis-acting control elements may affect the strength of the promoter (e.g., enhancers) or efficiency of transcription (e.g., the 5' untranslated sequence downstream of the start site). Enhancers can occur upstream or downstream from the initiation site.

Tissue-specific promoters are particularly advantageous for use in transgenic modification of plants where spatial localization and/or developmental timing of gene expression is important, or where constitutive expression would be detrimental to the development and physiological function of the transgenically modified plant.

There is a continuing need for promoters that can be activated specifically in tissues involved in xylogenesis and primary and secondary xylem. Such promoters can be used to selectively modulate the expression of genes involved in secondary cell wall formation in plants, for example, by eliminating or reducing lignification (and increasing cellulose deposition) in secondary xylem, increasing the volume of particular secondary cell wall layers, and controlling the sites and levels of lignification and cellulose deposition.

SUMMARY OF THE INVENTION

Briefly, isolated polynucleotide regulatory sequences from eucalyptus that are involved in the regulation of caffeic acid O-methyltransferase (cOMT) gene expression are disclosed, together with methods for the use of such polynucleotide regulatory regions in the modification of expression of endogenous and/or heterologous polynucleotides in transgenic plants. The invention encompasses recombinant promoters comprised of one or more motifs in the inventive promoter sequences and having new or improved activities.

In a first aspect, the present invention provides an isolated polynucleotide sequence comprising a vascular tissue-specific promoter of the *E. grandis* cOMT gene, and functional promoter fragments thereof. In a preferred embodiment, the polynucleotide sequence is selected from the group consisting of:

(a) the sequences recited in SEQ ID NO: 12 and SEQ ID 113, nucleotides 1019-1643, and their complements;
(b) reverse complements of the sequences recited in (a);
(c) reverse sequences of the sequences recited in (a);
(d) sequences having at least 75% identity to a sequence recited in (a);
(e) sequences having at least 90% identity to a sequence recited in (a);
(f) a polynucleotide sequence that hybridizes to a polynucleotide sequence of (a) above under stringent conditions; and
(g) a polynucleotide comprising a 20-mer, a 40-mer, a 60-mer, an 80-mer, a 100-mer, a 120-mer, a 150-mer, a 180-mer, a 220-mer, a 250-mer, a 300-mer, 400-mer, 500-mer or 600-mer of a sequence recited in (a) or (e) above.

In another aspect, the present invention provides genetic constructs comprising a polynucleotide of the present invention, either alone, or in combination with one or more additional polynucleotides of the present invention, or in combination with one or more known polynucleotides, together with cells and target organisms comprising such constructs. The genetic construct may comprise for example, a sequence identified herein as SEQ ID NO. 60, which comprises a cOMT promoter functionally linked to a cOMT coding sequence. This construct may be used to regulate the biosynthesis of monolignols and lignin in plants.

In one embodiment, the genetic constructs comprise, in the 5'-3' direction, a polynucleotide promoter sequence of the present invention, a polynucleotide to be transcribed, and a gene termination sequence. The polynucleotide to be transcribed may comprise an open reading frame of a polynucleotide that encodes a polypeptide of interest and/or a non-coding, or untranslated, region of a polynucleotide of interest. The open reading frame may be orientated in either a sense or antisense direction. Preferably, the gene termination sequence is functional in a host plant. Most preferably, the gene termination sequence is that of the gene of interest, but others generally used in the art, such as the *Agrobacterium tumefaciens* nopaline synthase terminator may be usefully employed in the present invention. The genetic construct may further include a marker for the identification of transformed cells.

In one embodiment, the genetic construct is used for transcriptional silencing of a gene of interest. For example, the construct may comprise an inverted repeat of a cOMT promoter sequence or promoter fragment of the present invention driven by an unrelated promoter, such as an inducible or constitutive promoter.

In another embodiment, the genetic construct is designed to downregulate the expression of a gene of interest, for example, by posttranscriptional silencing, by antisense suppression, or by cosuppression.

In a further aspect, transgenic plant cells comprising the genetic constructs of the present invention are provided, together with organisms, such as plants, comprising such transgenic cells, and fruits, seeds and other products, derivatives, or progeny of such plants. Propagules of the inventive transgenic plants are included in the present invention. As used herein, the word "propagule" means any part of a plant that may be used in reproduction or propagation, sexual or asexual, including cuttings.

Plant varieties, particularly registerable plant varieties according to Plant Breeders' Rights, may be excluded from the present invention. A plant need not be considered a "plant variety" simply because it contains stably within its genome a transgene, introduced into a cell of the plant or an ancestor thereof.

In yet another aspect, methods for modifying gene expression in a target organism, such as a plant, are provided, such methods including stably incorporating into the genome of the organism a genetic construct of the present invention. In a preferred embodiment, the target organism is a plant, more preferably a woody plant such as poplar, eucalyptus and pine species, sugarcane, forage grasses and *Salix* spp., most preferably from the group consisting of *Eucalyptus grandis* and *Pinus radiata*.

In another aspect, methods for producing a target organism, such as a plant, having modified polypeptide expression are provided, such methods comprising transforming a plant cell with a genetic construct of the present invention to provide a transgenic cell, and cultivating the transgenic cell under conditions conducive to regeneration and mature plant growth.

In other aspects, methods for identifying a gene responsible for a desired function or phenotype are provided, the methods comprising transforming a plant cell with a genetic construct comprising a polynucleotide promoter sequence of the present invention operably linked to a polynucleotide to be tested, cultivating the plant cell under conditions conducive to regeneration and mature plant growth to provide a transgenic plant; and comparing the phenotype of the transgenic plant with the phenotype of non-transformed, or wild-type, plants.

The above-mentioned and additional features of the present invention and the manner of obtaining them will become apparent, and the invention will be best understood by reference to the following more detailed description. All references disclosed herein are hereby incorporated by reference in their entirety as if each was incorporated individually.

BRIEF DESCRIPTION OF THE DRAWINGS

FIG. 1. Nucleotide sequence of the *Eucalyptus grandis* cOMT promoter (SEQ ID NO. 12) showing the motifs (underlined) located within the sequence and the putative TATA box (grey box).

FIG. 2. Nucleotide sequence of the Eucalyptus grandis cOMT gene and promoter (SEQ ID NO. 113, nucleotides 1019-1643). The promoter region is in bold.

FIG. 5. Vascular-specific expression of an *E. grandis* OMT Promoter-GUS construct in transformed *Nicotiana benthamiana*. The GUS sequence was expressed under the control of SEQ ID NO. 12. GUS staining is shown in xylem of the stem base (top left panel), midstem (top right panel) and roots (bottom panel).

FIG. 6. Nucleotide sequence of OMT gene and promoter (SEQ ID NO: 130). The start and stop codons and putative TATA box are boxed and the cis-elements are double-underlined. The promoter region is in bold.

FIG. 7. Nucleotide sequence of the 534 by OMT promoter (SEQ ID NO: 131) showing the motifs (boxed) located within the sequence and the putative TATA box (double-underlined).

FIG. 8. Nucleotide sequence of the 485 by fragment of the OMT promoter (SEQ ID NO: 132) showing the motifs (boxed) located within the sequence and the putative TATA box (double-underlined).

FIG. 9. Nucleotide sequence of the 306 by fragment of the OMT promoter (SEQ ID NO: 133) showing the motifs (boxed) located within the sequence and the putative TATA box (double-underlined).

FIG. 10. Nucleotide sequence of the 293 by fragment of the OMT promoter (SEQ ID NO: 134) showing the motifs (boxed) located within the sequence and the putative TATA box (double-underlined).

FIG. 11. Nucleotide sequence of the 119 by fragment of the OMT promoter (SEQ ID NO: 135) showing the motifs (boxed) located within the sequence and the putative TATA box (double-underlined).

FIG. 12. Nucleotide sequence of the 99 by fragment of the OMT promoter (SEQ ID NO: 136) showing the motifs (boxed) located within the sequence and the putative TATA box (double-underlined).

FIG. 13. Nucleotide sequence of the 66 by fragment of the OMT promoter (SEQ ID NO: 137).

FIG. 15. GUS expression driven by the OMT promoter and promoter fragments in stained tissue sections of transgenic tobacco plants.

DETAILED DESCRIPTION

Figure 3:
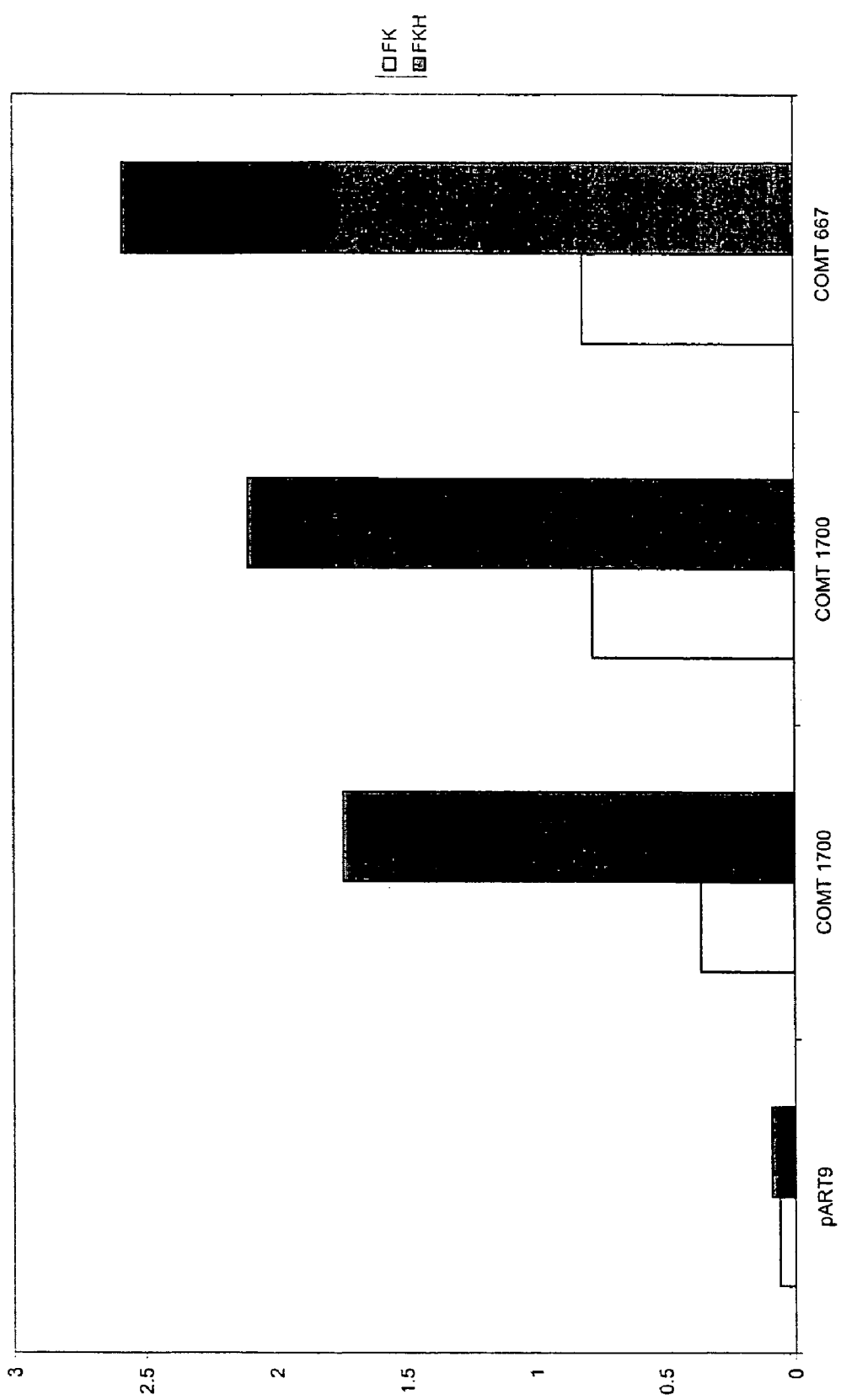
FIG. 3. Comparison of the promoter activity of a sequence comprising the full length 5' UTR of SEQ ID 113 (nucleotides 1-1643; cOMT 1700) with the promoter activity of SEQ ID NO: 12 (cOMT 667) in the Zinnia TE cell based assay system. pART9 is the empty vector control. The fluorescence is represented as arbitrary fluorescence units (FU) per microgram protein per minute.

The present invention provides vascular tissue-specific isolated polynucleotide regulatory regions of the *Eucalyptus grandis* cOMT gene which may be used for the modification of plant phenotypes. As discussed above, promoters are components of the cellular "transcription apparatus" and are involved in the regulation of gene expression. Both tissue- and temporal-specific gene expression patterns have been shown to be initiated and controlled by promoters during the natural development of a plant. The isolated polynucleotide promoter sequences of the present invention may thus be employed in the modification of growth and development of plants, in particular, to selectively modulate the expression of genes involved in secondary cell wall formation in plants, such as those disclosed in U.S. patent application Ser. No. 10/198,232, filed Jul. 17, 2002. For example, the promoter sequences of the present invention may be used for eliminating or reducing lignification (and increasing cellulose deposition) in secondary xylem, increasing the thickness of the secondary cell wall, and controlling the sites and levels of lignification and cellulose deposition in a plant.

Using the methods and materials of the present invention, the amount of a specific polypeptide of interest may be increased or reduced by incorporating additional copies of genes, or coding sequences, encoding the polypeptide, operably linked to an inventive promoter sequence, into the genome of a target organism, such as a plant. Similarly, an increase or decrease in the amount of the polypeptide may be obtained by transforming the target plant with antisense copies or direct repeats or inverted repeats of such genes.

In one of its aspects, the present invention provides an isolated polynucleotide sequence comprising a vascular tissue-specific promoter of the *E. grandis* cOMT gene, and functional promoter fragments thereof. In a preferred embodiment, the polynucleotide sequence is selected from the group consisting of:
 (a) the sequences recited in SEQ ID NO: 12 and SEQ ID 113, nucleotides 1019-1643, and their complements;
 (b) reverse complements of the sequences recited in (a);
 (c) reverse sequences of the sequences recited in (a);
 (d) sequences having at least 75% identity to a sequence recited in (a);
 (e) sequences having at least 90% identity to a sequence recited in (a);
 (f) a polynucleotide sequence that hybridizes to a polynucleotide sequence of (a) above under stringent conditions; and
 (g) a polynucleotide comprising a 20-mer, a 40-mer, a 60-mer, an 80-mer, a 100-mer, a 120-mer, a 150-mer, a 180-mer, a 220-mer, a 250-mer, a 300-mer, 400-mer, 500-mer or 600-mer of a sequence recited in (a) or (e) above.

In another embodiment, the polynucleotide sequence comprises a sequence recited in SEQ ID NO. 60 and its complement, reverse sequence, reverse complement, and sequences having at least 90% identity to these sequences.

It should be understood that the term "percent identity", as used herein, and method of calculating percent identity, are disclosed in the specification.

Polynucleotide sequences comprising a *E. grandis* cOMT promoter are shown in FIGS. 1 and 2, and in SEQ ID NO. 12, 60 and 113 (nucleotides 1019-1643) of the Sequence Listing.

The motifs shown in FIG. 1 are considered to be putative cis-elements for the *E. grandis* cOMT promoters based on their similarity to known vascular specific factor-like and AC rich elements in other plant gene promoters. The sequence recited in SEQ ID NO. 12, nucleotides 1-661, is 98.9% identical to the promoter comprising sequence of SEQ ID NO. 113 (nucleotides 1019-1676). Polynucleotides comprising sequences that differ from the polynucleotide sequence recited in SEQ ID NO: 12, its complement, reverse complement or reverse sequence, as a result of deletions and/or insertions totaling less than 10% of the total sequence length are also contemplated by and encompassed within the present invention. In certain embodiments, variants of the inventive polynucleotides possess biological activities that are the same or similar to those of the inventive polynucleotides. Such variant polynucleotides function as promoter sequences and are thus capable of modifying gene expression in a plant.

Functional fragments of SEQ ID NO. 12 and their variants having at least 90% identity are intended to be encompassed by the present invention. Functional promoter fragments can be identified by those skilled in the art using conventional deletion analysis methods and the functional assay methods described in Examples 2 and 3.

The promoter activity of the 5' noncoding region of SEQ ID NO. 113, nucleotides 1-1643 (cOMT 1700) and of SEQ ID NO: 12 (cOMT 667) in a cell based tracheary element (TE)-forming system was demonstrated by transfecting *Zinnia elegans* mesophyll cells with promoter-GUS constructs and comparing GUS expression under inducing and noninducing conditions (Example 2). As is shown in FIG. 3, the expression of GUS driven by each of the above-identified sequences was much greater under TE inducing conditions than under maintenance conditions. cOMT 667 was at least as active as cOMT 1700. This experiment supported the identification of the cOMT sequence as a xylem-specific promoter.

Figure 4:
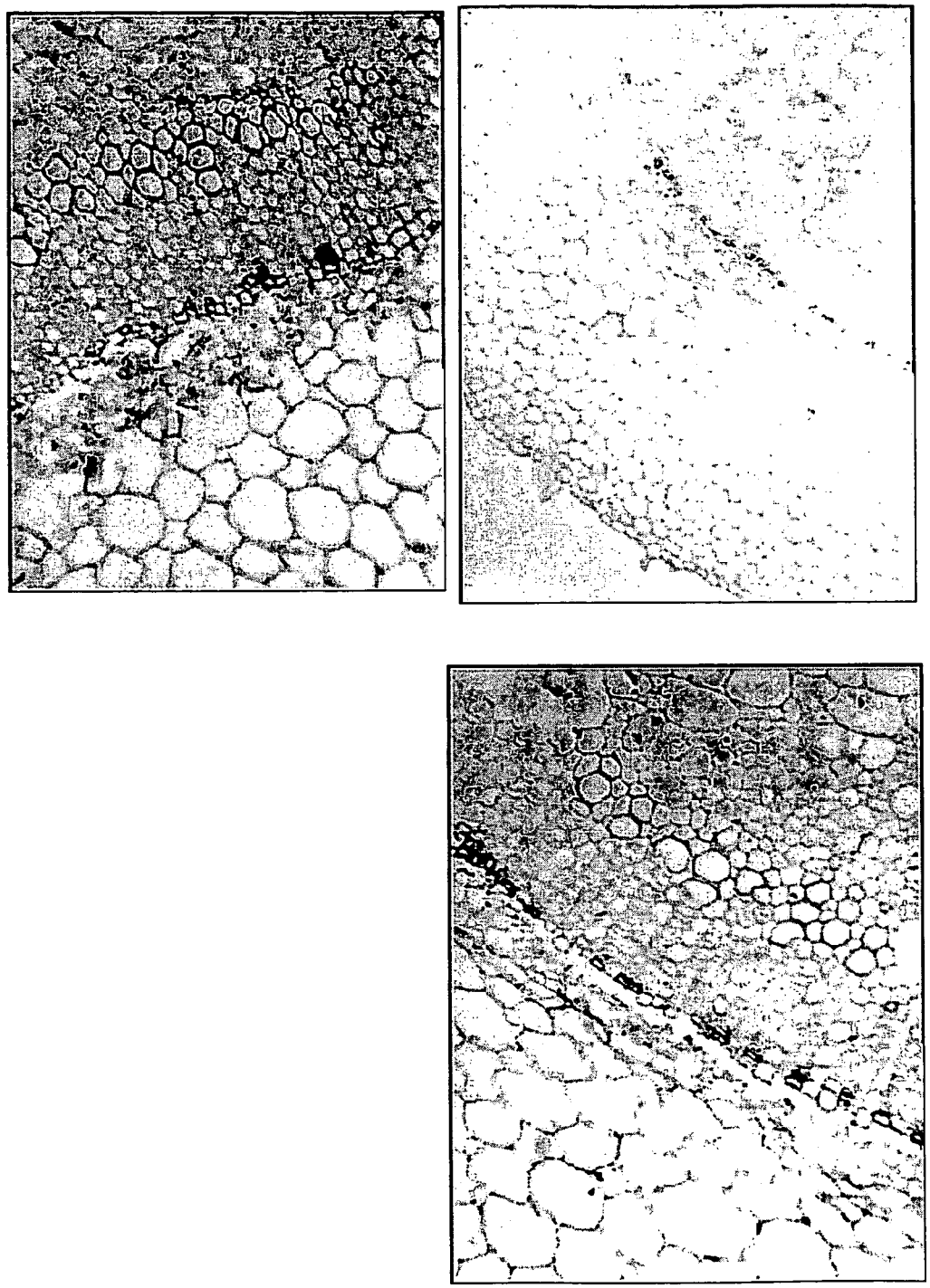
FIG. 4. Vascular-specific expression of an *E. grandis* OMT Promoter-GUS construct in transformed *Nicotiana benthamiana*. The GUS sequence was expressed under the control of nucleotides 1-1643 of SEQ ID NO. 113. Paraffin-embedded sections of the stem were stained for GUS and counterstained with Safronin O to highlight the GUS staining. Staining was observed in differentiating cambial cells and xylem.
Figure 14:
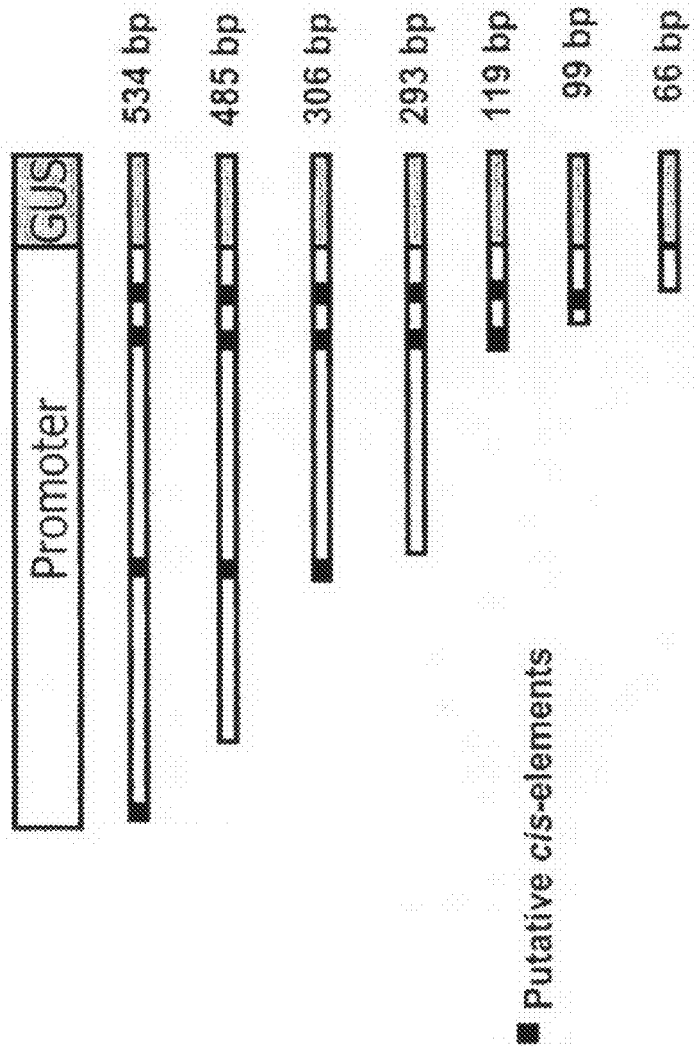
FIG. 14. Schematic diagram of the *E. grandis* promoter fragments showing the locations of the putative cis-elements.

Further experiments were performed by in planta analysis of the above promoter-GUS constructs in tobacco plants, as described in Example 3. FIGS. 4 and 5 show GUS stained sections of transformed tobacco plants. These experiments confirmed the vascular tissue-specific activity of the promoter.

The term "polynucleotide(s)," as used herein, means a single or double-stranded polymer of deoxyribonucleotide or ribonucleotide bases and includes DNA and corresponding RNA molecules, including HnRNA and mRNA molecules, both sense and anti-sense strands, and comprehends cDNA, genomic DNA and recombinant DNA, as well as wholly or partially synthesized polynucleotides. An HnRNA molecule contains introns and corresponds to a DNA molecule in a generally one-to-one manner. An mRNA molecule corresponds to an HnRNA and DNA molecule from which the introns have been excised. A polynucleotide may consist of an entire gene, or any portion thereof. Operable anti-sense polynucleotides may comprise a fragment of the corresponding polynucleotide, and the definition of "polynucleotide" therefore includes all such operable anti-sense fragments. Anti-sense polynucleotides and techniques involving anti-sense polynucleotides are well known in the art and are described, for example, in Robinson-Benion et al., "Antisense techniques," *Methods in Enzymol*. 254:363-375, 1995; and Kawasaki et al., in *Artific. Organs* 20:836-848, 1996.

All of the polynucleotides described herein are isolated and purified, as those terms are commonly used in the art. Preferably, the polynucleotides are at least about 80% pure, more preferably at least about 90% pure, and most preferably at least about 99% pure.

The definition of the terms "complement", "reverse complement" and "reverse sequence", as used herein, is best illustrated by the following example. For the sequence 5' AGGACC 3', the complement, reverse complement and reverse sequence are as follows:

```
Complement          3' TCCTGG 5'
Reverse complement  3' GGTCCT 5'
Reverse sequence    5' CCAGGA 3'
```

As used herein, the term "variant" comprehends nucleotide sequences different from the specifically identified sequences, wherein one or more nucleotides is deleted, substituted, or added. Variants may be naturally occurring allelic variants, or non-naturally occurring variants. Variant sequences preferably exhibit at least 50%, more preferably at least 75%, and most preferably at least 90% identity to a sequence of the present invention. The percentage identity is determined by aligning the two sequences to be compared as described below, determining the number of identical nucleotides in the aligned portion, dividing that number by the total number of residues in the inventive (queried) sequence, and multiplying the result by 100.

Polynucleotide sequences may be aligned, and percentage of identical residues in a specified region may be determined against other polynucleotide sequences, using computer algorithms that are publicly available. Two exemplary algorithms for aligning and identifying the similarity of polynucleotide sequences are the BLASTN and FASTA algorithms. The BLASTN algorithm Version 2.0.11 [Jan. 20, 2000], or later versions, set to the default parameters described in the documentation and distributed with the algorithm, are preferred for use in the determination of polynucleotide variants according to the present invention. The use of the BLAST family of algorithms, including BLASTN, BLASTP, and BLASTX, is described in the publication of Altschul et al., "Gapped BLAST and PSI-BLAST: a new generation of protein database search programs," *Nucleic Acids Res.* 25: 3389-3402, 1997. The BLASTN software is available on the NCBI anonymous FTP server (ftp://ncbi.nlm.nih.gov) under /blast/executables/ and is available from the National Center for Biotechnology Information (NCBI), National Library of Medicine, Building 38A, Room 8N805, Bethesda, Md. 20894 USA.

The FASTA software package is available from the University of Virginia (University of Virginia, PO Box 9025, Charlottesville, Va. 22906-9025). Version 2.0u4, February 1996, or later versions, set to the default parameters described in the documentation and distributed with the algorithm, may be used in the determination of variants according to the present invention. The use of the FASTA algorithm is described in Pearson and Lipman, "Improved Tools for Biological Sequence Analysis," *Proc. Natl. Acad. Sci. USA* 85:2444-2448, 1988; and Pearson, "Rapid and Sensitive Sequence Comparison with FASTP and FASTA," *Methods in Enzymol.* 183:63-98, 1990.

The following running parameters are preferred for determination of alignments and similarities using BLASTN that contribute to the E values and percentage identity for polynucleotide sequences: Unix running command: blastall -p blastn -d embldb -e 10 -G0 -FF -E0 -r 1 -v 30 -b 30 -i queryseq -o results; the parameters are: -p Program Name [String]; -d Database [String]; -e Expectation value (E) [Real]; -G Cost to open a gap (zero invokes default behavior) [Integer]; -FF low complexity filter; -E Cost to extend a gap (zero invokes default behavior) [Integer]; -r Reward for a nucleotide match (BLASTN only) [Integer]; -v Number of one-line descriptions (V) [Integer]; -b Number of alignments to show (B) [Integer]; -i Query File [File In]; and -o BLAST report Output File [File Out] Optional.

The "hits" to one or more database sequences by a queried sequence produced by BLASTN and FASTA or a similar algorithm, align and identify similar portions of sequences. The hits are arranged in order of the degree of similarity and the length of sequence overlap. Hits to a database sequence generally represent an overlap over only a fraction of the sequence length of the queried sequence.

The BLASTN and FASTA algorithms also produce "Expect" values for alignments. The Expect value (E) indicates the number of hits one can "expect" to see over a certain number of contiguous sequences by chance when searching a database of a certain size. The Expect value is used as a significance threshold for determining whether the hit to a database, such as the preferred EMBL database, indicates true similarity. For example, an E value of 0.1 assigned to a polynucleotide hit is interpreted as meaning that in a database of the size of the EMBL database, one might expect to see 0.1 matches over the aligned portion of the sequence with a similar score simply by chance. By this criterion, the aligned and matched portions of the polynucleotide sequences then have a probability of 90% of being the same. For sequences having an E value of 0.01 or less over aligned and matched portions, the probability of finding a match by chance in the EMBL database is 1% or less using the BLASTN or FASTA algorithm.

According to one embodiment, "variant" polynucleotides, with reference to each of the polynucleotides of the present invention, preferably comprise sequences having the same number or fewer bases than each of the polynucleotides of the present invention and producing an E value of 0.01 or less when compared to the polynucleotide of the present invention. That is, a variant polynucleotide or polypeptide is any sequence that has at least a 99% probability of being the same as the polynucleotide or polypeptide of the present invention, measured as having an E value of 0.01 or less using the BLASTN or FASTA algorithms set at parameters described above. According to a preferred embodiment, a variant polynucleotide is a sequence having the same number or fewer nucleic acids than a polynucleotide of the present invention that has at least a 99% probability of being the same as the polynucleotide of the present invention, measured as having an E value of 0.01 or less using the BLASTN or FASTA algorithms set at parameters described above.

Alternatively, variant polynucleotides of the present invention hybridize to the polynucleotide sequences recited in SEQ ID NO. 12 and SEQ ID NO. 113, nucleotides 1019-1643, or complements, reverse sequences, or reverse complements of those sequences under stringent conditions. An example of "stringent conditions" is prewashing in a solution of 6×SSC, 0.2% SDS; hybridizing at 65° C., 6×SSC, 0.2% SDS overnight; followed by two washes of 30 minutes each in 1×SSC, 0.1% SDS at 65° C. and two washes of 30 minutes each in 0.2×SSC, 0.1% SDS at 65° C. See discussion below relating to substantial complementarity of nucleotide sequences.

The present invention also encompasses polynucleotides comprising sequences that differ from the polynucleotide sequence recited in SEQ ID NO: 12, or SEQ ID NO. 113, nucleotides 1019-1643, or complements, reverse complements or reverse sequences thereof, as a result of deletions and/or insertions totaling less than 10% of the total sequence length are also contemplated by and encompassed within the present invention. In certain embodiments, variants of the inventive polynucleotides possess biological activities that are the same or similar to those of the inventive polynucleotides. Such variant polynucleotides function as promoter sequences and are thus capable of modifying gene expression in a plant.

The polynucleotides of the present invention may be isolated from various libraries, or may be synthesized using techniques that are well known in the art. The polynucleotides may be synthesized, for example, using automated oligonucleotide synthesizers (e.g., Beckman Oligo 1000M DNA Synthesizer) to obtain polynucleotide segments of up to 50 or more nucleic acids. A plurality of such polynucleotide segments may then be ligated using standard DNA manipulation techniques that are well known in the art of molecular biology. One conventional and exemplary polynucleotide synthesis technique involves synthesis of a single stranded polynucleotide segment having, for example, 80 nucleic acids, and hybridizing that segment to a synthesized complementary 85 nucleic acid segment to produce a 5-nucleotide overhang. The next segment may then be synthesized in a similar fashion, with a 5-nucleotide overhang on the opposite strand. The "sticky" ends ensure proper ligation when the two portions are hybridized. In this way, a complete polynucleotide of the present invention may be synthesized entirely in vitro.

Polynucleotides of the present invention also comprehend polynucleotides comprising at least a specified number of contiguous residues (x-mers) of any of the polynucleotides identified as SEQ ID NO: 12 or SEQ ID NO. 113, nucleotides 1019-1643, complements, reverse sequences, and reverse complements of such sequences, and their variants. As used herein, the term "x-mer," with reference to a specific value of "x," refers to a sequence comprising at least a specified number ("x") of contiguous residues of any of the polynucleotides identified as SEQ ID NO: 12 or SEQ ID NO. 113, nucleotides 1019-1643. According to preferred embodiments, the value of x is preferably at least 20, more preferably at least 40, more preferably yet at least 60, and most preferably at least 80. Thus, polynucleotides of the present invention comprise a 20-mer, a 40-mer, a 60-mer, an 80-mer, a 100-mer, a 120-mer, a 150-mer, a 180-mer, a 220-mer, a 250-mer, a 300-mer, 400-mer, 500-mer or 600-mer of a polynucleotide identified as SEQ ID NO: 12 or SEQ ID NO. 113, nucleotides 1019-1643 and variants thereof.

As noted above, the inventive polynucleotide promoter sequences may be employed in genetic constructs to drive transcription and/or expression of a polynucleotide of interest. The technology involved in making expression constructs comprising the open reading frames and suitable promoters, initiators, terminators, etc., is well known in the art and can be practiced by those of ordinary skill in the art without undue experimentation. The constructs may be introduced into a host cell to express the polypeptide encoded by the open reading frame. Suitable host cells may include various prokaryotic and eukaryotic cells, including plant cells, bacterial cells, algae and the like. Procedures for transforming cells are also well known in the art and can be practiced by those of ordinary skill in the art without undue experimentation.

The polynucleotide sequence of interest may be endogenous or heterologous to the organism to be transformed, for example, a plant. The inventive genetic constructs may thus be employed to modulate levels of transcription and/or expression of a polynucleotide, for example, a gene that is present in the wild-type plant, or may be employed to provide transcription and/or expression of a polynucleotide sequence that is not normally found in the wild-type plant.

In certain embodiments, the polynucleotide of interest comprises an open reading frame that encodes a target polypeptide. Open reading frames may be identified using techniques that are well known in the art. These techniques include, for example, analysis for the location of known start and stop codons, most likely reading frame identification based on codon frequencies, etc. Suitable tools and software for ORF analysis include, for example, "GeneWise", available from the Sanger Center, Wellcome Trust Genome Campus, Hinxton, Cambridge, CB10 ISA, United Kingdom; "Diogenes", available from Computational Biology Centers, University of Minnesota, Academic Health Center, UMHG Box 43, Minneapolis, Minn. 55455 and "GRAIL", available from the Informatics Group, Oak Ridge National Laboratories, Oak Ridge, Tenn. The open reading frame is inserted in the genetic construct in either a sense or antisense orientation, such that transformation of a target plant with the genetic construct will lead to a change in the amount of polypeptide compared to the wild-type plant. Transformation with a genetic construct comprising an open reading frame in a sense orientation will generally result in over-expression of the selected polypeptide, while transformation with a genetic construct comprising an open reading frame in an antisense orientation will generally result in reduced expression of the selected polypeptide. A population of plants transformed with a genetic construct comprising an open reading frame in either a sense or antisense orientation may be screened for increased or reduced expression of the polypeptide in question using techniques well known to those of skill in the art, and plants having the desired phenotypes may thus be isolated.

Alternatively, expression of a target polypeptide may be inhibited by inserting a portion of the open reading frame, in either sense or antisense orientation, in the genetic construct. Such portions need not be full-length but preferably comprise at least 25 and more preferably at least 50 residues of the open reading frame. A much longer portion or even the full length DNA corresponding to the complete open reading frame may be employed. The portion of the open reading frame does not need to be precisely the same as the endogenous sequence, provided that there is sufficient sequence similarity to achieve inhibition of the target gene. Thus a sequence derived from one species may be used to inhibit expression of a gene in a different species.

In one embodiment, RNAi expression constructs comprising partial or fill-length coding sequences homologous to endogenous genes are used to downregulate the expression of these genes, for example, genes involved in biosynthesis of lignin. Representative examples of RNAi silencing methods can be found in, but are not limited to, the following patent applications and publications: PCT Applications WO 99/49029, WO 98/36083, WO 99/15682, WO 98/53083, WO 99/53050, WO 00/49035, WO 01/77350, WO01/94603, WO02/00894, WO01/75164, and WO01/68836; Waterhouse et al., *Proc. Natl. Acad. Sci. USA* 95: 13959-13964 (1998).

In further embodiments, the inventive genetic constructs comprise a polynucleotide including an untranslated, or non-coding, region of a gene coding for a target polypeptide, or a polynucleotide complementary to such an untranslated region. Examples of untranslated regions which may be usefully employed in such constructs include introns and 5'-untranslated leader sequences. Transformation of a target plant with such a genetic construct may lead to a reduction in the amount of the polypeptide expressed in the plant by the process of cosuppression, in a manner similar to that discussed, for example, by Napoli et al., *Plant Cell* 2:279-290, 1990 and de Carvalho Niebel et al., *Plant Cell* 7:347-358, 1995.

The present invention also contemplates using a genetic construct to produce gene knockouts by transcriptional gene silencing, for example, a construct comprising an inverted repeat of a promoter sequence or a promoter fragment of the present invention under the control of a different promoter (see, e.g., Mette et al., *EMBO J.* 19: 5194-5201, 2000).

In one embodiment of the invention, the polynucleotide of interest, such as a coding sequence in sense or antisense orientation, is operably linked to a polynucleotide promoter sequence of the present invention such that the promoter directs transcription of the coding sequence in vascular tissues, preferably xylem or a tissue involved in xylogenesis (e.g., cambium initials of vascular cambium). The polynucleotide promoter sequence is generally positioned at the 5' end of the polynucleotide to be transcribed. The promoter can be employed to modulate gene transcription during xylem development in a transformed plant.

The properties of the cOMT promoter, e.g., its strength and inducibility or hormone responsiveness, can be modified by deletion, insertion, rearrangement or mutation of cis-acting elements to obtain new or improved properties (e.g., activation by external stimuli, such as light, heat, anaerobic stress, alteration in nutrient conditions, chemicals and the like).

The inventive genetic constructs further comprise a gene termination sequence which is located 3' to the polynucleotide of interest. A variety of gene termination sequences which may be usefully employed in the genetic constructs of the present invention are well known in the art. One example of such a gene termination sequence is the 3' end of the *Agrobacterium tumefaciens* nopaline synthase gene. The gene termination sequence may be endogenous to the target plant or may be exogenous, provided the promoter is functional in the target plant. For example, the termination sequence may be obtained from other plant species, plant viruses, bacterial plasmids and the like.

The genetic constructs of the present invention may also contain a selection marker that is effective in cells of the target organism, such as a plant, to allow for the detection of transformed cells containing the inventive construct. Such markers, which are well known in the art, typically confer resistance to one or more toxins. One example of such a marker is the NPTII gene whose expression results in resistance to kanamycin or hygromycin, antibiotics which are usually toxic to plant cells at a moderate concentration (Rogers et al., in Weissbach A and H, eds. *Methods for Plant Molecular Biology*, Academic Press Inc.: San Diego, Calif., 1988). Transformed cells can thus be identified by their ability to grow in media containing the antibiotic in question. Alternatively, the presence of the desired construct in transformed cells can be determined by means of other techniques well known in the art, such as Southern and Western blots.

Techniques for operatively linking the components of the inventive genetic constructs are well known in the art and include the use of synthetic linkers containing one or more restriction endonuclease sites as described, for example, by Sambrook et al., *Molecular cloning: a laboratory manual*, CSHL Press: Cold Spring Harbor, N.Y., 1989. The genetic construct of the present invention may be linked to a vector having at least one replication system, for example *E. coli*, whereby after each manipulation, the resulting construct can be cloned and sequenced and the correctness of the manipulation determined.

The genetic constructs of the present invention may be used to transform a variety of target organisms including, but not limited to, plants. Plants which may be transformed using the inventive constructs include both monocotyledonous angiosperms (e.g., grasses, corn, grains, oat, wheat and barley) and dicotyledonous angiosperms (e.g., *Arabidopsis*, tobacco, legumes, alfalfa, oaks, eucalyptus, maple), and Gymnosperms (e.g., Scots pine; see Aronen, *Finnish Forest Res. Papers*, Vol. 595, 1996), white spruce (Ellis et al., *Biotechnology* 11:84-89, 1993), and larch (Huang et al., In Vitro Cell 27:201-207, 1991). In a preferred embodiment, the inventive genetic constructs are employed to transform grasses and woody plants. Woody plants are herein defined as a tree or shrub whose stem lives for a number of years and increases in diameter each year by the addition of woody tissue. Preferably the woody plant is selected from the group consisting of eucalyptus and pine species, most preferably from the group consisting of *Eucalyptus grandis* and *Pinus radiata*. Other preferred species include Poplar, sugarcane, forage grasses and *Salix* spp. Other species which may be usefully transformed with the genetic constructs of the present invention include, but are not limited to: pines such as *Pinus banksiana, Pinus brutia, Pinus caribaea, Pinus clausa, Pinus contorta, Pinus coulteri, Pinus echinata, Pinus eldarica, Pinus ellioti, Pinus jeffreyi, Pinus lambertiana, Pinus monticola, Pinus nigra, Pinus palustrus, Pinus pinaster, Pinus ponderosa, Pinus resinosa, Pinus rigida, Pinus serotina, Pinus strobus, Pinus sylvestris, Pinus taeda, Pinus virginiana*; other gymnosperms, such as *Abies amabilis, Abies balsamea, Abies concolor, Abies grandis, Abies lasiocarpa, Abies magnifica, Abies procera, Chamaecyparis lawsoniona, Chamaecyparis nootkatensis, Chamaecyparis thyoides, Juniperus virginiana, Larix decidua, Larix laricina, Larix leptolepis, Larix occidentalis, Larix siberica, Libocedrus decurrens, Picea abies, Picea engelmanni, Picea glauca, Picea mariana, Picea pungens, Picea rubens, Picea sitchensis, Pseudotsuga menziesii, Sequoia gigantea, Sequoia sempervirens, Taxodium distichum, Tsuga canadensis, Tsuga heterophylla, Tsuga mertensiana, Thuja occidentalis, Thuja plicata*; and *Eucalypts*, such as *Eucalyptus alba, Eucalyptus bancroftii, Eucalyptus botyroides, Eucalyptus bridgesiana, Eucalyptus calophylla, Eucalyptus camaldulensis, Eucalyptus citriodora, Eucalyptus cladocalyx, Eucalyptus coccifera, Eucalyptus curtisii, Eucalyptus dalrympleana, Eucalyptus deglupta, Eucalyptus delagatensis, Eucalyptus diversicolor, Eucalyptus dunnii, Eucalyptus ficifolia, Eucalyptus globulus, Eucalyptus gomphocephala, Eucalyptus gunnii, Eucalyptus henryi, Eucalyptus laevopinea, Eucalyptus macarthurii, Eucalyptus macrorhyncha, Eucalyptus maculata, Eucalyptus marginata, Eucalyptus megacarpa, Eucalyptus melliodora, Eucalyptus nicholii, Eucalyptus nitens, Eucalyptus nova-anglica, Eucalyptus obliqua, Eucalyptus obtusiflora, Eucalyptus oreades, Eucalyptus pauciflora, Eucalyptus polybractea, Eucalyptus regnans, Eucalyptus resinifera, Eucalyptus robusta, Eucalyptus rudis, Eucalyptus saligna, Eucalyptus sideroxylon, Eucalyptus stuartiana, Eucalyptus tereticornis, Eucalyptus torelliana, Eucalyptus urnigera, Eucalyptus urophylla, Eucalyptus viminalis, Eucalyptus viridis, Eucalyptus wandoo* and *Eucalyptus youmanni*; and hybrids of any of these species.

Techniques for stably incorporating genetic constructs into the genome of target plants are well known in the art and include *Agrobacterium tumefaciens* mediated introduction, electroporation, protoplast fusion, injection into reproductive organs, injection into immature embryos, high velocity projectile introduction and the like. The choice of technique will depend upon the target plant to be transformed. For example, dicotyledonous plants and certain monocots and gymnosperms may be transformed by *Agrobacterium* Ti plasmid technology, as described, for example by Bevan, *Nucleic Acids Res.* 12:8711-8721, 1984. Targets for the introduction of the genetic constructs of the present invention include tissues, such as leaf tissue, dissociated cells, protoplasts, seeds, embryos, meristematic regions; cotyledons, hypocotyls, and the like. The preferred method for transforming eucalyptus and pine is a biolistic method using pollen (see, for example, Aronen, *Finnish Forest Res. Papers*, Vol. 595, 53 pp, 1996) or easily regenerable embryonic tissues.

Once the cells are transformed, cells having the inventive genetic construct incorporated in their genome may be selected by means of a marker, such as the kanamycin resistance marker discussed above. Transgenic cells may then be cultured in an appropriate medium to regenerate whole plants, using techniques well known in the art. In the case of protoplasts, the cell wall is allowed to reform under appropriate osmotic conditions. In the case of seeds or embryos, an appropriate germination or callus initiation medium is employed. For explants, an appropriate regeneration medium is used. Regeneration of plants is well established for many species. For a review of regeneration of forest trees see Dunstan et al., "Somatic embryogenesis in woody plants," in Thorpe TA, ed., *In Vitro Embryogenesis of Plants (Current Plant Science and Biotechnology in Agriculture Vol.* 20), Chapter 12, pp. 471-540, 1995. Specific protocols for the regeneration of spruce are discussed by Roberts et al., "Somatic embryogenesis of spruce," in Redenbaugh K, ed., *Synseed: applications of synthetic seed to crop improvement*, CRC Press: Chapter 23, pp. 427-449, 1993). Transformed plants having the desired phenotype may be selected using techniques well known in the art. The resulting transformed plants may be reproduced sexually or asexually, using methods well known in the art, to give successive generations of transgenic plants.

As discussed above, the production of RNA in target cells can be controlled by choice of the promoter sequence, or by selecting the number of functional copies or the site of integration of the polynucleotides incorporated into the genome of the target host. A target organism may be transformed with more than one genetic construct of the present invention, thereby modulating the activity of more than gene. Similarly, a genetic construct may be assembled containing more than one open reading frame coding for a polypeptide of interest or more than one untranslated region of a gene coding for such a polypeptide.

The isolated polynucleotides of the present invention and their variants may be used to design oligonucleotide probes and primers, for use in detecting and isolating xylem-specific promoters of genes in other plant species. Oligonucleotide probes and primers designed using the polynucleotides of the present invention may also be used in connection with various microarray technologies, including the microarray technology of Affymetrix (Santa Clara, Calif.).

The term "vascular tissue-specific promoter" refers to a promoter expressed in vascular tissue of a plant, for example, xylem, phloem or vascular cambium which gives rise to these tissues. For purposes of the present application, vascular tissue-specific refers to a promoter which is preferentially expressed in xylem, phloem or cambium.

As used herein, the term "oligonucleotide" refers to a relatively short segment of a polynucleotide sequence, generally comprising between 6 and 60 nucleotides, and comprehends both probes for use in hybridization assays and primers for use in the amplification of DNA by polymerase chain reaction.

An oligonucleotide probe or primer is described as "corresponding to" a polynucleotide of the present invention, including one of the sequences set out as SEQ ID NO: 12, or SEQ ID NO. 113, nucleotides 1019-1643, or a variant thereof, if the oligonucleotide probe or primer, or its complement, is contained within one of the inventive promoter sequences, or a variant thereof. Oligonucleotide probes and primers of the present invention are substantially complementary to a polynucleotide disclosed herein.

Two single stranded sequences are said to be substantially complementary when the nucleotides of one strand, optimally aligned and compared, with the appropriate nucleotide insertions and/or deletions, pair with at least 80%, preferably at least 90% to 95% and more preferably at least 98% to 100% of the nucleotides of the other strand. Alternatively, substantial complementarity exists when a first DNA strand will selectively hybridize to a second DNA strand under stringent hybridization conditions. Stringent hybridization conditions for determining complementarity include salt conditions of less than about 1 M, more usually less than about 500 mM, and preferably less than about 200 mM. Hybridization temperatures can be as low as 5° C., but are generally greater than about 22° C., more preferably greater than about 30° C., and most preferably greater than about 37° C. Longer DNA fragments may require higher hybridization temperatures for specific hybridization. Since the stringency of hybridization may be affected by other factors such as probe composition, presence of organic solvents and extent of base mismatching, the combination of parameters is more important than the absolute measure of any one alone.

In specific embodiments, the oligonucleotide probes and/or primers comprise at least about 6 contiguous residues, more preferably at least about 10 contiguous residues, and most preferably at least about 20 contiguous residues complementary to a polynucleotide sequence of the present invention. Probes and primers of the present invention may be from about 8 to 100 base pairs in length or, preferably from about 10 to 50 base pairs in length or, more preferably from about 15 to 40 base pairs in length. The probes can be easily selected using procedures well known in the art, taking into account DNA-DNA hybridization stringencies, annealing and melting temperatures, and potential for formation of loops and other factors, which are well known in the art. Preferred techniques for designing PCR primers are disclosed in Dieffenbach, C W and Dyksler, G S. *PCR Primer: a laboratory manual*, CSHL Press: Cold Spring Harbor, N.Y., 1995. A software program suitable for designing probes, and especially for designing PCR primers, is available from Premier Biosoft International, 3786 Corina Way, Palo Alto, Calif. 94303-4504.

A plurality of oligonucleotide probes or primers corresponding to a polynucleotide of the present invention may be provided in a kit form. Such kits generally comprise multiple DNA or oligonucleotide probes, each probe being specific for a polynucleotide sequence. Kits of the present invention may comprise one or more probes or primers corresponding to a polynucleotide of the present invention.

In one embodiment useful for high-throughput assays, the oligonucleotide probe kits of the present invention comprise multiple probes in an array format, wherein each probe is immobilized at a predefined, spatially addressable location on the surface of a solid substrate. Array formats which may be usefully employed in the present invention are disclosed, for example, in U.S. Pat. Nos. 5,412,087 and 5,545,451; and PCT Publication No. WO 95/00450, the disclosures of which are hereby incorporated by reference.

EXAMPLES

The following examples are offered by way of illustration and not by way of limitation.

Example 1

Isolation of an O-Methyl Transferase Promoter from Eucalyptus grandis

E. grandis cDNA expression libraries were constructed and screened as follows. mRNA was extracted from plant tissue using the protocol of Chang et al., Plant Molecular Biology Reporter 11:113-116, 1993 with minor modifications. Specifically, samples were dissolved in CPC—RNAXB (100 mM Tris-Cl, pH 8,0; 25 mM EDTA; 2.0 M NaCl; 2% CTAB; 2% PVP and 0.05% Spermidine*3HCl) and extracted with chloroform:isoamyl alcohol, 24:1. mRNA was precipitated with ethanol and the total RNA preparate was purified using a Poly(A) Quik mRNA Isolation Kit (Stratagene, La Jolla, Calif.). A cDNA expression library was constructed from the purified mRNA by reverse transcriptase synthesis followed by insertion of the resulting cDNA clones in Lambda ZAP using a ZAP Express cDNA Synthesis Kit (Stratagene), according to the manufacturer's protocol. The resulting cDNAs were packaged using a Gigapack II Packaging Extract (Stratagene) employing 1 µl of sample DNA from the 5 µl ligation mix. Mass excision of the library was done using XL1-Blue MRF' cells and XLOLR cells (Stratagene) with ExAssist helper phage (Stratagene). The excised phagemids were diluted with NZY broth (Gibco BRL, Gaithersburg, Md.) and plated out onto LB-kanamycin agar plates containing 5-bromo-4-chloro-3-indolyl-beta-D-galactosidase (X-gal) and isopropylthio-beta-galactoside (IPTG).

Of the colonies plated and picked for DNA miniprep, 99% contained an insert suitable for sequencing. Positive colonies were cultured in NZY broth with kanamycin and cDNA was purified by means of alkaline lysis and polyethylene glycol (PEG) precipitation. Agarose gel at 1% was used to screen sequencing templates for chromosomal contamination. Dye primer sequences were prepared using a Turbo Catalyst 800 machine (Perkin Elmer/Applied Biosystems Division, Foster City, Calif.) according to the manufacturer's protocol.

DNA sequences for positive clones was obtained using a Perkin Elmer/Applied Biosystems Division Prism 377 sequencer. cDNA clones were sequenced first from the 5' end and, in some cases, also from the 3' end. For some clones, internal sequence was obtained using subcloned fragments. Subcloning was performed using standard procedures of restriction mapping and subcloning to pBluescript II SK+ vector.

Plant polynucleotide sequences homologous to a caffeic acid O-methyl transferase (cOMT) gene, which encodes an enzyme that functions in lignin synthesis, were isolated from a Eucalyptus grandis cDNA expression library. Analysis by PCR and DNA sequencing confirmed the identity of these sequences. Using the "Genome Walker" kit (Clontech, Palo Alto, Calif.) and gene specific primers designed from the plant polynucleotide sequence, 5'UTR sequences containing the promoter of the E. grandis OMT gene were isolated from genomic DNA and were extended by further sequencing. The determined nucleotide sequence is given in SEQ ID NO: 12. FIG. 1 shows the cOMT promoter sequence (SEQ ID NO. 12), with putative cis-regulatory motifs. This promoter sequence was extended by further sequencing. The extended cDNA sequences are given in SEQ ID NO: 60 and 113. FIG. 2 shows the full length polynucleotide sequence which includes the 5'UTR comprising the promoter sequence (in bold type), and the coding sequence.

Example 2

Analysis of Promoter Activity using the Zinnia Tracheary Element (TE) Assay

Zinnia elegans mesophyll cells were cultured in maintenance medium (FK) or TE inducing medium (FKH) as described previously (WO 03/040,403, which is incorporated herein by reference in its entirety). Protoplasts were isolated and transformed with a plasmid comprising the GUS (β-D-glucuronidase) reporter gene in frame with E. grandis cOMT promoter-containing sequences, as follows.

Zinnia protoplasts in 24% sucrose solution were overlaid with 1 ml of W5 solution and centrifuged at 70×g for 10 minutes at 20° C. with brakes off. Floating protoplasts were harvested and resuspended in 10 ml of W5 solution. Protoplasts were pelleted by centrifuging at 70×g for 10 minutes at 20° C. Protoplasts were resuspended in MaMg medium (density=~5×10$^6$ protoplasts/ml) and aliquoted into individual 15 ml tubes (300 µL: 1.5×10$^6$ protoplasts). 5 µg DNA (of each construct) and 50 µg Salmon Testes DNA was added to the protoplast suspension, mixed and incubated for 5 minutes at 20° C. 300 µl 40% PEG solution was added to each aliquot of protoplasts, mixed and incubated for 20 minutes at 20° C. 5 ml of K3/0.4M sucrose was added to each aliquot of leaf-derived transfected protoplasts or transfected protoplasts from mesophyll cells cultured in FK medium and mixed. Similarly, 5 ml of K3/0.4M sucrose+0.1 ppm NAA+0.2 ppm BA was added to each aliquot of transfected protoplasts from mesophyll cells cultured in FKH medium and mixed. The transfected protoplast suspensions were incubated overnight at 23° C. in the dark.

Transfected Zinnia protoplast suspensions prepared as described above were individually harvested by adding 9.5 ml of W5 solution, mixing the contents of each tube and centrifuging at 70×g for 10 minutes at 20° C. The bulk of the supernatant was removed by decanting and the protoplasts volume was brought up to 900 µl. From this, 300 µl of protoplasts were aliquoted into 5 ml polystyrene round-bottom tubes, re-suspended in a volume of 500 µl W5 medium and set aside for analysis of fluorescent reporter gene expression and cell viability. The protoplasts and the remaining solution were transferred to individual microtubes and pelleted by centrifugation at 420×g for 2 minutes at 20° C. The protoplast pellet was assayed for GUS reporter gene expression as described by Jefferson, R. A., 1987, Plant Mol. Biol. Rep. 5, 387. GUS (MUG) assays were performed using a Wallac (Turku, Finland) Victor$^2$ 1420 Multilabel Counter. Umbelliferone was detected using a 355 nm excitation filter and a 460 nm emission filter for 1 second.

Example 3

Determination of the Activity of E. grandis cOMT Promoter Constructs in Transformed Nicotiana benthamiana Nicotiana benthamiana transgenic lines were transformed with A. tumefaciens containing constructs comprising E. grandis OMT promoter sequences (SEQ ID NO: 113, bases 1-1643 or SEQ ID NO: 12) operatively linked to the GUS reporter gene. Transformed plants were hand-sectioned and examined microscopically for GUS staining. The promoter sequences were cloned into plasmid pBI-101 containing a GUS reporter gene.

Agrobacterium tumefaciens Transformation

Agrobacterium tumefaciens strain GV3101 was transformed with these constructs using electroporation. Electrocompetent A. tumefaciens cells were prepared according to the method of Walkerpeach and Velten, Plant Mol. Biol. Man. B11: 1-19, 1994. Construct DNA (4 ng) was added to 40 μl competent A. tumefaciens GV3101 cells and electroporation was carried out using a BTX Electro Cell Manipulator 600 at the following settings: Mode: T 2.5 kV Resistance high voltage (HV), Set Capacitance: C (not used in HV mode), Set Resistance: R R5 (129 Ohm), Set charging voltage: S 1.44 kV, Desired field strength: 14.4 kV/cm and Desired pulse strength: t 5.0 msec. 400 μl YEP liquid media (20 g/l yeast, 20 g/l peptone and 10 g/l sodium chloride) was added to the cuvette and the cells were allowed to recover for one hour at room temperature. Transformed bacteria in YEP medium were spread out on solid YEP medium containing 50 mg/l kanamycin and 50 mg/l rifampicin and incubated at 28° C. for two days to allow colony growth.

Confirmation of Transformation of Constructs into A. tumefaciens

To confirm that the constructs were transformed into A. tumefaciens, DNA from the A. tumefaciens colonies from the YEP plates were isolated using standard protocols and amplified using the polymerase chain reaction (PCR) with primers designed from the pBI-101 vector sequence. The primer sequences are given in SEQ ID NOS: 128 and 129 of the Sequence Listing. PCR reactions were set up following standard protocols and 30 PCR cycles were done with extension temperature of 72° C.

Transformation of Nicotiana benthamiana Leaf Explants with Agrobacterium

In the laminar flow hood, 6-8 young, expanding leaves were removed from N. benthamiana plants and cut into 5 mm squares. Approximately 10 pieces from each leaf were transferred to a deep Petri dish containing ToCo medium (MS+1 mg/l BA+0.1 mg/l NAA). A. tumefaciens was grown in YEP medium containing 50 mg/l kanamycin and 50 mg/l rifampicin at 28° C. for 16 hours, then centrifuged to pellet the cells. The cells were resuspended in MS liquid medium (Murashige and Skoog; Sigma, St Louis Mich.) without added hormone to an $OD_{600}$ of approximately 0.8. 15 to 20 ml of the Agrobacterium culture ($OD_{600}$=0.8) was added to each plate and soaked for 5 min with occasional gentle mixing. The leaf discs were blotted dry with sterile tissue paper, and 20 discs per plate were placed onto' fresh ToCo plates with the abaxial surface uppermost. The plates were sealed and incubated under lights in ambient conditions for 2 to 3 days.

Transfer of N. benthamiana Leaf Explants Co-Cultivated with A. tumefaciens to ToSe Selection Medium Plates.

After 3 days of co-cultivation, leaf explants were transferred from the ToCo co-cultivation plates onto ToSe selection plates (MS+1 mg/l BA+0.1 mg/l NAA, Timentin 200 mg/l and Kanamycin 100 mg/l), sealed and incubated under lights in ambient conditions. After 4 weeks on the selection medium, explants were cut into 4 to 8 pieces, transferred to fresh ToSe selection medium, sealed and incubated under lights in ambient conditions.

Subculture of Putative Transgenic N. benthamiana Explants onto Rooting Medium (TORt).

After subculture to elongation medium ToEl (MS without hormone, Timentin 200 mg/l and Kanamycin 100 mg/l), multiple buds/shoots per callus were observed on the explants. Healthy shoots approx. 1 cm long were excised, one per callus, and transferred to rooting medium TORt (MS without hormone, Timentin 200 mg/l and Kanamycin 100 mg/l) in tubs. Other shoots on the same callus were discarded to avoid duplicating the same transformation events. The tubs were sealed and incubated under lights in ambient conditions After 3 to 4 weeks, the plants were transferred to soil and grown at 22° C. with a 12 hour photoperiod.

GUS Expression in Transformed Tobacco Sections

Three weeks after transferring transformed plants to soil, the first side branch was sacrificed, and the following tissues were sectioned from the branch: 5-8 mm section at the base, mid and tip areas of the side branch, a leaf, root material and a floral bud. These tissues were immersed in GUS staining solution (0.5% Triton X-100, 1 mM X-GlcA-sodium salt (Duchefa, Haarlem, The Netherlands), 50 mM sodium phosphate buffer (pH 7.2), 20% methanol, pH 7.3) in an Eppendorf tube and vacuum infiltrated 3 times for 5 min. The samples were placed in a dark box, and incubated overnight at 37° C. on a shaker to allow color development. A preliminary check was done after 4 hours to detect any samples with early color development. The next day, the GUS solution was removed and the tissues destained using 70% Ethanol. The tissues were then photographed.

For photography, the sections of stem, leaf and root tissue were hand-sectioned and imaged using a microscope utilizing Metamorph software (Universal Imaging Corporation, Downingtown Pa.). The floral bud was sectioned down the middle, and then photographed using the Metamorph software. Stems from 2 to 3 tobacco plants that showed good expression were collected and cut into sections of smaller than 5 mm. The tissue sections were placed in vials containing freshly-prepared fixative (25 ml 100% ethanol, 2.5 ml glacial acetic acid, 5 ml 37% formaldehyde (Analar) and 17.5 ml water), with a vacuum applied twice for 15 min. The samples were incubated in fixative for 2 hours, a vacuum is applied for 15 min and the tissues were fixed overnight at 4° C. The fixative was removed and the tissue sections were dehydrated with a series of ethanol solutions (50%×2, 60%, 70%, 85%), each for 30 min at room temperature. The 85% ethanol solution was removed and replaced with 95% ethanol, and the samples were incubated overnight.

The tissues were then passaged into xylene at room temperature, according to the following protocol. The 95% ethanol was removed and replaced with 100% ethanol, 60 min. This solution was removed and replaced with fresh 100% ethanol for 30 min., which was removed and replaced with 25% Xylene: 75% Ethanol, 30 min, which was removed and replaced with 50% Xylene: 50% Ethanol, 30 min, which was removed and replaced with 75% Xylene: 25% Ethanol, 30 min, which was removed and replaced 3× with 100% Xylene, for 60 min each time.

The tissues were transferred to vials containing xylene and 20 paraplast chips. The vials were capped and incubated at room temperature overnight.

The vials were placed at 42° C. and left until the paraplast chips had dissolved. A total of 60-80 paraffin chips were added and allowed to dissolve during the day. The vials were then incubated at 62° C. overnight. During the next 48 hours, the paraplast was changed every 12 hours.

The tissues were embedded by filling an embedding cassette with liquid paraffin, placing the tissue in the correct orientation, and placing the cassette on a flat surface at 4° C. overnight to allow the paraffin to harden.

Safranin O Staining

Safranin O stain was prepared by dissolving 50 mg Safranin 0 (Raymon A Lamb Waxes and General Lab supplies, Wembley, Middlesex, UK) in a mixture of 2 ml ethanol/8 ml water. The stain was further diluted by adding 8 μl Safranin 0 to 1 ml of the ethanol/water mixture. Tissue was stained for 30 seconds, and the slide was dried and viewed.

Detection of GUS Expression in Tobacco Plants at Two to Three Months After Soil Transfer Seed was collected from all plants. Two or three plants that showed expression at the 3 week stage were selected and analyzed for GUS expression. The main stem was removed from the plants, as well as any other tissue that showed initial expression. These were stained for GUS expression as described above for the 3-week samples, except that the vacuum infiltration was done twice for 30 min.

All of the eight plants that were tested with the promoter construct comprising SEQ ID NO. 12 showed vascular tissue-specific GUS expression. The expression was specifically located in the xylem cells dignified) of the stem (base, mid and tip sections), and was not observed in the leaf or floral material. Expression was also observed in three of the roots tested. These results are comparable to those obtained with constructs comprising the 5' UTR of SEQ ID NO. 113 (nucleotides 1-1643), where expression was confined to xylem cells and differentiating cambium, but was not detected in nonvascular tissues.

Example 4

Analysis of Promotor Fragments Using TE Assay
Details of the Procedures used for Analysis of Promoters in the TE Assay are Described in a U.S. Provisional Application No. 60/345,397 filed Nov. 9, 2001, and in a Related US Patent Application filed on the Same Date as the Instant Application.

Zinnia elegans mesophyll cells were cultured in maintenance medium (FK) or TE inducing medium (FKH). Protoplasts were isolated and transformed with a plasmid containing the GUS (β-D-glucuronidase) reporter gene in frame with the specified E. grandis OMT promoter fragments. The constructs were tested, and the results are described in the table, below.

| Promoter construct | SEQ ID NO: | Figure | Relative level of activity in TE assay | Enhanced in TE-forming cells? |
|---|---|---|---|---|
| 534 bp | 131 | FIG. 7 | high | yes |
| 485 bp | 132 | FIG. 8 | high | yes |
| 306 bp | 133 | FIG. 9 | high | yes |
| 293 bp | 134 | FIG. 10 | high | yes |
| 119 bp | 135 | FIG. 11 | low | yes |
| 99 bp | 136 | FIG. 12 | low | yes |
| 66 bp | 137 | FIG. 13 | not detectable | no |

General Method

Transformation of tobacco plants: Reporter gene constructs were introduced into transgenic tobacco plants using Agrobacterium-mediated leaf tissue transformation (Burow et al., Plant Mol. Biol. Rep. 8:124-139 (1990).

Staining of Tissue Sections

The GUS staining protocol is described by Campisi et al., Plant J. 17:699-707, 1999.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, method, method step or steps, for use in practicing the present invention. All such modifications are intended to be within the scope of the claims appended hereto.

All of the publications, patent applications and patents cited in this application are herein incorporated by reference in their entirety to the same extent as if each individual publication, patent application or patent was specifically and individually indicated to be incorporated by reference in its entirety.

What is claimed is:

1. An isolated polynucleotide comprising the sequence of nucleotides 1525-1643 of SEQ ID NO: 113 comprising a functional vascular tissue-specific E. grandis cOMT promoter.

2. The isolated polynucleotide of claim 1, wherein the polynucleotide comprises the sequence selected from the group consisting of SEQ ID NO: 12, SEQ ID NO: 60, nucleotides 1-1643 of SEQ ID NO: 113, nucleotides 1019-1643 of SEQ ID NO: 113, nucleotides 1351-1643 of SEQ ID NO: 113, nucleotides 1338-1643 of SEQ ID NO: 113; nucleotides 1159-1643 of SEQ ID NO: 113; and nucleotides 1110-1643 of SEQ ID NO: 113.

3. The isolated polynucleotide of claim 1, wherein the polynucleotide comprises the sequence of SEQ ID NO: 113.

4. A genetic construct comprising a polynucleotide sequence of any one of claims 1-3.

5. A genetic construct comprising, in the 5'-3' direction:
(a) a promoter sequence;
(b) a DNA sequence of interest; and
(c) a gene termination sequence,
wherein the promoter sequence comprises a polynucleotide sequence of claim 1 or claim 2;
wherein said promoter sequence possesses vascular tissue-specific promoter function of the E.grandis cOMT gene.

6. The genetic construct of claim 5, wherein the DNA sequence of interest is operably linked to the promoter in an antisense orientation.

7. The genetic construct of claim 5, wherein the DNA sequence of interest is a coding sequence operably linked to the promoter in a sense orientation.

8. The genetic construct of claim 5, wherein the DNA sequence of interest is a RNAi expression construct.

9. The genetic construct of claim 5, wherein the DNA sequence of interest comprises a non-coding sequence operably linked to the promoter in a sense orientation.

10. A genetic construct comprising in the 5'-3' direction:
(a) a promoter sequence;
(b) a polynucleotide sequence of any one of claims 1-3; and
(c) a gene termination sequence,
wherein the promoter sequence in (a) comprises a xylem-specific promoter sequence that is different from the polynucleotide sequence of (b).

11. A genetic construct comprising in the 5'-3' direction:
(a) a promoter sequence;
(b) a polynucleotide sequence comprising the sequence of nucleotides 1525-1643 of SEQ ID NO: 113 inserted in said construct as a direct or inverted repeat; and
(c) a gene termination sequence,
wherein the promoter sequence in (a) comprises a xylem-specific promoter sequence that is different from the polynucleotide sequence of (b).

12. A host cell comprising the genetic construct of claim 4.

13. The host cell of claim 12, wherein the host cell is a plant cell.

14. A method for identifying a gene responsible for a desired function or phenotype, comprising:
(a) transforming a plant cell with the genetic construct of claim 5, wherein said DNA sequence of interest comprises said gene;
(b) cultivating the plant cell under conditions conducive to regeneration and mature plant growth to provide a transgenic plant in which the gene is expressed; and
(c) comparing the phenotype of the transgenic plant with the phenotype of a non-transformed plant, wherein said transgenic plant possesses the desired phenotype resulting from a change in lignification as compared to said non-transformed plant.

15. The method of claim 14, wherein said lignification is reduced in said transgenic plant as compared to said non-transformed plant.

16. The method of claim 14, wherein said promoter sequence directs transcription of said DNA sequence of interest in xylem or a tissue involved in xylogenesis of said transgenic plant.

17. An isolated polynucleotide sequence comprising a sequence selected from the group consisting of:
a polynucleotide comprising a 180-mer, a 220-mer, a 250-mer, a 300-mer, 400-mer, 500-mer or 600-mer complementary to SEQ ID NO: 12, SEQ ID NO: 60, or nucleotides 1-1643 of SEQ ID NO: 113.

18. An isolated polynucleotide sequence comprising a sequence selected from the group consisting of:
a polynucleotide comprising a 180-mer, a 220-mer, a 250-mer, a 300-mer, 400-mer, 500-mer or 600-mer of SEQ ID NO: 113.

19. A genetic construct comprising in the 5'-3' direction:
(a) a promoter sequence;
(b) a polynucleotide sequence of claim 17; and
(c) a gene termination sequence.

* * * * *